United States Patent
Lin et al.

(10) Patent No.: US 7,531,568 B2
(45) Date of Patent: May 12, 2009

(54) PPAR ACTIVE COMPOUNDS

(75) Inventors: Jack Lin, Hercules, CA (US); Dean R. Artis, Kensington, CA (US); Prabha N. Ibrahim, Mountain View, CA (US); Chao Zhang, Moraga, CA (US); Rebecca Zuckerman, Alameda, CA (US); Ryan Bremer, Albany, CA (US); Shenghua Shi, San Diego, CA (US); Byunghun Lee, Marina, CA (US)

(73) Assignee: Plexxikon, Inc., Berkeley, CA (US)

( * ) Notice: Subject to any disclaimer, the term of this patent is extended or adjusted under 35 U.S.C. 154(b) by 79 days.

(21) Appl. No.: 11/289,656

(22) Filed: Nov. 29, 2005

(65) Prior Publication Data

US 2006/0116416 A1 Jun. 1, 2006

Related U.S. Application Data

(60) Provisional application No. 60/715,312, filed on Sep. 7, 2005, provisional application No. 60/631,746, filed on Nov. 30, 2004.

(51) Int. Cl.
*A61K 31/405* (2006.01)
*C07D 403/02* (2006.01)

(52) U.S. Cl. .................. 514/414; 514/419; 548/465; 548/495

(58) Field of Classification Search .......... 514/415, 514/419; 548/469, 483, 484, 492
See application file for complete search history.

(56) References Cited

U.S. PATENT DOCUMENTS

| | | | |
|---|---|---|---|
| 3,489,767 A | 1/1970 | Yamamoto et al. | |
| 3,511,841 A | 5/1970 | Archer | |
| 3,557,142 A | 1/1971 | Bell | |
| 4,150,949 A | 4/1979 | Smith | |
| 4,564,610 A * | 1/1986 | Rahtz et al. ................ | 514/80 |
| 4,568,649 A | 2/1986 | Bertoglio-Matte | |
| 4,626,513 A | 12/1986 | Burton et al. | |
| 5,075,313 A | 12/1991 | Yu et al. | |
| 5,466,689 A | 11/1995 | Yamamoto et al. | |
| 5,747,276 A | 5/1998 | Hoch et al. | |
| 5,763,198 A | 6/1998 | Hirth et al. | |
| 5,840,485 A | 11/1998 | Lebl et al. | |
| 5,877,007 A | 3/1999 | Housey | |
| 6,090,912 A | 7/2000 | Lebl et al. | |
| 6,178,384 B1 | 1/2001 | Kolossvary | |
| 6,243,980 B1 | 6/2001 | Bronstein et al. | |
| 6,288,234 B1 | 9/2001 | Griffin | |
| 6,294,330 B1 | 9/2001 | Michnick et al. | |
| 6,329,389 B1 | 12/2001 | Suzuki et al. | |
| 6,395,768 B1 | 5/2002 | Pappolla et al. | |
| 6,635,655 B1 | 10/2003 | Jayyosi et al. | |
| 6,869,975 B2 | 3/2005 | Abe et al. | |
| 7,202,266 B2 | 4/2007 | Arnold et al. | |
| 7,348,338 B2 | 3/2008 | Arnold et al. | |

| | | |
|---|---|---|
| 2003/0216452 A1 | 11/2003 | Sredy et al. |
| 2004/0006071 A1 | 1/2004 | Simoneau et al. |
| 2005/0004115 A1 | 1/2005 | Sharma et al. |
| 2006/0111426 A1 | 5/2006 | Bonnert et al. |
| 2007/0149603 A1 | 6/2007 | Arnold et al. |
| 2008/0045581 A1 | 2/2008 | Arnold et al. |

FOREIGN PATENT DOCUMENTS

| | | |
|---|---|---|
| EP | 0154734 | 8/1990 |
| EP | 0620214 | 10/1994 |
| EP | 1219595 | 7/2002 |
| EP | 1285908 | 2/2003 |
| EP | 1661879 | 5/2006 |
| GB | 1128607 | * 12/1965 |
| GB | 1241637 | 8/1971 |
| GB | 2407318 | 4/2005 |
| RU | 2240793 | 11/2004 |
| WO | WO 91/13060 | 9/1991 |
| WO | WO 96/04906 | 2/1996 |
| WO | WO 00/64876 | 11/2000 |
| WO | WO 2000/064876 | 11/2000 |
| WO | WO 01/38305 | 5/2001 |
| WO | WO 2002/030863 | 4/2002 |
| WO | WO 03/064387 | 8/2003 |
| WO | WO 2004/007439 | 1/2004 |
| WO | WO 2004/007451 | 1/2004 |
| WO | WO 2004/056740 | 7/2004 |
| WO | WO 2004/058164 | 7/2004 |
| WO | WO 2004/063190 | 7/2004 |
| WO | WO 2005/009958 | 2/2005 |
| WO | WO 2005/037763 | 4/2005 |
| WO | WO 2005/040112 | 5/2005 |
| WO | WO 2005/040114 | 5/2005 |
| WO | WO 2005/044787 | 5/2005 |
| WO | WO 2005/054176 | 6/2005 |
| WO | WO 2005/056522 | 6/2005 |
| WO | WO 2005/060958 | 7/2005 |
| WO | WO 2005/092131 | 10/2005 |
| WO | WO 2005/121141 | 12/2005 |

(Continued)

OTHER PUBLICATIONS

Guo et al., YaoXue Xuebao (Journal of Pharmaceutical Science), 1987, 22(9), 671-8, Abstract from STN search report.*

(Continued)

*Primary Examiner*—Kamal A Saeed
*Assistant Examiner*—Yong Chu
(74) *Attorney, Agent, or Firm*—Foley & Lardner LLP

(57) ABSTRACT

Compounds are described that are active on at least one of PPARα, PPARδ, and PPARγ, which are useful for therapeutic and/or prophylactic methods involving modulation of at least one of PPARα, PPARδ, and PPARγ.

12 Claims, No Drawings

OTHER PUBLICATIONS

U.S. Appl. No. 11/289,781; 11/517,010; 11/517,573; 11/679,738; 11/679,777; and 11/679,792.*

Buchan and Hassall, PPAR agonists as direct modulators of the vessel wall in cardiovascular disease. Med. Res. Rev. 20(5): 350-366, 2000.

VanZandt et al., Discovery of 3-[(4,5,7-Trifluorobenzothiazol-2-yl)methyl]indole-N-acetic acid (Lidorestat) and congeners as highly potent and selective inhibitors of aldose reductase for treatment of chronic diabetic complications. J.Med.Chem., 48:3141-3152, 2005.

Mahindroo et al., Novel indole-based peroxisome proliferator-activated receptor agonists: Design, SAR, structural biology, and biological activities. J.Med.Chem. 48:8194-8208, 2005.

International Search Report from PCT Application PCT/US2006/034747.

Shang-Shing et al., "Synthetic applications of Tricarbonyl [eta<5>-1-(phenylsulfonyl)-cyclohexadienyl]iron(I) complex." Tetrahedron Letters, 37(30):5373-5376, 1996.

Corton et al., Perioxisome proliferators-activated receptors: Mediators of phthalate ester-induced effects in the male reproductive tract? Toxicological Sciences, 83:4-7, 2005.

Trost et al., 2-Alkoxybenzo-1,3-dithiole 1,1,3,3-tetraoxide: A carbonyl 1,1-dipole synthon. J. Am. Chem. Soc., 106(8): 2469-2471, 1984.

Yato et al., Reduction of carboxylic esters with triethyl silane in the combined use of titanium tetrachloride and trimethylsilyl trifluoromethanesulfonate. Tetrahedron, 57: 5353-5359, 2001.

The International Search Report and the Written Opinion of the International Searching Authority for PCT Application No. PCT/US2004/23234 dated Nov. 1, 2004.

Seehra et al., Preparation of indole derivatives as phospholipase enzyme inhibitors for treatment of inflammatory conditions. CAPLUS, 2003:1275.

Lala et al, Role of nitric oxide in tumor progression: Lessons from experimental tumors. Cancer and Metastasis Reviews, 17(1): 91-106, 1998.

Golub et al., Molecular classification of cancer: Class discovery and class prediction by gene expression monitoring. Science, 286: 531-537, 1999.

Cancer (online), retrieved from http://www.nim.nih.gov/medlineplus/cancer.html (retrieved Jul. 6, 2007).

Cancer (online), retrieved from http://en.wikipedia.org/wiki/Cancer (retrieved Jul. 6, 2007).

Eczema (online), retrieved from http://www.nim.nih.gov/medlineplus/eczema.html (retrieved Dec. 19, 2007).

Colitis (online), retrieved from http://www.nim.nih.gov/medlineplus.colitis.html (retrieved Dec. 19, 2007).

Diabetes Mellitus (online), retrieved from http://www.merck.com/mmpe/print/sec12/ch158b.html (retrieved Apr. 17, 2007).

FDA Clinical Trials [online], [retrieved on Mar. 13, 2008]. Retrieved from the Internet, URL: http://www.fda.gov/oashi/clinicaltrials/default htm.

Ulcerative Colitis [online], [retrieved on Mar. 13, 2008]. Retrieved from the Internet, URL: http://www.nlm.nih.gov/medlineplus/ulcerativecolitis.html.

Colitis [online], [retrieved on Mar. 13, 2008]. Retrieved from the Internet, URL: http://www.nl. nih.gov/medlineplus/ency/article/000259.htm.

Collagenous Colitis [online], [retrieved on Mar. 13, 2008]. Retrieved from the Internet, URL: http://digestive. niddk.nih.gov/ddiseases/pubs/collagenouscolitis/index.htm.

Acton et al., Benzoyl 2-methyl indoles as selective PPARγ modulators. Bioorganic & Medicinal Chemistry Letters, 15:357-362, 2005.

Basanagoudar et al., Synthesis of indole-3-propionic acids and 3-(3-aminopropyl indoles. XP002483945, retrieved from STN, Database accession No. 1975:111898, Abstract.

Bourdais et al., Derives sulfures d'indole V(*). Indolethiols-3 et leurs thioethers aminoethyliques et carboxymethyliques. Eur. J. Med. Chem., 9(3): 269-273, 1974.

Cancer (online), retrieved on Mar. 17, 2008, retrieved from: http://www.nlm.nih.gov/medlineplus/cancer.html.

ChemDiv, Inc. Product Library, File CHEMCATS, XP-002385890, Database Accession No. 2005 :3568688.

Chemical Library Supplier: Ambinter, XP-002385889, Database accession No. RN 681279-99-2 to RN 681217-55-0.

Collot et al., Heck cross-coupling reaction of 3-iodoindazoles with methyl acrylate: a mild and flexible strategy to design 2-azatryptamines. XP002483946, retrieved from STN, Database accession No. 2000:431314.

Cross et al., Selective thromboxane synthetase inhibitors. 2. 3-(1H-Imidazol-1-ylmethyl)-2-methyl-1H-indole-1-propanoic acid and analogues. J.Med.Chem, 29:342-346, 1986.

Diabetes Mellitus (DM) (online, retrieved on Mar. 17, 2008, retrieved from http://www.merck.com/mmpe/print/sec12/ch158/ch158b.html.

Eczema (online), retrieved on Mar. 17, 2008, retrieved from: http://www.nlm.nih.gov/medlineplus/eczema.html.

Galun et al., Ethers of indoxylic acid, J. Heterocyclic Chem., 16:221-224, 1979.

Garcia et al., a Novel synthesis of 3-cyanoindoles and a new route to indole-3-carboxylic acid derivatives. Tetrahedron Letters, 26(15): 1827-1830, 1985.

International Search report for PCT Patent Application PCT/US2005/043412.

International Search report for PCT Patent Application PCT/US2005/043271.

Kuwano et al., Highly enantioselective synthesis of chiral 3-substituted indulines by catalytic asymmetric hydrogenation of indoles. Organic Letters, 6(13): 2213-2215, 2004.

Levkovskaya et al., Synthesis of (3-Indolysulfanyl)alkanecarboxylic acids. Russian Journal of Organic Chemistry, 38(11): 1641-1646, 2002.

Mahindroo et al., Novel indole-based peroxisome proliferator-activated receptor agonists: Design, SAR, structural biology, and biological activities. J.Med.Chem., 48:8194-8208, 2005.

Partial European Search Report for EPO Patent Application No. 04778641.

Silverman et al., "Drug Discovery, Design and Development." Chapter 2 in *The Organic Chemistry of Drug Design and Drug Action*, San Diego: Academic Press, 1992, p. 4-51.

Alfred, et al., "Peroxisome proliferator-activated receptor gamma is frequently downregulated in a diversity of sporadic nonmedullary thyroid carcinomas," *Oncogene* 22:3412-3416 (2003).

Alfthan, "Surface Plasmon Resonance Biosensors as a Tool in Antibody Engineering," *Biosensors & Bioelectronics* 13:653-63 (1998).

Al-Obeidei, "Peptide and Peptidomimetic Libraries - Molecular Diversity and Drug Design," *Mol Biotechnol* 9(3):205-223 (1998).

Amersdorfer and Marks, "Phage Libraries for Generation of Anti-Botulinum scFv Antibodies," *Methods in Molecular Biology* 145:219-40 (2001).

Azimov, et al., "Nucleophilic Substitution Reactions in 6-Chloro-5-Azaindolines," *Chem. Heterocycl. Compd.* 17(12):1208-1216 (1981).

Bartlett et al., "Caveat: A Program to facilitate the structure-derived design of biologically active molecules." In Molecular Recognition: Chemical and Biological Problems. The Proceedings of an International Symposium, University of Exeter, Apr. 1989, *Royal Society of Chemistry*, Cambridge 182-196 (1989).

Bagshaw and Harris, "Measurement of Ligand Binding to Proteins," *Spectrophotometry and Spectrofluoroimetry: A Practical Approach* 4:91-113 (1981).

Bell, "Spectroscopy in Biochemistry," *CRC Press* 1:155-194 (1981).

Belletire, J.L., "Acylcyanamides: Versatile Synthetic Intermediates," *Synthetic Communications* 18:2063-2071 (1988).

Berger and Wagner, "Physiological and Therapeutic Roles of Peroxisome Proliferator-Activated Receptors," *Diabetes Technology & Therapeutics* 4:163-174 (2002).

Boehm, et al., "Novel Inhibitors of DNS Gyrase: 3D Structure Based Biased Needle Screening, Hit Validation by Biophysical Methods, and 3D Guided Optimization. A Promising Alternative of Random Screening," *J. Med. Chem.* 43:2664-2674 (2000).

Bohacek, et al., "Multiple Highly Diverse Structures Complementary to Enzyme Binding Sites: Results of Extensive Application of a *de Nevo* Design Method Incorporating Combinatorial Growth," *J. Am. Chem. Soc.* 116:5560-5571 (1994).

Böhm, "On the Use of LUDI to Search the Fine Chemicals Directory for Ligands of Proteins of Known Three-Dimensional Structure," *J. Comp. Aided Molec. Design* 8:623 (1994).

Bolger and Sherman, "Computer Modeling of Combining Site Structure of Anti-Hapten Monoclonal Antibodies," *Methods in Enz.* 203:21-45 (1991).

Brenner et al., "Encoded Combinatorial Chemistry," *Proc. Natl. Acad. Sci. USA* 89:5381-5383 (1992).

Buchheit, et al., "The Serotonin 5-HT$_4$Receptor. 2. Structure - Activity Studies of the Indole Carbazimidamide Class of Agonists," *J. Med. Chem.* 38:2331-2338 (1995).

Burstein, et al., "Use of the Peroxisome Proliferator-Activated Receptor (PPAR) Y Ligand Troglitazone as Treatment for Refractory Breast Cancer: a Phase II Study," *Breast Cancer Research and Treatment* 79:391-397 (2003).

Bychikhina, et al., "Electrophilic Substitution Reactions in 1-Benzyle-6-Methoxy-7-Cyano-5-Azaindole and 6-Oxo-5-Azaindoline," *Chemistry of Heterocyclic Compounds* 18:268-271 (1982).

Cantello, et al., "[[a-(Heterocyclylamino)alkoxy]benzyl]-2,4-thiazolidinediones as Potent Antihyperglycemic Agents," *J. Med. Chem.* 37:3977-3985 (1994).

Cao, et al., "Dual Probes for the Dopamine Transporter and o$_1$Receptors: Novel Piperazinyl Alkyl-bis(4'-fluorophenyl)amine Analogues as Potential Cocaine-Abuse therapeutic Agents," *J. Med. Chem.* 46:2589-2598 (2003).

Carell et al., "New Promise in Combinatorial Chemistry: Synthesis, Characterization, and Screening of Small-Molecule Libraries in Solution," *Chem. Biol.* 2:171-183 (1995).

Chabala, "Solid-Phase Combinatorial Chemistry and Novel Tagging Methods for Identifying Leads," *Curr Opin biotechnol* 6(6):632-p (1995).

Checovich et al., "Fluorescence Polarization - a New Tool for Cell and Molecular Biology," *Nature* 375:254-256 (1995).

Cheung, et al., "Synthesis of 2-chloro-5,y-dihydro-6H-pyrrolo[2,3-d]pyrimidin-6-one," *Tetrahedron Letters* 42:999-1001 (2001).

Chong, et al., "Molecular dynamics and free-engry calculations applied to affinity maturation in antibody 48G7," *PNAS* 96:14330-14335 (1999).

Clark et al., "Pro_Ligand: An Approach to De Novo Molecular Design. 1. Application to the Design of Organic Molecules," *J. Comp. Aided Molec. Design* 9:13-32 (1995).

Coe et al., "Solution-Phase Combinatorial Chemistry," *Mol Divers.* 4(1):31-38 (1998-99).

Colman, "Structure-Based Drug Design," *Current Opinion In Struc. Biol.* 4:868-874 (1994).

Cornell, et al., "A Second Generation Force Field for the Simulation of Proteins, Nucleic Acids, and Organic Molecules," *J. Am. Chem. Soc.* 117:5179-5197 (1995).

Cremlyn and Hornby, "Sulphonohydrazides and Related Compounds. Part XI. Some Substituted Aryl Ether Sulphonohydrazides," *J. of Chem. Soc. C.* 1341-1345 (1969).

Cronet, et al., "Structure of the PPARα and -γ Ligand Binding Domain in Complex with AZ 242; Ligand Selectivity and Agonist Activation in the PPAR Family," *Structure* 9:699-706 (2001).

Cwirla et al., "Peptides on Phage. A Vast Library of Peptides for Identifying Ligands," *Biochemistry* 87:6378-6382 (1990).

Dandliker, et al., "Equilibrium and Kinetic Inhibition Assays Based Upon Fluorescence Polarization," *Methods in Enzymolog* 74:3-28 (1981).

Dinh and Armstrong, "Synthesis of Ketones and Aldehydes via Reactions of Weinreb-Type Amides on Solid Support," *Tet. Lett.* 37(8):1161-1164 (1996).

Dolle and Nelson, "Comprehensive survey of Combinatorial library synthesis: 1998," *J Comb Chem* 1(4):235-82 (1999).

Donni and Kollman, "Calculation and Prediction of Binding Free Energies for the Matrix Metalloproteinasas," *J. Med. Chem.* 43:4180-4188 (2000).

Downs, et al., "Similarity Searching and Custering of Chemical-Structure Databases Using Molecular Property Data," *J. Chem. Inf. Comput. Sci.* 34:1094-1102 (1994).

Eils, et al., "Complete Regioselectivity in Staurosporine Chromophore Formation," *Synthesis* 2:275-281 (1998).

Eliseev and Lehn, "Dynamic Combinatorial Chemistry: Evolutionary Formation and Screening of Molecular Libraries," *Current Topics in Microbiology & Immunology* 243:159-172 (1999).

Enjalbal et al., "Mass Spectrometry in Combinatorial Chemistry," *Mass Spectrometry Reviews* 19:139-161 (2000).

Fajas, et al., "The Organization, Promoter Analysis, and Expression of the Human PPARγ Gene," *Journ. Biol. Chem.* 272(30):18779-18789 (1997).

Felder, E.R., "The Challenge of Preparing and Testing Combinatorial Compound Libraries in the Fast Lane, at the Front End of Drug Development," *Chimia* 48:531-541 (1994).

Filla, et al., "Novel Potent 5-HT$_{1F}$ Receptor Agonists: Structure-Activity Studies of a Series of Substituted N-[3-1-Methyl-4-pioeridinyl)-1H-pyrrolo[3-2-b]pyridine-5-yl]amides[§] ," *J. Med. Chem.* 46:3060-3071 (2003).

Fivash et al., "BIAcore for Macromolecular Interaction," *Current Opinion in Biotechnology* 9:97-101 (1998).

Freidinger RM., "Nonpeptidic Ligands for Peptide and Protein Receptors," *Current Opinion in Chemical Biology* 3:395-406 (1999).

Frølund, et al., "Novel Class of Potent 4-Arylalkyl Substituted 3-Isoxazolol GABA$_A$Antagonists: Synthesis, Pharmacology, and Molecular Modeling," *J. Med. Chem.* 45:2454-2468 (2002).

Fu, et al., "Oleylethanolamide Regulates Feeding and Body Weight Through Activation of the Nuclear Receptor PPAR-α," *Nature* 425:90-93 (2003).

Gallop, et al., "Applications of Combinatorial Technologies to Drug Discovery. 1. Background and Peptide Combinatorial Libraries," *J. Med. Chem.* 37(9):1233-1251 (1994).

Gingras and Harpp, "A Practical, One-Step Synthesis of Primary Thiols Under Mild and Neutral Conditions Using Bis(Triorganotin) Sulfides," *Tet. Lett.* 31(10):1397-1400 (1990).

Goodford, P., "A Computational Procedure for Determining Energetically Favorable Binding Sites on Biologically Important Macromolecules," *J. Med. Chem.* 28:849-857 (1985).

Goodsell and Olson, "Automated Docking of Substrates to Proteins by Simulated Annealing," *Proteins: Structure, Function and Genetics* 8:195-202 (1990).

Gordon et al., "Applications of Combinatorial Technologies to Drug Discovery. 2. Combinatorial Organic Syntheis, Library Screening Strategies, and Future Directions," *J. Med. Chem.* 37(10):1385-1401 (1994).

Gordon and Ford, "Detection of Peroxides and Their Removal," *The Chemist's Companion: A Handbook of Practical Data, Techniques, and References* p. 437 (1972).

Gram H., "Phage Display in Proteolysis and Signal Transduction," *Combinatorial Chemistry & High Throughput Screening* 2:19-28 (1999).

Gravert and Janda, "Synthesis on Soluble Polymers: New Reactions and the Construciton of Small Molecules," *Curr Opin Chem Biol* 1(1):107-113 (1997).

Guida, C., "Software for Structure-Based Drug Design," *Current Opinion In Struc. Biol.* 4:777-781 (1994).

Hanselman et al., "A cDNA-Dependant Scintillation Proximity Assay for Quantifying Apolipoprotein A-1," *J. Lipid res.* 38:2365-2373 (1997).

Hague, et al., "Potent, Low-Molecular-Weight Non-Peptide Inhibitors of Malarial Aspartyl Protease Plasmepsin II," *J. Med. Chem.* 42:1428-1440 (1999).

Heck, et al., "Conversion of Primary Amides to Nitriles by Aldehyde-Catalyzed Water Transfer," *J. Org. Chem.* 61:6486-6487 (1996).

Heim and Tsien, "Engineering Green Fluorescent Protein for Improved Brightness, Longer Wavelengths and Fluorescence Resonance Energy Transfer," *Curr. Biol.* 6:178-182 (1996).

Houghten, "Generation and Use of Synthetic Peptide Combinatorial Libraries for Basic Research and Drug Discovery," *Nature* 354:84-86 (1991).

Houghten, "Peptide Libraries: Criteria and Trends," *Trends in Genetics* 9(7):235-239 (1993).

Houghton, "Parallel Array and Mixture-Based Synthetic Combinatorial Chemistry: Tools for the Next Millennium," *Annu Rev Pharmacol Toxicol* 40:273-282 (2000).

Hughes-Jones, et al., "Synthesis of Rh Fv Phage-Antibodies Using VH and VL Germline Genes," *British Journal of Haematology* 105:811-816 (1999).

Hurd and Bauer, "A Novel Rearrangement of Hydroxamic Acids Using Sulfonyl Chlorides," *J. Am. Chem.* 76:2791-2792 (1954).

Imamoto, et al., "A One-Flask Conversion of Carboxylic Acids into Nitriles," *Synthesis* 142-143 (1983).

Jarvis and Patrick, "Clustering Using a Similarity Measure Based on Shared Near Neighbors," *IEEE Transactions on Computers* 11:1025-1034 (1973).

Joseph-McCarthy D., "Computational Approaches to Structure-Based Ligand Design," *Pharmacology & Therapeutics* 84:179-191 (1999).

Juby, et al., "Preparation and Antiinflammatory Properties of Some 1-Substituted 3-(5-Tetrazolylmethyl) Indoles and Homologs," *J. Med. Chem.* 12:396-401 (1969).

Kahl et al., "A Multiple-Approach Scintillation Proximity Assay to Measure the Association Between Ras and Raf," *Anal. Biochem.* 243:282-283 (1996).

Kim and Kahn, "A Merger of Rational Drug Design and Combinatorial Chemistry: Development and Application of Peptide Secondary Structure Mimetics," *Combinatorial Chemistry & High Throughput Screening* 3:167-183 (2000).

Kirkpatrick et al., "Structure-Based Drug Design: Combinatorial Chemistry and Molecular Modeling," *Combinatorial Chemistry & High Throughput Screening* 2:211-221 (1999).

Kitamura, et al., "Synthesis of Quinolines and 2H-Dihydropyrroles by Nucleophilic Substitution at the Nitrogen Atom of Oxime Derivatives," *Synthesis* 15:2415-2426 (2003).

Kundu et al., "Combinatorial Chemistry: Polymer Supported Synthesis of Peptide and Non-Peptide Libraries," *Progress in Drug Research* 53:89-156 (1999).

Kuntz et al., "Structure-Based Molecular Design," *Acc. Chem. Res.* 27(5):117-123 (1994).

Kuntz et al., "A Geometric Approach to Macromolecule-Ligand Interactions," *J. Mol. Biol.* 161:269-288 (1982).

Lam et al., "A New Type of Synthetic Peptide Library for Identifying Ligand-Binding Activity," *Nature* 354:82-84 (1991).

Lance and Williams, "A General Theory of Classificatory Sorting Strategies 1. Hierarchical Systems," *The Computer Journ.* 9:373-380 (1967).

Lebl et al., "One-Based-One-Structure Combinational Libraries," *Biopolymers* 37:177-198 (1995).

Leibowitz, et al., "Activation of PPAR δ Alters Lipid Metabolism in db/db Mice," *FEBS Lett.* 473:333-336 (2000).

Liparoto and Ciardelli, "Biosensor Analysis of the Interleukin-2 Receptor Complex," *Journal fo Molecular Recognition* 12:316-321 (1999).

Lipinski et al., "Experimental and Computational Approaches to Estimate Solubility and Permeability in Drug Discovery and Development Settings," *Advanced Drug Delivery Reviews* 23:3-25 (1997).

Lipschultz et al., "Experimental Design for Analysis of Complex Kinetics Using Surface Plasmon Resonance," *Methods* 20(3):310-318 (2000).

Lohray, et al., "(—)3-[4-[2-(Phenoxazin-10-yl)ethoxy]-2-ethoxypropanoic Acid [(—)DRF 2725]: A Dual PPAR Agonist with Potent Antihyperglycemic and Lipid Modulating Activity," *J. Med. Chem.* 44:2675-2678 (2001).

Lynch, et al., "Pyrazolo[3-4-b]pyridines: Syntheses, reactions and nuclear magnetic resonance spectra," *Candian Journ. of Chem.* 66:420-428 (1988).

Madden et al., "Synthetic Combinatorial Libraries: Views on Techniques and Their Application," *Perspectives in Drug Discovery and Design* 2:269-285 (1995).

Märcker, C., "Mittheilungen aus dem chemischen Laboratorium in Greifswald," *Justus Liebigs Ann. Chem.* 136:75-95 (1865).

Malmborg and Borrebaeck, "BIAcore As a Tool in Antibody Engineering," *Journal of Immunological Methods* 183:7-13 (1995).

Malmqvist et al., "Biomolecular Interaction Analysis: Affinity Biosensor Technologies for Functional Analysis of Proteins," *Current Opinion in Chemical Biology* 1:378-383 (1997).

Malmqvist, M., "Biacore: An Affinity Biosensor System for Characterization of Biomolecular Interactions," *Biochemical Society Transactions* 27:335-340 (1999).

Markiewicz et al., "Synthetic Oligonucleotide Combinatorial Libraries and Their Applications," *II Farmaco* 55:174-177 (2000).

Martin, Y., "Computer-Assisted Rational Drug Deisgn," *Methods Enz.* 203:587-613 (1991)

Massova and Kollman, "Computational Alanine Scanning to Probe Protein - Protein Interactions: A Novel Approach to Evaluate Binding Free Energies," *Journ. of Amer. Chem. Soc.* 121(36):8133-8143 (1999).

Mazéas, et al., "Synthesis of New Melatoninergic Ligands Including Azaindole Moiety," *Heterocycles* 50(2):1065-1080 (1999).

McGovern, et al., "A Common Mechanism underlying Promiscuous Inhibitors from Virtual and High-Throughput Screening," *J. Med. Chem.* 45:1712-1722 (2002).

Meng et al., "Automated Docking With Grid-Based Energy Evaluation," *J. Compt. Chem.* 13(4):505-524 (1992).

Merritt, A., "Solution Phase Combinatorial Chemistry," *Comb Chem High Throughput Screen* 1:57-72 (1998).

Miller et al., "FLOG: A System to Select 'Quasi-Flexible' Ligands Complementary to a receptor of Known Three-Dimensional Structure," *J. Comp. Aided Molec. Design* 8:153-174 (1994).

Miranker and Karplus, "Functionality Maps of Binding Sites: A Multiple Copy Simultaneous Search Method," *Proteins: Structure, Function, and Genetics* 11:29-34 (1991).

Mitra et al., "Fluroescence Resonance Energy Transfer Between Blue-Emitting and Red-Shifted Exitation Derivatives of the Green Fluroescent Protein," *Gene* 173:13-17 (1996).

Molina, et al., "One Pot Conversion of Alkyl Halides into Thiols Under Mild Conditions," *Tetrahedron Lett.* 26(4):469-472 (1985).

Mogensen, et al., "Design and Synthesis of Novel PPARal γ/ δ Triple Activators Using a Known PPAR al γ Dual Activator as Structural Template," *Bioorg. & Med. Chem. Lett.* 13:257-260 (2003).

Neidle and Jenksin, "Molecular Modeling to Study DNA Intercalation by Anti-Tumor Drugs," *Methods Enz.* 203:433-458 (1991).

Nichols et al., "Development of a Scintillation Proximity Assay for peroxisome Proliferator-Activated Receptor γ Ligand Binding Domain," *Anal. Biochem.* 257:112-119 (1998).

Nolte, et al., "Ligand Binding and Co-Activator Assembly of the Peroxisome Proliferator-Activated Receptor-γ," *Nature* 395:137-143 (1998).

O'Shannessy and Winzor, "Interpretation of Deviations Form Pseudo-First-Order Kinetic Behavior in the Characterization of Ligand Binding by Biosensor Technology," *Analytical Biochemistry* 236:275-283 (1996).

O' Shannessy, D., "Determination of Kinetic Rate and Equilibrium Binding Constants for Macromolecular Interactions: a Critique of the Surface Plasmon Resonance Literature," *Current Opinions in Biotechnology* 5:65-71 (1994).

Oliver, et al., "A Selective Peroxisome Proliferator-Activated Receptor δ Agonist Promotes Reverse Cholesterol Transport," *PNAS* 98(9):5306-5311 (2001).

Oster and Harris, "Generation and Reactions of the Dianionof 3-Hydroxy-5-methylisoxazole, a Covenient β-Keto Amide Synthon. Total Synthesis of Muscimol," *J. Org. Chem.* 48:4307-4311 (1983).

Parker et al., "Development of High Throughout Screening Assays Using Fluorescence Polarization: Nuclear Receptor-Ligand-Binding and Kinase/Phosphatase Assays," *J Biomol Screen* 5(2):77-88 (2000).

Pearlman and Charifson, "Are Free Energy Calculations Useful in Practice? A Comparison with Rapid Scoring Functions for the p38 MAP Kinase Protein System," *J. Med. Chem.* 44:3417-3423 (2001).

Perrin D., "Nucleic Acids for Recognition and Catalysis: Landmarks, Limitations, and Looking to the Future," *Combinatorial Chemistry & High Throughput Screening* 3:243-269 (2000).

Plunkett and Ellman, "A Silicon-Based Linker for Traceless Solid-Phase Synthesis," *J. Org. Chem.* 60:6000-6007 (1995).

Poul et al., "Selection of Tumor-Specific Internalizing Human Antibodies From Phage Libraries," *Journal of Molecular Biology* 301:1149-1161 (2000).

Price et al.; "Summary Report on the ISOBM TD-4 Workshop: Analysis of 56 Monoclonal Antibodies Against the MUC1 Mucin," *Tumor Biology* 19(1):1-20 (1998).

Ripka, et al., "Aspartic Protease Inhibitors Designed from Computer-Generated Templates Bind as Predicted," *Org. Lett.* 3(15):2309-2312 (2001).

Sakamoto, et al., "Condensed Heteroaromatic Ring Systems. Part 24. [1,2] Synthesis of Rigidin, a Pyrrolo[2-3-d]Pyrimidine Marine Alkaloid," *J. Chem. Soc.* 5:401-494 (1996).

Sauerberg, et al., "Novel Tricyclia-α-alkyloxyphenylproplonic Acids: Dual PPAR α/γ Agonists with Hypolipidemic and Antidiabetic Activity," *J. Med. Chem.* 45:789-804 (2002).

Schweizer and Hindsgaul, "Combinatorial Synthesis of Carbohydrates," *Curr Opin Chem Biol* 3(3):291-298 (1999).

Seela, et al., "7-Desaza-Isostere von 2'-Desoxyxanthosin und 2'-Desoxyspongosin - Synthese via Glycosylierung von 2,4-Dichlor-7H-pyrrolo[2,3-d]pyrimidin," *Liebigs Ann. Chem.* 312-320 (1985).

Seethala, et al., "Untitled," *Homogenus Assays: AlphaScreen* 106-110 (2001).

Selvin, P., "Fluorescence Resonance Energy Transfer," *Meth. in Enzymology* 246:300-334 (1995).

Sheets et al., "Efficient Construction of a Large Nonimmune Phage Antibody Library: the Production of High-Affinity Human Single-Chain Antibodies to Protein Antigens," (published erratum) *Proc Natl Acad Sci USA* 95(11):6157-6162 (1998).

Scholtz, M., "Das Verhalten des α-Methyl-indols gegen Aldehyde und Ameisensäure," *Chem. Ber.* 46:2138-2146 (1913).

Siegel et al., "Mass Spectral Analysis of a Protein Complex Using Single-Chain Antibodies Selected on A Peptide Target: Applications to Functional Genomics," *Journal of Molecular Biology* 302:285-293 (2000).

Staels, et al., "Activation of Human Aortic Smooth-Muscle Cells is Inhibited by PPARα but not by PPARγ Activators," *Nature* 393-790-793 (1998).

Sun, C., "Recent Advances in Liquid-Phase Combinatorial Chemistry," *Combinatorial Chemisty & High Throughput Screening.* 2:299-318 (1999).

Sun, et al., "Design, Synthesis, and Evaluations of Substituted 3-[3- or 4-Carboxyethylphrrol-2-yl)methylidenyl]indolin-2-ones as Inhibitors of VEGF, FGF, and PDGF Receptor Tyrosine Kinases," *J. Med. Chem.* 42:5120-5130 (1999).

Undenfriend et al., "Scintillation Proximity Assay: A Sensitive and Continuous Isotopic Method for Monitoring Ligand/Receptor and AntigenAntibody Interactions," *Anal. Biochem.* 161:494-500 (1987).

Van Regenmortel, "Use of Biosensors to Characterize Recombinant Proteins," *Developments in Biological Standardization* 83:143-51 (1994).

Vely, et al., "BIAcor® Analysis to Test Phosphopeptide-SH2 Domain Interactions," *Methods in Molecular Biology* 121:313-321 (2000).

Weidner-Wells, et al., "The Synthesis and Antimicrobial Evaluation of a New Series of Isoxazolinyl Oxazolidinones," *Bioorg. & Med. Chem. Lett.* 14:3069-3072 (2004).

Wessjohann, "Synthesis of Natural-Product-Based Compound Libraries," *Curr Opin Chem Biol* 4(3):303-309 (2000).

Willett, P., "Chemical Similarity Searching," *J. Chem. Inf. Comput. Sci.* 38:983-996 (1998).

Wilson and Hyslop, "Application of the Grignard Reaction to some Acetylenic Compounds. Part I. Preparation of Diacetylenic Glycols," *J. Chem. Soc.* 2612-2618 (1923).

Xu, et al., "Structural Basis for Antagonist-Medicated Recruitment of Nuclear Co-Repressors by PPARα," *Nature* 415:813-817 (2002).

Xu, et al., "Molecular Recognition of Fatty Acids by Peroxisome Proliferator-Activated Receptors," *Molecular Cell* 3:397-403 (1999).

Davis et al., A convenient synthesis of bisindoyl- and indolylaryl-maleic anhydrides. Tetahedron Letters, 31(16):2353-2356, 1990.

Holzapfel and Olivier, The synthesis of a γ-keto-α-amino acid, a key intermediate in the synthesis of monatin, a new natural sweetener. Synthetic Communications, 23(18):2511-26, 1993.

Kethca et al., Synthesis of alkyl-substututed N-protected indoles via acylation and reductive deoxygenation, J. Organic Chemistry, 54(18):4350-4356, 1989.

Chang et al., Substituted imidazoles as glucagon receptor antagonists. Bioorganic and Medicinal Chem. Lett., 11:2549-2553, 2001.

* cited by examiner

SEQUENCE LISTING

<160> NUMBER OF SEQ ID NOS: 13

<210> SEQ ID NO 1
<211> LENGTH: 1014
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: CDS
<222> LOCATION: (88)..(960)

<400> SEQUENCE: 1

```
taatacgact cactataggg gaattgtgag cggataacaa ttcccctcta gaaataattt      60
tgtttaactt taagaaggag atatacc atg ggc agc agc cat cat cat cat cat     114
                              Met Gly Ser Ser His His His His His
                                1               5 cac agc agc ggc ctg gtg ccg cgc ggc agc cat atg gaa act gca gat       162
His Ser Ser Gly Leu Val Pro Arg Gly Ser His Met Glu Thr Ala Asp
 10              15                  20                  25 ctc aaa tct ctg gcc aag aga atc tac gag gcc tac ttg aag aac ttc       210
Leu Lys Ser Leu Ala Lys Arg Ile Tyr Glu Ala Tyr Leu Lys Asn Phe
             30                  35                  40 aac atg aac aag gtc aaa gcc cgg gtc atc ctc tca gga aag gcc agt       258
Asn Met Asn Lys Val Lys Ala Arg Val Ile Leu Ser Gly Lys Ala Ser
         45                  50                  55 aac aat cca cct ttt gtc ata cat gat atg gag aca ctg tgt atg gct       306
Asn Asn Pro Pro Phe Val Ile His Asp Met Glu Thr Leu Cys Met Ala
     60                  65                  70 gag aag acg ctg gtg gcc aag ctg gtg gcc aat ggc atc cag aac aag       354
Glu Lys Thr Leu Val Ala Lys Leu Val Ala Asn Gly Ile Gln Asn Lys
 75                  80                  85 gag gcg gag gtc cgc atc ttt cac tgc tgc cag tgc acg tca gtg gag       402
Glu Ala Glu Val Arg Ile Phe His Cys Cys Gln Cys Thr Ser Val Glu
             90                  95                 100                 105 acc gtc acg gag ctc acg gaa ttc gcc aag gcc atc cca ggc ttc gca       450
Thr Val Thr Glu Leu Thr Glu Phe Ala Lys Ala Ile Pro Gly Phe Ala
                110                 115                 120 aac ttg gac ctg aac gat caa gtg aca ttg cta aaa tac gga gtt tat       498
Asn Leu Asp Leu Asn Asp Gln Val Thr Leu Leu Lys Tyr Gly Val Tyr
            125                 130                 135 gag gcc ata ttc gcc atg ctg tct tct gtg atg aac aaa gac ggg atg       546
Glu Ala Ile Phe Ala Met Leu Ser Ser Val Met Asn Lys Asp Gly Met
        140                 145                 150 ctg gta gcg tat gga aat ggg ttt ata act cgt gaa ttc cta aaa agc       594
Leu Val Ala Tyr Gly Asn Gly Phe Ile Thr Arg Glu Phe Leu Lys Ser
    155                 160                 165 cta agg aaa ccg ttc tgt gat atc atg gaa ccc aag ttt gat ttt gcc       642
Leu Arg Lys Pro Phe Cys Asp Ile Met Glu Pro Lys Phe Asp Phe Ala
```

-continued

```
                170                 175                 180                 185
atg aag ttc aat gca ctg gaa ctg gat gac agt gat atc tcc ctt ttt        690
Met Lys Phe Asn Ala Leu Glu Leu Asp Asp Ser Asp Ile Ser Leu Phe
            190                 195                 200 gtg gct gct atc att tgc tgt gga gat cgt cct ggc ctt cta aac gta        738
Val Ala Ala Ile Ile Cys Cys Gly Asp Arg Pro Gly Leu Leu Asn Val
        205                 210                 215 gga cac att gaa aaa atg cag gag ggt att gta cat gtg ctc aga ctc        786
Gly His Ile Glu Lys Met Gln Glu Gly Ile Val His Val Leu Arg Leu
    220                 225                 230 cac ctg cag agc aac cac ccg gac gat atc ttt ctc ttc cca aaa ctt        834
His Leu Gln Ser Asn His Pro Asp Asp Ile Phe Leu Phe Pro Lys Leu
235                 240                 245 ctt caa aaa atg gca gac ctc cgg cag ctg gtg acg gag cat gcg cag        882
Leu Gln Lys Met Ala Asp Leu Arg Gln Leu Val Thr Glu His Ala Gln
250                 255                 260                 265 ctg gtg cag atc atc aag aag acg gag tcg gat gct gcg ctg cac ccg        930
Leu Val Gln Ile Ile Lys Lys Thr Glu Ser Asp Ala Ala Leu His Pro
            270                 275                 280 cta ctg cag gag atc tac agg gac atg tac tgagtcgaca agcttgcggc         980
Leu Leu Gln Glu Ile Tyr Arg Asp Met Tyr
        285                 290 cgcactcgag caccaccacc accaccactg agat                                 1014
```

<210> SEQ ID NO 2
<211> LENGTH: 291
<212> TYPE: PRT
<213> ORGANISM: Artificial Sequence
<220> FEATURE:
<223> OTHER INFORMATION: Description of Artificial Sequence: Synthetic
    peptide construct

<400> SEQUENCE: 2

```
Met Gly Ser Ser His His His His His Ser Ser Gly Leu Val Pro
 1               5                  10                  15

Arg Gly Ser His Met Glu Thr Ala Asp Leu Lys Ser Leu Ala Lys Arg
                20                  25                  30

Ile Tyr Glu Ala Tyr Leu Lys Asn Phe Asn Met Asn Lys Val Lys Ala
            35                  40                  45

Arg Val Ile Leu Ser Gly Lys Ala Ser Asn Asn Pro Pro Phe Val Ile
        50                  55                  60

His Asp Met Glu Thr Leu Cys Met Ala Glu Lys Thr Leu Val Ala Lys
    65                  70                  75                  80

Leu Val Ala Asn Gly Ile Gln Asn Lys Glu Ala Glu Val Arg Ile Phe
                85                  90                  95

His Cys Cys Gln Cys Thr Ser Val Glu Thr Val Thr Glu Leu Thr Glu
            100                 105                 110

Phe Ala Lys Ala Ile Pro Gly Phe Ala Asn Leu Asp Leu Asn Asp Gln
        115                 120                 125

Val Thr Leu Leu Lys Tyr Gly Val Tyr Glu Ala Ile Phe Ala Met Leu
    130                 135                 140

Ser Ser Val Met Asn Lys Asp Gly Met Leu Val Ala Tyr Gly Asn Gly
145                 150                 155                 160

Phe Ile Thr Arg Glu Phe Leu Lys Ser Leu Arg Lys Pro Phe Cys Asp
                165                 170                 175

Ile Met Glu Pro Lys Phe Asp Phe Ala Met Lys Phe Asn Ala Leu Glu
            180                 185                 190
```

```
Leu Asp Asp Ser Asp Ile Ser Leu Phe Val Ala Ala Ile Ile Cys Cys
        195                 200                 205

Gly Asp Arg Pro Gly Leu Leu Asn Val Gly His Ile Glu Lys Met Gln
    210                 215                 220

Glu Gly Ile Val His Val Leu Arg Leu His Leu Gln Ser Asn His Pro
225                 230                 235                 240

Asp Asp Ile Phe Leu Phe Pro Lys Leu Leu Gln Lys Met Ala Asp Leu
                245                 250                 255

Arg Gln Leu Val Thr Glu His Ala Gln Leu Val Gln Ile Ile Lys Lys
            260                 265                 270

Thr Glu Ser Asp Ala Ala Leu His Pro Leu Leu Gln Glu Ile Tyr Arg
        275                 280                 285

Asp Met Tyr
    290

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctgacacat atggaaactg cagatctcaa atc                              33

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtgactgtcg actcagtaca tgtccctgta ga                               32

<210> SEQ ID NO 5
<211> LENGTH: 1017
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: CDS
<222> LOCATION: (88)..(963)

<400> SEQUENCE: 5
taatacgact cactataggg gaattgtgag cggataacaa ttcccctcta gaaataattt    60
tgtttaactt taagaaggag atatacc atg ggc agc agc cat cat cat cat cat   114
                               Met Gly Ser Ser His His His His His
                                 1               5 cac agc agc ggc ctg gtg ccg cgc ggc agc cat atg gag tcc gct gac    162
His Ser Ser Gly Leu Val Pro Arg Gly Ser His Met Glu Ser Ala Asp
 10                  15                  20                  25 ctc cgg gcc ctg gca aaa cat ttg tat gac tca tac ata aag tcc ttc    210
Leu Arg Ala Leu Ala Lys His Leu Tyr Asp Ser Tyr Ile Lys Ser Phe
                 30                  35                  40 ccg ctg acc aaa gca aag gcg agg gcg atc ttg aca gga aag aca aca    258
Pro Leu Thr Lys Ala Lys Ala Arg Ala Ile Leu Thr Gly Lys Thr Thr
             45                  50                  55
```

```
gac aaa tca cca ttc gtt atc tat gac atg aat tcc tta atg atg gga      306
Asp Lys Ser Pro Phe Val Ile Tyr Asp Met Asn Ser Leu Met Met Gly
        60                  65                  70 gaa gat aaa atc aag ttc aaa cac atc acc ccc ctg cag gag cag agc      354
Glu Asp Lys Ile Lys Phe Lys His Ile Thr Pro Leu Gln Glu Gln Ser
75                  80                  85 aaa gag gtg gcc atc cgc atc ttt cag ggc tgc cag ttt cgc tcc gtg      402
Lys Glu Val Ala Ile Arg Ile Phe Gln Gly Cys Gln Phe Arg Ser Val
 90                  95                 100                 105 gag gct gtg cag gag atc aca gag tat gcc aaa agc att cct ggt ttt      450
Glu Ala Val Gln Glu Ile Thr Glu Tyr Ala Lys Ser Ile Pro Gly Phe
                110                 115                 120 gta aat ctt gac ttg aac gac caa gta act ctc ctc aaa tat gga gtc      498
Val Asn Leu Asp Leu Asn Asp Gln Val Thr Leu Leu Lys Tyr Gly Val
            125                 130                 135 cac gag atc att tac aca atg ctg gcc tcc ttg atg aat aaa gat ggg      546
His Glu Ile Ile Tyr Thr Met Leu Ala Ser Leu Met Asn Lys Asp Gly
        140                 145                 150 gtt ctc ata tcc gag ggc caa ggc ttc atg aca agg gag ttt cta aag      594
Val Leu Ile Ser Glu Gly Gln Gly Phe Met Thr Arg Glu Phe Leu Lys
    155                 160                 165 agc ctg cga aag cct ttt ggt gac ttt atg gag ccc aag ttt gag ttt      642
Ser Leu Arg Lys Pro Phe Gly Asp Phe Met Glu Pro Lys Phe Glu Phe
170                 175                 180                 185 gct gtg aag ttc aat gca ctg gaa tta gat gac agc gac ttg gca ata      690
Ala Val Lys Phe Asn Ala Leu Glu Leu Asp Asp Ser Asp Leu Ala Ile
                190                 195                 200 ttt att gct gtc att att ctc agt gga gac cgc cca ggt ttg ctg aat      738
Phe Ile Ala Val Ile Ile Leu Ser Gly Asp Arg Pro Gly Leu Leu Asn
            205                 210                 215 gtg aag ccc att gaa gac att caa gac aac ctg cta caa gcc ctg gag      786
Val Lys Pro Ile Glu Asp Ile Gln Asp Asn Leu Leu Gln Ala Leu Glu
        220                 225                 230 ctc cag ctg aag ctg aac cac cct gag tcc tca cag ctg ttt gcc aag      834
Leu Gln Leu Lys Leu Asn His Pro Glu Ser Ser Gln Leu Phe Ala Lys
    235                 240                 245 ctg ctc cag aaa atg aca gac ctc aga cag att gtc acg gaa cat gtg      882
Leu Leu Gln Lys Met Thr Asp Leu Arg Gln Ile Val Thr Glu His Val
250                 255                 260                 265 cag cta ctg cag gtg atc aag aag acg gag aca gac atg agt ctt cac      930
Gln Leu Leu Gln Val Ile Lys Lys Thr Glu Thr Asp Met Ser Leu His
                270                 275                 280 ccg ctc ctg cag gag atc tac aag gac ttg tac taggtcgaca agcttgcggc    983
Pro Leu Leu Gln Glu Ile Tyr Lys Asp Leu Tyr
            285                 290 cgcactcgag caccaccacc accaccactg agat                                1017

<210> SEQ ID NO 6
<211> LENGTH: 292
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 6

Met Gly Ser Ser His His His His His His Ser Ser Gly Leu Val Pro
 1               5                  10                  15

Arg Gly Ser His Met Glu Ser Ala Asp Leu Arg Ala Leu Ala Lys His
            20                  25                  30
```

```
Leu Tyr Asp Ser Tyr Ile Lys Ser Phe Pro Leu Thr Lys Ala Lys Ala
        35                  40                  45

Arg Ala Ile Leu Thr Gly Lys Thr Thr Asp Lys Ser Pro Phe Val Ile
 50                  55                  60

Tyr Asp Met Asn Ser Leu Met Met Gly Glu Asp Lys Ile Lys Phe Lys
 65                  70                  75                  80

His Ile Thr Pro Leu Gln Glu Gln Ser Lys Glu Val Ala Ile Arg Ile
                 85                  90                  95

Phe Gln Gly Cys Gln Phe Arg Ser Val Glu Ala Val Gln Glu Ile Thr
                100                 105                 110

Glu Tyr Ala Lys Ser Ile Pro Gly Phe Val Asn Leu Asp Leu Asn Asp
            115                 120                 125

Gln Val Thr Leu Leu Lys Tyr Gly Val His Glu Ile Ile Tyr Thr Met
        130                 135                 140

Leu Ala Ser Leu Met Asn Lys Asp Gly Val Leu Ile Ser Glu Gly Gln
145                 150                 155                 160

Gly Phe Met Thr Arg Glu Phe Leu Lys Ser Leu Arg Lys Pro Phe Gly
                165                 170                 175

Asp Phe Met Glu Pro Lys Phe Glu Phe Ala Val Lys Phe Asn Ala Leu
            180                 185                 190

Glu Leu Asp Asp Ser Asp Leu Ala Ile Phe Ile Ala Val Ile Ile Leu
        195                 200                 205

Ser Gly Asp Arg Pro Gly Leu Leu Asn Val Lys Pro Ile Glu Asp Ile
210                 215                 220

Gln Asp Asn Leu Leu Gln Ala Leu Glu Leu Gln Leu Lys Leu Asn His
225                 230                 235                 240

Pro Glu Ser Ser Gln Leu Phe Ala Lys Leu Leu Gln Lys Met Thr Asp
                245                 250                 255

Leu Arg Gln Ile Val Thr Glu His Val Gln Leu Leu Gln Val Ile Lys
            260                 265                 270

Lys Thr Glu Thr Asp Met Ser Leu His Pro Leu Leu Gln Glu Ile Tyr
        275                 280                 285

Lys Asp Leu Tyr
        290

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gctcagacat atggagtccg ctgacctccg ggc                                33

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtgactgtcg acctagtaca agtccttgta ga                                 32

<210> SEQ ID NO 9
```

```
<211> LENGTH: 1089
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: CDS
<222> LOCATION: (88)..(948)

<400> SEQUENCE: 9
taatacgact cactataggg gaattgtgag cggataacaa ttcccctcta gaaataattt       60
tgtttaactt taagaaggag atatacc atg aaa aaa ggt cac cac cat cac cat      114
                               Met Lys Lys Gly His His His His His
                                 1               5 cac gga tcc cag tac aac cca cag gtg gcc gac ctg aag gcc ttc tcc        162
His Gly Ser Gln Tyr Asn Pro Gln Val Ala Asp Leu Lys Ala Phe Ser
 10              15                  20                  25 aag cac atc tac aat gcc tac ctg aaa aac ttc aac atg acc aaa aag        210
Lys His Ile Tyr Asn Ala Tyr Leu Lys Asn Phe Asn Met Thr Lys Lys
                 30                  35                  40 aag gcc cgc agc atc ctc acc ggc aaa gcc agc cac acg gcg ccc ttt        258
Lys Ala Arg Ser Ile Leu Thr Gly Lys Ala Ser His Thr Ala Pro Phe
             45                  50                  55 gtg atc cac gac atc gag aca ttg tgg cag gca gag aag ggg ctg gtg        306
Val Ile His Asp Ile Glu Thr Leu Trp Gln Ala Glu Lys Gly Leu Val
         60                  65                  70 tgg aag cag ttg gtg aat ggc ctg cct ccc tac aag gag atc agc gtg        354
Trp Lys Gln Leu Val Asn Gly Leu Pro Pro Tyr Lys Glu Ile Ser Val
     75                  80                  85 cac gtc ttc tac cgc tgc cag tgc acc aca gtg gag acc gtg cgg gag        402
His Val Phe Tyr Arg Cys Gln Cys Thr Thr Val Glu Thr Val Arg Glu
 90                  95                 100                 105 ctc act gag ttc gcc aag agc atc ccc agc ttc agc agc ctc ttc ctc        450
Leu Thr Glu Phe Ala Lys Ser Ile Pro Ser Phe Ser Ser Leu Phe Leu
                110                 115                 120 aac gac cag gtt acc ctt ctc aag tat ggc gtg cac gag gcc atc ttc        498
Asn Asp Gln Val Thr Leu Leu Lys Tyr Gly Val His Glu Ala Ile Phe
            125                 130                 135 gcc atg ctg gcc tct atc gtc aac aag gac ggg ctg ctg gta gcc aac        546
Ala Met Leu Ala Ser Ile Val Asn Lys Asp Gly Leu Leu Val Ala Asn
        140                 145                 150 ggc agt ggc ttt gtc acc cgt gag ttc ctg cgc agc ctc cgc aaa ccc        594
Gly Ser Gly Phe Val Thr Arg Glu Phe Leu Arg Ser Leu Arg Lys Pro
    155                 160                 165 ttc agt gat atc att gag cct aag ttt gaa ttt gct gtc aag ttc aac        642
Phe Ser Asp Ile Ile Glu Pro Lys Phe Glu Phe Ala Val Lys Phe Asn
170                 175                 180                 185 gcc ctg gaa ctt gat gac agt gac ctg gcc cta ttc att gcg gcc atc        690
Ala Leu Glu Leu Asp Asp Ser Asp Leu Ala Leu Phe Ile Ala Ala Ile
                190                 195                 200 att ctg tgt gga gac cgg cca ggc ctc atg aac gtt cca cgg gtg gag        738
Ile Leu Cys Gly Asp Arg Pro Gly Leu Met Asn Val Pro Arg Val Glu
            205                 210                 215 gct atc cag gac acc atc ctg cgt gcc ctc gaa ttc cac ctg cag gcc        786
Ala Ile Gln Asp Thr Ile Leu Arg Ala Leu Glu Phe His Leu Gln Ala
        220                 225                 230 aac cac cct gat gcc cag tac ctc ttc ccc aag ctg ctg cag aag atg        834
Asn His Pro Asp Ala Gln Tyr Leu Phe Pro Lys Leu Leu Gln Lys Met
    235                 240                 245 gct gac ctg cgg caa ctg gtc acc gag cac gcc cag atg atg cag cgg        882
Ala Asp Leu Arg Gln Leu Val Thr Glu His Ala Gln Met Met Gln Arg
```

```
Ala Asp Leu Arg Gln Leu Val Thr Glu His Ala Gln Met Met Gln Arg
250                 255                 260                 265 atc aag aag acc gaa acc gag acc tcg ctg cac cct ctg ctc cag gag      930
Ile Lys Lys Thr Glu Thr Glu Thr Ser Leu His Pro Leu Leu Gln Glu
                270                 275                 280 atc tac aag gac atg tac taagtcgacc accaccacca ccaccactga             978
Ile Tyr Lys Asp Met Tyr
                285 gatccggctg gccctactgg ccgaaaggaa ttcgaggcca gcagggccac cgctgagcaa    1038 taactagcat aaccccttgg ggcctctaaa cgggtcttga ggggttttttt g            1089

<210> SEQ ID NO 10
<211> LENGTH: 287
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 10

Met Lys Lys Gly His His His His His Gly Ser Gln Tyr Asn Pro
1               5                   10                  15

Gln Val Ala Asp Leu Lys Ala Phe Ser Lys His Ile Tyr Asn Ala Tyr
                20                  25                  30

Leu Lys Asn Phe Asn Met Thr Lys Lys Lys Ala Arg Ser Ile Leu Thr
            35                  40                  45

Gly Lys Ala Ser His Thr Ala Pro Phe Val Ile His Asp Ile Glu Thr
    50                  55                  60

Leu Trp Gln Ala Glu Lys Gly Leu Val Trp Lys Gln Leu Val Asn Gly
65                  70                  75                  80

Leu Pro Pro Tyr Lys Glu Ile Ser Val His Val Phe Tyr Arg Cys Gln
                85                  90                  95

Cys Thr Thr Val Glu Thr Val Arg Glu Leu Thr Glu Phe Ala Lys Ser
                100                 105                 110

Ile Pro Ser Phe Ser Ser Leu Phe Leu Asn Asp Gln Val Thr Leu Leu
            115                 120                 125

Lys Tyr Gly Val His Glu Ala Ile Phe Ala Met Leu Ala Ser Ile Val
    130                 135                 140

Asn Lys Asp Gly Leu Leu Val Ala Asn Gly Ser Gly Phe Val Thr Arg
145                 150                 155                 160

Glu Phe Leu Arg Ser Leu Arg Lys Pro Phe Ser Asp Ile Ile Glu Pro
                165                 170                 175

Lys Phe Glu Phe Ala Val Lys Phe Asn Ala Leu Glu Leu Asp Asp Ser
            180                 185                 190

Asp Leu Ala Leu Phe Ile Ala Ala Ile Ile Leu Cys Gly Asp Arg Pro
    195                 200                 205

Gly Leu Met Asn Val Pro Arg Val Glu Ala Ile Gln Asp Thr Ile Leu
210                 215                 220

Arg Ala Leu Glu Phe His Leu Gln Ala Asn His Pro Asp Ala Gln Tyr
225                 230                 235                 240

Leu Phe Pro Lys Leu Leu Gln Lys Met Ala Asp Leu Arg Gln Leu Val
                245                 250                 255

Thr Glu His Ala Gln Met Met Gln Arg Ile Lys Lys Thr Glu Thr Glu
            260                 265                 270

Thr Ser Leu His Pro Leu Leu Gln Glu Ile Tyr Lys Asp Met Tyr
    275                 280                 285
```

```
<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gttggatccc agtacaaccc acaggtggc                                    29

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtgactgtcg acttagtaca tgtccttgta ga                                32

<210> SEQ ID NO 13
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Gly Thr Pro Pro Gln Glu Ala Glu Glu Pro Ser Leu Leu Lys
  1               5                  10                  15

Lys Leu Leu Leu Ala Pro Ala Asn Thr
             20                  25
```

PPAR ACTIVE COMPOUNDS

CROSS-REFERENCE TO RELATED PATENT APPLICATIONS

This application claims the benefit of U.S. Provisional App. No. 60/631,746, filed Nov. 30, 2004, and U.S. Provisional App. No. 60/715,312, filed Sep. 7, 2005, both entitled PPAR Active Compounds, and both of which are incorporated herein by reference in their entireties and for all purposes.

BACKGROUND OF THE INVENTION

The present invention relates to the field of modulators for the family of nuclear receptors identified as peroxisome proliferator-activated receptors.

The following description is provided solely to assist the understanding of the reader. None of the references cited or information provided is admitted to be prior art to the present invention. Each of the references cited herein is incorporated by reference in its entirety, to the same extent as if each reference were individually indicated to be incorporated herein in its entirety.

The peroxisome proliferator-activated receptors (PPARs) form a subfamily in the nuclear receptor superfamily. Three isoforms, encoded by separate genes, have been identified thus far: PPARγ, PPARα, and PPARδ.

There are two PPARγ isoforms expressed at the protein level in mouse and human, γ1 and γ2. They differ only in that the latter has 30 additional amino acids at its N terminus due to differential promoter usage within the same gene, and subsequent alternative RNA processing. PPARγ2 is expressed primarily in adipose tissue, while PPARγ1 is expressed in a broad range of tissues.

Murine PPARα was the first member of this nuclear receptor subclass to be cloned; it has since been cloned from humans. PPARα is expressed in numerous metabolically active tissues, including liver, kidney, heart, skeletal muscle, and brown fat. It is also present in monocytes, vascular endothelium, and vascular smooth muscle cells. Activation of PPARα induces hepatic peroxisome proliferation, hepatomegaly, and hepatocarcinogenesis in rodents. These toxic effects are not observed in humans, although the same compounds activate PPARα across species.

Human PPARδ was cloned in the early 1990s and subsequently cloned from rodents. PPARδ is expressed in a wide range of tissues and cells with the highest levels of expression found in digestive tract, heart, kidney, liver, adipose, and brain. Thus far, no PPARδ-specific gene targets have been identified.

The PPARs are ligand-dependent transcription factors that regulate target gene expression by binding to specific peroxisome proliferator response elements (PPREs) in enhancer sites of regulated genes. PPARs possess a modular structure composed of functional domains that include a DNA binding domain (DBD) and a ligand binding domain (LBD). The DBD specifically binds PPREs in the regulatory region of PPAR-responsive genes. The DBD, located in the C-terminal half of the receptor, contains the ligand-dependent activation domain, AF-2. Each receptor binds to its PPRE as a heterodimer with a retinoid X receptor (RXR). Upon binding an agonist, the conformation of a PPAR is altered and stabilized such that a binding cleft, made up in part of the AF-2 domain, is created and recruitment of transcriptional coactivators occurs. Coactivators augment the ability of nuclear receptors to initiate the transcription process. The result of the agonist-induced PPAR-coactivator interaction at the PPRE is an increase in gene transcription. Downregulation of gene expression by PPARs appears to occur through indirect mechanisms. (Bergen & Wagner, 2002, *Diabetes Tech. & Ther.*, 4:163-174).

The first cloning of a PPAR (PPARα) occurred in the course of the search for the molecular target of rodent hepatic peroxisome proliferating agents. Since then, numerous fatty acids and their derivatives, including a variety of eicosanoids and prostaglandins, have been shown to serve as ligands of the PPARs. Thus, these receptors may play a central role in the sensing of nutrient levels and in the modulation of their metabolism. In addition, PPARs are the primary targets of selected classes of synthetic compounds that have been used in the successful treatment of diabetes and dyslipidemia. As such, an understanding of the molecular and physiological characteristics of these receptors has become extremely important to the development and utilization of drugs used to treat metabolic disorders.

Kota et al., 2005, *Pharmacological Research* 51: 85-94, provides a review of biological mechanisms involving PPARs that includes a discussion of the possibility of using PPAR modulators for treating a variety of conditions, including chronic inflammatory disorders such as atherosclerosis, arthritis and inflammatory bowel syndrome, retinal disorders associated with angiogenesis, increased fertility, and neurodegenerative diseases.

Yousef et al., 2004, *Journal of Biomedicine and Biotechnology* 2004(3):156-166, discusses the anti-inflammatory effects of PPAR α, γ and δ agonists, suggesting that PPAR agonists may have a role in treating neuronal diseases such as Alzheimer's disease, and autoimmune diseases such as inflammatory bowel disease and multiple sclerosis. A potential role for PPAR agonists in the treatment of Alzheimer's disease has been described in Combs et al., 2000, *Journal of Neuroscience* 20(2): 558, and such a role for PPAR agonists in Parkinson's disease is discussed in Breidert et al. 2002, *Journal of Neurochemistry*, 82: 615. A potential related function of PPAR agonists in treatment of Alzheimer's disease, that of regulation of the APP-processing enzyme BACE, has been discussed in Sastre et al. 2003, *Journal of Neuroscience* 23(30):9796. These studies collectively indicate PPAR agonists may provide advantages in treating a variety of neurodegenerative diseases by acting through complementary mechanisms.

Discussion of the anti-inflammatory effects of PPAR agonists is also available in Feinstein, 2004, *Drug Discovery Today. Therapeutic Strategies* 1(1):29-34 in relation to multiple sclerosis and Alzheimer's disease; Patel et al., 2003, *The Journal of Immunology*, 170:2663-2669 in relation to chronic obstructive pulmonary disease (COPD) and asthma; Lovett-Racke et al., 2004, *The Journal of Immunology*, 172:5790-5798 in relation to autoimmune disease; Malhotra et al., 2005, *Expert Opinions in Pharmacotherapy*, 6(9):1455-1461 in relation to psoriasis; and Storer et al., 2005, *Journal of Neuroimmunology*, 161:113-122 in relation to multiple sclerosis.

This wide range of roles for the PPARs that have been discovered suggest that PPARα, PPARγ and PPARδ may play a role in a wide range of events involving the vasculature, including atherosclerotic plaque formation and stability, thrombosis, vascular tone, angiogenesis, cancer, pregnancy, pulmonary disease, autoimmune disease, and neurological disorders.

Among the synthetic ligands identified for PPARs are Thiazolidinediones (TZDs). These compounds were originally developed on the basis of their insulin-sensitizing effects in animal pharmacology studies. Subsequently, it was found that TZDs induced adipocyte differentiation and increased expression of adipocyte genes, including the adipocyte fatty acid-binding protein aP2. Independently, it was discovered that PPARγ interacted with a regulatory element of the aP2 gene that controlled its adipocyte-specific expression. On the basis of these seminal observations, experiments were performed that determined that TZDs were PPARγ ligands and agonists and demonstrate a definite correlation between their in vitro PPARγ activities and their in vivo insulin-sensitizing actions. (Bergen & Wagner, supra).

Several TZDs, including troglitazone, rosiglitazone, and pioglitazone, have insulin-sensitizing and anti-diabetic activity in humans with type 2 diabetes and impaired glucose tolerance. Farglitazar is a very potent non-TZD PPAR-γ-selective agonist that was recently shown to have antidiabetic as well as lipid-altering efficacy in humans. In addition to these potent PPARγ ligands, a subset of the non-steroidal antiinflammatory drugs (NSAIDs), including indomethacin, fenoprofen, and ibuprofen, have displayed weak PPARγ and PPARα activities. (Bergen & Wagner, supra).

The fibrates, amphipathic carboxylic acids that have been proven useful in the treatment of hypertriglyceridemia, are PPARα ligands. The prototypical member of this compound class, clofibrate, was developed prior to the identification of PPARs, using in vivo assays in rodents to assess lipid-lowering efficacy. (Bergen & Wagner, supra).

Fu et al., Nature, 2003, 425:9093, demonstrated that the PPARα binding compound, oleylethanolamide, produces satiety and reduces body weight gain in mice.

Clofibrate and fenofibrate have been shown to activate PPARα with a 10-fold selectivity over PPARγ. Bezafibrate acted as a pan-agonist that showed similar potency on all three PPAR isoforms. Wy-14643, the 2-arylthioacetic acid analogue of clofibrate, was a potent murine PPARα agonist as well as a weak PPARγ agonist. In humans, all of the fibrates must be used at high doses (200-1,200 mg/day) to achieve efficacious lipid-lowering activity.

TZDs and non-TZDs have also been identified that are dual PPARγ/α agonists. By virtue of the additional PPARα agonist activity, this class of compounds has potent lipid-altering efficacy in addition to antihyperglycemic activity in animal models of diabetes and lipid disorders. KRP-297 is an example of a TZD dual PPARγ/α agonist (Fajas, J. Biol. Chem., 1997, 272:18779-18789); furthermore, DRF-2725 and AZ-242 are non-TZD dual PPARγ/α agonists. (Lohray, et al., J. Med. Chem., 2001, 44:2675-2678; Cronet, et al., Structure (Camb.), 2001, 9:699-706).

In order to define the physiological role of PPARδ, efforts have been made to develop novel compounds that activate this receptor in a selective manner. Amongst the α-substituted carboxylic acids previously described, the potent PPARδ ligand L-165041 demonstrated approximately 30-fold agonist selectivity for this receptor over PPARγ; it was inactive on murine PPARα (Liebowitz, et al., FEBS Lett., 2000, 473:333-336). This compound was found to increase high-density lipoprotein levels in rodents. It was also reported that GW501516 was a potent, highly-selective PPARδ agonist that produced beneficial changes in serum lipid parameters in obese, insulin-resistant rhesus monkeys. (Oliver et al., Proc. Natl. Acad. Sci., 2001, 98:5306-5311).

In addition to the compounds discussed above, certain thiazole derivatives active on PPARs have been described. (Cadilla et al., Internat. Appl. PCT/US01/149320, Internat. Publ. WO 02/062774, incorporated herein by reference in its entirety.)

Some tricyclic-α-alkyloxyphenylpropionic acids were described as dual PPARα/γ agonists in Sauerberg et al., J. Med. Chem. 2002, 45:789-804.

A group of compounds that were stated to have equal activity on PPARα/γ/δ was described in Morgensen et al., Bioorg. & Med. Chem. Lett. 2002, 13:257-260.

Oliver et al., described a selective PPARδ agonist that promotes reverse cholesterol transport. (Oliver et al., supra.)

Yamamoto et al., U.S. Pat. No. 3,489,767 describes 1-(phenylsulfonyl)-indolyl aliphatic acid derivatives that are stated to have "antiphlogistic, analgesic and antipyretic actions." (Col. 1, lines 16-19.)

Kato et al., European patent application 94101551.3, Publication No. 0 610 793 A1, describes the use of 3-(5-methoxy-1-p-toluenesulfonylindol-3-yl)propionic acid (page 6) and 1-(2,3,6-triisopropylphenylsulfonyl)-indole-3-propionic acid (page 9) as intermediates in the synthesis of particular tetracyclic morpholine derivatives useful as analgesics.

Accordingly, there is a need for safer, more effective PPAR agonists for the treatment of a variety of diseases, including PPARα, PPARγ or PPARδ selective agonists as well agonists selective for any two or all three of PPARα, PPARγ and PPARδ.

This application incorporates herein by reference and for all purposes the entire disclosures of each of the following applications: U.S. application Ser. No. 10/937,791, filed Sep. 8, 2004, U.S. application Ser. No. 10/893,134, filed Jul. 16, 2004, U.S. Provisional App. No. 60/488,523, filed Jul. 17, 2003, U.S. Provisional App. No. 60/552,994, filed Mar. 12, 2004, U.S. Provisional App. No. 60/631,893, filed Nov. 11, 2004, and U.S. Provisional App. No. 60/715,258, filed Sep. 7, 2005, all entitled PPAR Active Compounds.

SUMMARY OF THE INVENTION

The present invention involves compounds active on PPARs, which are useful for therapeutic and/or prophylactic methods involving modulation of at least one of PPARα, PPARδ, and PPARγ. Included are compounds that have pan-activity across the PPAR family (i.e., PPARα, PPARδ, and PPARγ), as well as compounds that have significant specificity (at least 5-, 10-, 20-, 50-, or 100-fold greater activity) on a single PPAR, or on two of the three PPARs.

In one aspect, the invention provides compounds of Formula I as follows:

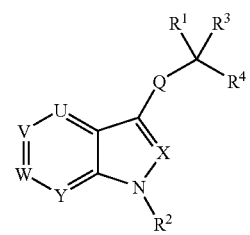

Formula I wherein:
U, V, W, X, and Y are independently N or $CR^5$, wherein at most two of U, V, W, and Y are N, and preferably no more than two of U, V, W, X, and Y are N;
Q is —O—, —S—, or —$NR^{51}$—;
$R^1$ is selected from the group consisting of optionally substituted carboxyl and a carboxylic acid isostere;
$R^2$ is selected from the group consisting of hydrogen, optionally substituted lower alkyl, optionally substituted lower alkenyl, optionally substituted lower alkynyl, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, —C(Z)NR$^6$R$^7$, —C(Z)R$^8$, —S(O)$_2$NR$^6$R$^7$, and —S(O)$_2$R$^9$;

R$^3$ and R$^4$ are independently selected from the group consisting of hydrogen, optionally substituted lower alkyl, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl, or R$^3$ and R$^4$ may combine to form a 3-7 membered optionally substituted mono-cycloalkyl or 3-7 membered optionally substituted mono-heterocycloalkyl;

R$^5$ at each occurrence is independently selected from the group consisting of hydrogen, halo, optionally substituted lower alkyl, optionally substituted lower alkenyl, optionally substituted lower alkynyl, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, —OR$^{10}$, —SR$^{11}$, —NR$^{12}$R$^{13}$, —C(Z)NR$^6$R$^7$, —C(Z)R$^8$, —S(O)$_2$NR$^6$R$^7$, and —S(O)$_n$R$^9$;

R$^6$ and R$^7$ at each occurrence are independently selected from the group consisting of hydrogen, optionally substituted lower alkyl, optionally substituted lower alkenyl, provided, however, that when R$^6$ and/or R$^7$ are optionally substituted lower alkenyl, no alkene carbon thereof is bound to nitrogen, optionally substituted lower alkynyl, provided, however, that when R$^6$ and/or R$^7$ are optionally substituted lower alkynyl, no alkyne carbon thereof is bound to nitrogen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl, or R$^6$ and R$^7$ together with the nitrogen to which they are attached form a 5-7 membered optionally substituted heterocycloalkyl or 5-7 membered optionally substituted heteroaryl;

R$^8$ at each occurrence is independently selected from the group consisting of optionally substituted lower alkyl, optionally substituted lower alkenyl, provided, however, that when R$^8$ is optionally substituted lower alkenyl, no alkene carbon thereof is bound to —C(Z)-, optionally substituted lower alkynyl, provided, however, that when R$^8$ is optionally substituted lower alkynyl, no alkyne carbon thereof is bound to —C(Z)-, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, and —OR$^{11}$;

R$^9$ at each occurrence is independently selected from the group consisting of optionally substituted lower alkyl, optionally substituted lower alkenyl, provided, however, that when R$^9$ is optionally substituted lower alkenyl, no alkene carbon thereof is bound to —S(O)$_n$—, optionally substituted lower alkynyl, provided, however, that when R$^9$ is optionally substituted lower alkynyl, no alkyne carbon thereof is bound to —S(O)$_n$—, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl;

R$^{10}$ at each occurrence is independently selected from the group consisting of hydrogen, optionally substituted lower alkyl, optionally substituted lower alkenyl, provided, however, that when R$^{10}$ is optionally substituted lower alkenyl, no alkene carbon thereof is bound to oxygen, optionally substituted lower alkynyl, provided, however, that when R$^{10}$ is optionally substituted lower alkynyl, no alkyne carbon thereof is bound to oxygen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, —C(Z)R$^8$, and —C(Z)NR$^6$R$^7$;

R$^{11}$ at each occurrence is independently selected from the group consisting of hydrogen, optionally substituted lower alkyl, optionally substituted lower alkenyl, provided, however, that when R$^{11}$ is optionally substituted lower alkenyl, no alkene carbon thereof is bound to S or O, optionally substituted lower alkynyl, provided, however, that when R$^{11}$ is optionally substituted lower alkynyl, no alkyne carbon thereof is bound to S or O, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl;

R$^{12}$ and R$^{13}$ at each occurrence are independently selected from the group consisting of hydrogen, optionally substituted lower alkyl, optionally substituted lower alkenyl, provided, however, that when R$^{12}$ and/or R$^{13}$ are optionally substituted lower alkenyl, no alkene carbon thereof is bound to nitrogen, optionally substituted lower alkynyl, provided, however, that when R$^{12}$ and/or R$^{13}$ are optionally substituted lower alkynyl, no alkyne carbon thereof is bound to nitrogen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted-heteroaryl, optionally substituted heteroaralkyl, —C(Z)R$^8$, —C(Z)NR$^6$R$^7$, —S(O)$_2$R$^9$, and —S(O)$_2$NR$^6$R$^7$, or R$^{12}$ and R$^{13}$ together with the nitrogen to which they are attached form a 5-7 membered optionally substituted heterocycloalkyl or 5-7 membered optionally substituted heteroaryl;

R$^{51}$ is selected from the group consisting of hydrogen, optionally substituted lower alkyl, optionally substituted lower alkenyl, provided, however, that when R$^{51}$ is optionally substituted lower alkenyl, no alkene carbon thereof is bound to nitrogen, optionally substituted lower alkynyl, provided, however, that when R$^{51}$ is optionally substituted lower alkynyl, no alkyne carbon thereof is bound to nitrogen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, —C(Z)NR$^6$R$^7$, —C(Z)R$^8$, —S(O)$_2$NR$^6$R$^7$, and —S(O)$_2$R$^9$;

n is 1 or 2;

Z is O or S; and all salts, prodrugs, tautomers and stereoisomers thereof.

In one embodiment of compounds of Formula I, R$^5$ is selected from the group consisting of hydrogen, halo, optionally fluoro substituted lower alkyl, optionally fluoro substituted lower alkylthio, and optionally fluoro substituted lower alkoxy. In one embodiment, when Q is —NR$^{51}$—, then R$^{51}$ is hydrogen or optionally substituted lower alkyl, where lower alkyl is preferably optionally substituted with halo, hydroxyl, lower alkoxy, thiol, or lower alkylthio, provided that hydroxy, lower alkoxy, thiol, or lower alkylthio are not substituted at the carbon that is bound to the nitrogen of —NR$^{51}$—. In one embodiment, U, W, X and Y are CH, and V is CR$^5$. In one embodiment, U, W, X and Y are CH, and V is CR$^5$, where R$^5$ is selected from the group consisting of hydrogen, halo, optionally fluoro substituted lower alkyl, optionally fluoro substituted lower alkylthio, and optionally fluoro substituted lower alkoxy.

In certain embodiments involving compounds of Formula I, the compounds have a structure of Formula I in which the bicyclic core shown for Formula I has one of the following structures:

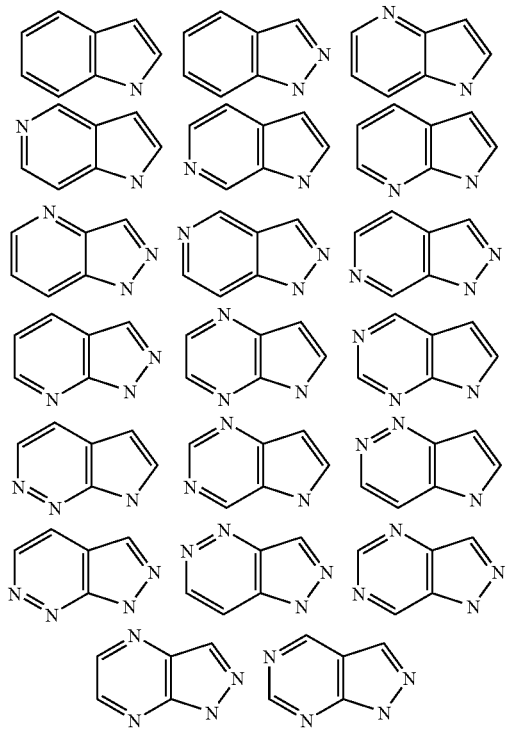

Thus, in particular embodiments involving compounds of Formula I, the compound includes a bicyclic core as shown above. Such compounds can include substitutents as described for Formula I, with the understanding that ring nitrogens other than the nitrogen corresponding to position 1 of the indole structure are unsubstituted. In particular embodiments, the compounds have one of the bicyclic cores shown above and substitution pattern as shown herein for compounds having an indolyl or other bicyclic core.

In certain embodiments, compounds of Formula I have a structure of Formula Ia as shown below:

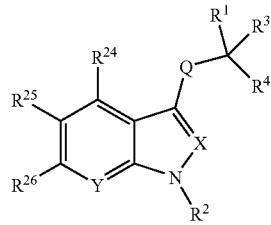

Formula Ia wherein:

X, Y, Q, R$^1$, R$^3$, and R$^4$ are as defined in Formula I above;

R$^2$ is selected from the group consisting of —CR$^{52}$R$^{53}$R$^{14}$, —C(Z)NR$^6$R$^7$, —C(Z)R$^8$, —S(O)$_2$NR$^6$R$^7$, and —S(O)$_2$R$^9$;

R$^{14}$ is selected from the group consisting of optionally substituted cycloalkyl, optionally substituted heterocycloalkyl, optionally substituted aryl and optionally substituted heteroaryl;

R$^{52}$ and R$^{53}$ are independently selected from the group consisting of hydrogen, halo, lower alkyl, hydroxyl, lower alkoxy, thiol, and lower alkylthio, wherein lower alkyl and the lower alkyl chains of lower alkoxy and lower alkylthio are optionally substituted with fluoro, hydroxyl, lower alkoxy, thiol, lower alkylthio or —NR$^{54}$R$^{55}$, provided, however, that the substitution of lower alkoxy or lower alkylthio does not result in O, N, or S bound to the carbon that is bound to the lower alkoxy oxygen or the lower alkylthio sulfur;

R$^{54}$ and R$^{55}$ are independently lower alkyl, or R$^{54}$ and R$^{55}$ combine with the nitrogen to which they are attached to form a 5-7 membered heterocycloalkyl or 5-7 membered heterocycloalkyl substituted with halo, hydroxyl, lower alkoxy, or lower alkyl;

R$^{24}$, R$^{25}$ and R$^{26}$ are independently selected from the group consisting of hydrogen, halo, optionally substituted lower alkyl, optionally substituted lower alkenyl, optionally substituted lower alkynyl, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, —OR$^{10}$, —SR$^{11}$, —NR$^{12}$R$^{13}$, —C(Z)NR$^6$R$^7$, —C(Z)R$^8$, —S(O)$_2$NR$^6$R$^7$, and —S(O)$_n$R$^9$;

n, Z, R$^6$, R$^7$, R$^8$, R$^9$, R$^{10}$, R$^{11}$, R$^{12}$, and R$^{13}$ are as defined for Formula I above; and all salts, prodrugs, tautomers and stereoisomers thereof.

In one embodiment of compounds of Formula Ia, R$^2$ is —S(O)$_2$R$^9$. In another embodiment, X and Y are CH, and R$^{24}$ and R$^{26}$ are hydrogen. In another embodiment, X and Y are CH, and R$^{24}$ and R$^{25}$ are hydrogen. In another embodiment, X and Y are CH, and R$^{25}$ and R$^{26}$ are hydrogen. In another embodiment, R$^{24}$, R$^{25}$, and R$^{26}$ are independently selected from the group consisting of hydrogen, halo, optionally fluoro substituted lower alkyl, optionally fluoro substituted lower alkylthio, and optionally fluoro substituted lower alkoxy. In another embodiment, X and Y are CH, R$^{24}$ and R$^{26}$ are hydrogen, and R$^{25}$ is selected from the group consisting of hydrogen, halo, optionally fluoro substituted lower alkyl, optionally fluoro substituted lower alkylthio, and optionally fluoro substituted lower alkoxy. In another embodiment, when Q is —NR$^{51}$—, R$^{51}$ is hydrogen or optionally substituted lower alkyl, where lower alkyl is preferably optionally substituted with halo, hydroxyl, lower alkoxy, thiol, or lower alkylthio, provided that hydroxy, alkoxy, thiol, or alkylthio are not substituted at the carbon that is bound to the nitrogen of —NR$^{51}$—.

In certain embodiments, compounds of Formula I have a structure of Formula Ib as shown below:

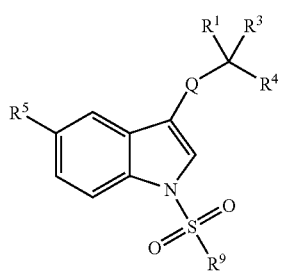

Formula Ib wherein n, R$^1$, R$^3$, R$^4$, R$^5$, R$^6$, R$^7$, R$^8$, R$^9$, R$^{10}$, R$^{11}$, R$^{12}$, R$^{13}$, Z, and Q are as defined in Formula I above. In one embodiment of compounds of Formula Ib, R$^5$ is selected from the group consisting of halo, optionally fluoro substituted lower alkyl, optionally fluoro substituted lower alkylthio, and optionally fluoro substituted lower alkoxy. In another embodiment, R$^3$ and R$^4$ are H, Q is O, and R$^5$ is selected from the group consisting of halo, optionally fluoro substituted lower alkyl, optionally fluoro substituted lower alkylthio, and optionally fluoro substituted lower alkoxy. In another embodiment, when Q is —O—, then R$^5$ is halo, preferably Br. In another embodiment, when Q is —S—, then R$^5$ is optionally fluoro substituted lower alkoxy, also lower alkoxy, preferably methoxy. In another embodiment, when Q is —NR$^{51}$—, then R$^{51}$ is hydrogen or optionally substituted lower alkyl, where lower alkyl is preferably optionally substituted with halo, hydroxyl, lower alkoxy, thiol, or lower alkylthio, provided that hydroxy, alkoxy, thiol, or alkylthio are not substituted at the carbon that is bound to the nitrogen of —NR$^{51}$—.

In certain embodiments, compounds of Formula I have a structure of Formula Ic as shown below:

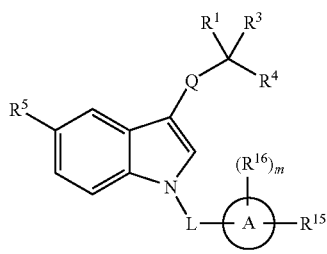

Formula Ic wherein:
R$^1$, R$^3$, R$^4$, R$^5$, and Q are as defined in Formula I above;
A is a monocyclic or bicyclic ring selected from the group consisting of cycloalkyl, heterocycloalkyl, aryl, and heteroaryl;

L is selected from the group consisting of —CR$^{52}$R$^{53}$—, —C(Z)NR$^{56}$—, —C(Z)-, —S(O)$_2$NR$^{56}$—; and —S(O)$_2$—, attached to A at any available atom to produce a stable compound;

R$^{52}$, R$^{53}$, R$^{54}$, and R$^{55}$ are as defined for Formula Ib above;

R$^{56}$ is selected from the group consisting of hydrogen, optionally substituted lower alkyl, optionally substituted lower alkenyl, provided, however, that when R$^{56}$ is optionally substituted lower alkenyl, no alkene carbon thereof is bound to nitrogen, optionally substituted lower alkynyl, provided, however, that when R$^{56}$ is optionally substituted lower alkynyl, no alkyne carbon thereof is bound to nitrogen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl;

R$^{15}$ is selected from the group consisting of hydrogen, halo, cyano, nitro, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —OR$^{10}$, —SR$^{11}$, —NR$^{12}$R$^{13}$, —C(Z)NR$^6$R$^7$, —C(Z)R$^8$, —S(O)$_2$ NR$^6$R$^7$, and —S(O)$_n$R$^9$, attached to A at any available atom to produce a stable compound;

n, Z, R$^6$, R$^7$, R$^8$, R$^9$, R$^{10}$, R$^{11}$, R$^{12}$, and R$^{13}$ are as defined in Formula I above;

R$^{16}$ at each occurrence is independently selected from the group consisting of halo, lower alkyl, hydroxyl, lower alkoxy, thiol, and lower alkylthio, wherein lower alkyl and the lower alkyl chains of lower alkoxy and lower alkylthio are optionally substituted with fluoro, hydroxyl, lower alkoxy, thiol, or lower alkylthio, provided, however, that any substitution on lower alkoxy or lower alkylthio does not result in O or S bound to the carbon that is bound to the alkoxy oxygen of substituted lower alkoxy or the alkylthio sulfur of substituted lower alkylthio;

m is 0, 1, or 2; and all salts, prodrugs, tautomers and stereoisomers thereof.

In one embodiment of compounds of Formula Ic, A is a monocyclic aryl or monocyclic heteroaryl. In one embodiment, A is a monocyclic heteroaryl. In one embodiment, R$^{15}$ is selected from the group consisting of optionally substituted cycloalkyl, optionally substituted heterocycloalkyl, optionally substituted aryl, optionally substituted heteroaryl, —OR$^{10}$, —SR$^{11}$, —NR$^{12}$R$^{13}$, —C(Z)NR$^6$R$^7$, —C(Z)R$^8$, —S(O)$_2$NR$^6$R$^7$, and —S(O)$_n$R$^9$, further wherein one of R$^6$ and R$^7$, one of R$^{12}$, and R$^{13}$, R$^8$, R$^9$, R$^{10}$ and R$^{11}$ are selected from the group consisting of optionally substituted cycloalkyl, optionally substituted heterocycloalkyl, optionally substituted aryl, and optionally substituted heteroaryl. In one embodiment, R$^5$ is selected from the group consisting of halo, optionally fluoro substituted lower alkyl, optionally fluoro substituted lower alkylthio, and optionally fluoro substituted lower alkoxy. In another embodiment, R$^3$ and R$^4$ are H, Q is O, and R$^5$ is selected from the group consisting of halo, optionally fluoro substituted lower alkyl, optionally fluoro substituted lower alkylthio, and optionally fluoro substituted lower alkoxy. In another embodiment, when Q is —O—, then R$^5$ is halo, preferably Br. In another embodiment, when Q is —S—, then R$^5$ is optionally fluoro substituted lower alkoxy, also lower alkoxy, preferably methoxy. In another embodiment, when Q is —NR$^{51}$—, then R$^{51}$ is hydrogen or optionally substituted lower alkyl, where lower alkyl is preferably optionally substituted with halo, hydroxyl, lower alkoxy, thiol, or lower alkylthio, provided that hydroxy, alkoxy, thiol, or alkylthio are not substituted at the carbon that is bound to the nitrogen of —NR$^{51}$—.

In specifying a compound or compounds of Formula I, Ia, Ib, or Ic, unless clearly indicated to the contrary, specification of such compound(s) includes pharmaceutically acceptable salts of the compound(s).

In certain embodiments of the above compounds, compounds are excluded where N, O, S or C(Z) would be bound to a carbon that is also bound to N, O, S, or C(Z) or is bound to an alkene carbon atom of an alkenyl group or bound to an alkyne atom of an alkynyl group. Accordingly, in certain embodiments compounds are excluded from the present invention in which there are included linkages such as —NR—CH$_2$—NR—, —O—CH$_2$—NR—, —S(O)$_{0-2}$—CH$_2$—NR—, —C(Z)-CH$_2$—NR—, —O—CH$_2$—O—, —S(O)$_{0-2}$—CH$_2$—O—, —C(Z)-CH$_2$—O—, —S(O)$_{0-2}$—CH$_2$—S(O)$_{0-2}$—, —C(Z)-CH$_2$—S(O)$_{0-2}$—, —C(Z)—CH$_2$—C(Z)-, —NR—CH═CH—, —NR—C≡C—, —O—CH═CH—, —O—C≡C—, —S(O)$_{0-2}$—CH═CH—, —S(O)$_{0-2}$—C≡C—, —C(Z)-CH═CH—, or —C(Z)-C≡C—.

Reference to compounds of Formula I, Ia, Ib, or Ic herein includes specific reference to sub-groups and species of compounds of Formula I, Ia, Ib, or Ic described herein (e.g., particular embodiments as described above) unless indicated to the contrary.

Another aspect of the invention concerns novel use of compounds of Formula I, Ia, Ib, or Ic for the treatment of diseases associated with PPARs. Another aspect of the invention concerns novel compounds of Formula I, Ia, Ib, or Ic.

Another aspect of this invention provides compositions that include a therapeutically effective amount of a compound of Formula I, Ia, Ib, or Ic and at least one pharmaceutically acceptable carrier, excipient, and/or diluent. The composition can include a plurality of different pharmacalogically active compounds, including one or more compounds of Formula I, Ia, Ib, or Ic. An "effective amount" of a compound or composition, as used herein, includes within its meaning a nontoxic but sufficient amount of the particular compound or composition to which it is referring to provide the desired therapeutic effect.

In another aspect, compounds of Formula I, Ia, Ib, or Ic can be used in the preparation of a medicament for the treatment of a PPAR-mediated disease or condition or a disease or condition in which modulation of a PPAR provides a therapeutic benefit.

In another aspect, the invention provides kits that include a composition as described herein. In particular embodiments, the composition is packaged, e.g., in a vial, bottle, flask, which may be further packaged, e.g., within a box, envelope, or bag; the composition is approved by the U.S. Food and Drug Administration or similar regulatory agency for administration to a mammal, e.g., a human; the composition is approved for administration to a mammal, e.g., a human, for a PPAR-mediated disease or condition; the kit includes written instructions or other indication that the composition is suitable or approved for administration to a mammal, e.g., a human, for a PPAR-mediated disease or condition; the composition is packaged in unit dose or single dose form, e.g., single dose pills, capsules, or the like.

In another aspect, the invention provides a method of treating or prophylaxis of a disease or condition in a mammal, e.g., a PPAR-mediated disease or condition or a disease or condition in which modulation of a PPAR provides a therapeutic benefit, by administering to the mammal a therapeutically effective amount of a compound of Formula I, Ia, Ib, or Ic, a prodrug of such compound, or a pharmaceutically acceptable salt of such compound or prodrug. The compound can be administered alone or can be part of a pharmaceutical composition.

In aspects and embodiments involving treatment or prophylaxis of a disease or condition, the disease or condition is selected from the group consisting of obesity, overweight condition, hyperlipidemia, dyslipidemia including associated diabetic dyslipidemia and mixed dyslipidemia, hypoalphalipoproteinemia, Syndrome X, Type II diabetes mellitus, Type I diabetes, hyperinsulinemia, impaired glucose tolerance, insulin resistance, a diabetic complication (e.g., neuropathy, nephropathy, retinopathy or cataracts), hypertension, coronary heart disease, heart failure, hypercholesterolemia, inflammation, thrombosis, congestive heart failure, cardiovascular disease (including atherosclerosis, arteriosclerosis, and hypertriglyceridemia), epithelial hyperproliferative diseases (such as-eczema and psoriasis), cancer, neuropathic or inflammatory pain, conditions associated with the lung and gut, regulation of appetite and food intake in subjects suffering from disorders such as obesity, anorexia bulimia and anorexia nervosa, neurodegenerative diseases, such as Alzheimer's disease, Parkinson's disease, and amyotrophic lateral sclerosis, autoimmune diseases such as Type-1 diabetes mellitus, vitiligo, uveitis, Sjogren's disease, pemphigus foliaceus, inclusion body myositis, polymyositis, dermatomyositis, scleroderma, Grave's disease, Hashimoto's disease, chronic graft-versus host disease, rheumatoid arthritis, inflammatory bowel syndrome, Crohn's disease and multiple sclerosis, pregnancy (e.g. fertility), diseases involving airway smooth muscle cells such as asthma and COPD, and angiogenesis related conditions, such as macular degeneration.

In certain embodiments of aspects involving compounds of Formula I, Ia, Ib, or Ic, the compound is specific for any one or any two of PPARα, PPARγ and PPARδ, e.g. specific for PPARα; specific for PPARδ; specific for PPARγ; specific for PPARα and PPARδ; specific for PPARα and PPARγ; specific for PPARδ and PPARγ. Such specificity means that the compound has at least 5-fold greater activity (preferably at least 5-, 10-, 20-, 50-, or 100-fold or more greater activity) on the specific PPAR(s) than on the other PPAR(s), where the activity is determined using a biochemical assay suitable for determining PPAR activity, e.g., any assay known to one skilled in the art or as described herein. In another embodiment, compounds have significant activity on all three of PPARα, PPARδ, and PPARγ.

In certain embodiments, a compound of the invention has an $EC_{50}$ of less than 100 nM, less than 50 nM, less than 20 nM, less than 10 nM, less than 5 nM, or less than 1 nM with respect to at least one of PPARα, PPARγ and PPARδ as determined in a generally accepted PPAR activity assay. In one embodiment, a compound of Formula I, Ia, Ib, or Ic will have an $EC_{50}$ of less than 100 nM, less than 50 nM, less than 20 nM, less than 10 nM, less than 5 nM, or less than 1 nM with respect to at least any two of PPARα, PPARγ and PPARδ. In one embodiment, a compound of Formula I, Ia, Ib, or Ic will have an $EC_{50}$ of less than 100 nM, less than 50 nM, less than 20 nM, less than 10 nM, less than 5 nM, or less than 1 nM with respect to all three of PPARα, PPARγ and PPARδ. Further to any of the above embodiments, a compound of the invention will be a specific agonist of any one of PPARα, PPARγ and PPARδ, or any two of PPARα, PPARγ and PPARδ. A specific agonist of one of PPARα, PPARγ and PPARδ is such that the $EC_{50}$ for one of PPARα, PPARγ and PPARδ will be at least about 5-fold, also 10-fold, also 20-fold, also 50-fold, or at least about 100-fold less than the $EC_{50}$ for the other two of PPARα, PPARγ and PPARδ. A specific agonist of two of PPARα, PPARγ and PPARδ is such that the $EC_{50}$ for each of two of PPARα, PPARγ and PPARδ will be at least about 5-fold, also 10-fold, also 20-fold, also 50-fold, or at least about 100-fold less than the $EC_{50}$ for the other of PPARα, PPARγ and PPARδ.

In certain embodiments of the invention, the compounds of Formula I, Ia, Ib, or Ic active on PPARs also have desireable pharmacologic properties. In particular embodiments the desired pharmacologic property is PPAR pan-activity, PPAR selectivity for any individual PPAR (PPARα, PPARδ, or PPARγ), selectivity on any two PPARs (PPARα and PPARδ, PPARα and PPARγ, or PPARδ and PPARγ), or any one or more of serum half-life longer than 2 hr, also longer than 4 hr, also longer than 8 hr, aqueous solubility, and oral bioavailability more than 10%, also more than 20%.

Additional embodiments will be apparent from the Detailed Description and from the claims.

DETAILED DESCRIPTION OF THE INVENTION

As indicated in the Summary above, the present invention concerns the peroxisome proliferator-activated receptors (PPARs), which have been identified in humans and other mammals. A group of compounds have been identified, corresponding to Formula I, Ia, Ib, or Ic, that are active on one or more of the PPARs, in particular compounds that are active on one or more human PPARs. The identification of these compounds provides compounds that can be used as modulators on PPARs, including agonists of at least one of PPARα, PPARδ, and PPARγ, as well as dual PPAR agonists and pan-agonist, such as agonists of both PPARα and PPARγ, both PPARα and PPARδ, both PPARγ and PPARδ, or agonists of PPARα, PPARγ and PPARδ.

As used herein the following definitions apply unless otherwise indicated:

"Halo" or "Halogen"—alone or in combination means all halogens, that is, chloro (Cl), fluoro (F), bromo (Br), or iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl or branched alkyl, and includes a straight chain or branched alkyl group that optionally contains or is interrupted by a cycloalkyl portion. The straight chain or branched alkyl group is attached at any available atom to produce a stable compound. Examples of this include, but are not limited to, 4-(isopropyl)-cyclohexylethyl or 2-methyl-cyclopropylpentyl. In many embodiments, an alkyl is a straight or branched alkyl group containing from 1-15, 1-8, 1-6, 1-4, or 1-2, carbon atoms, such as methyl, ethyl, propyl, isopropyl, butyl, t-butyl and the like. "Optionally substituted alkyl" denotes unsubstituted alkyl or alkyl that is independently substituted with 1 to 3 groups or substituents selected from the group consisting of halo, hydroxy, optionally substituted lower alkoxy, optionally substituted acyloxy, optionally substituted aryloxy, optionally substituted heteroaryloxy, optionally substituted cycloalkyloxy, optionally substituted heterocycloalkyloxy, thiol, optionally substituted lower alkylthio, optionally substituted arylthio, optionally substituted heteroarylthio, optionally substituted cycloalkylthio, optionally substituted heterocycloalkylthio, optionally substituted alkylsulfinyl, optionally substituted arylsulfinyl, optionally substituted heteroarylsulfinyl, optionally substituted cycloalkylsulfinyl, optionally substituted heterocycloalkylsulfinyl, optionally substituted alkylsulfonyl, optionally substituted arylsulfonyl, optionally substituted heteroarylsulfonyl, optionally substituted cycloalkylsulfonyl, optionally substituted heterocycloalkylsulfonyl, optionally substituted amino, optionally substituted amido, optionally substituted amidino, optionally substituted urea, optionally substituted aminosulfonyl, optionally substituted alkylsulfonylamino, optionally substituted arylsulfonylamino, optionally substituted heteroarylsulfonylamino, optionally substituted cycloalkylsulfonylamino, optionally substituted heterocycloalkylsulfonylamino, optionally substituted alkylcarbonylamino, optionally substituted arylcarbonylamino, optionally substituted heteroarylcarbonylamino, optionally substituted cycloalkylcarbonylamino, optionally substituted heterocycloalkylcarbonylamino, optionally substituted carboxyl, optionally substituted acyl, optionally substituted cycloalkyl, optionally substituted heterocycloalkyl, optionally substituted aryl, optionally substituted heteroaryl, nitro, and cyano, attached at any available atom to produce a stable compound.

"Lower alkyl" refers to an alkyl group having 1-6 carbon atoms. "Optionally substituted lower alkyl" denotes lower alkyl or lower alkyl that is independently substituted with 1 to 3 groups or substituents as defined in [0057] attached at any available atom to produce a stable compound.

"Lower alkylene" refers to a divalent alkane-derived radical containing 1-6 carbon atoms, straight chain or branched, from which two hydrogen atoms are taken from the same carbon atom or from different carbon atoms. Examples of alkylene include, but are not limited to, —CH$_2$—, —CH$_2$CH$_2$—, and —CH$_2$CH(CH$_3$)—.

"Alkenyl"—alone or in combination means a straight, branched, or cyclic hydrocarbon containing 2-20, preferably 2-17, more preferably 2-10, even more preferably 2-8, most preferably 2-4, carbon atoms and at least one, preferably 1-3, more preferably 1-2, most preferably one, carbon to carbon double bond. In the case of a cycloalkenyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. "Optionally substituted alkenyl" denotes alkenyl or alkenyl that is independently substituted with 1 to 3 groups or substituents as defined in [0057] attached at any available atom to produce a stable compound.

"Lower alkenyl" refers to an alkenyl group having 2-6 carbon atoms. "Optionally substituted lower alkenyl" denotes lower alkenyl or lower alkenyl that is substituted with 1 to 3 groups or substituents as defined in [0057] attached at any available atom to produce a stable compound.

"Alkynyl"—alone or in combination means a straight or branched hydrocarbon containing 2-20, preferably 2-17, more preferably 2-10, even more-preferably 2-8, most preferably 2-4, carbon atoms containing at least one, preferably one, carbon to carbon triple bond. Examples of alkynyl groups include ethynyl, propynyl, butynyl, and the like. "Optionally substituted alkynyl" denotes alkynyl or alkynyl that is independently substituted with 1 to 3 groups or substituents as defined in [0057] attached at any available atom to produce a stable compound.

"Lower alkynyl" refers to an alkynyl group having 2-6 carbon atoms. "Optionally substituted lower alkynyl" denotes lower alkynyl or lower alkynyl that is substituted with 1 to 3 groups or substituents as defined in [0057] attached at any available atom to produce a stable compound.

"Lower alkoxy" denotes the group —OR$^e$, where R$^e$ is lower alkyl. "Optionally substituted lower alkoxy" denotes lower alkoxy in which R$^e$ is optionally substituted lower alkyl.

"Acyloxy" denotes the group —OC(O)R$^f$, where R$^f$ is hydrogen, lower alkyl, cycloalkyl, heterocycloalkyl, aryl, or heteroaryl. "Optionally substituted acyloxy" denotes acyloxy in which R$^f$ is hydrogen, optionally substituted lower alkyl, optionally substituted cycloalkyl, optionally substituted heterocycloalkyl, optionally substituted aryl, or optionally substituted heteroaryl.

"Aryloxy" denotes the group —OR$^g$, where R$^g$ is aryl. "Optionally substituted aryloxy" denotes aryloxy in which R$^g$ is optionally substituted aryl.

"Heteroaryloxy" denotes the group —OR$^h$, where R$^h$ is heteroaryl. "Optionally substituted heteroaryloxy" denotes heteroaryloxy in which R$^h$ is optionally substituted heteroaryl.

"Cycloalkyloxy" denotes the group —OR$^i$, where R$^i$ is cycloalkyl. "Optionally substituted cycloalkyloxy" denotes cycloalkyloxy in which R$^i$ is optionally substituted cycloalkyl.

"Heterocycloalkyloxy" denotes the group —OR$^j$, where R$^j$ is heterocycloalkyl. "Optionally substituted heterocycloalkyloxy" denotes heterocycloalkyloxy in which R$^j$ is optionally substituted heterocycloalkyl.

"Lower alkylthio" denotes the group —SR$^k$, where R$^k$ is lower alkyl. "Optionally substituted lower alkylthio" denotes lower alkylthio in which R$^k$ is optionally substituted lower alkyl.

"Arylthio" denotes the group —SR$^L$, where R$^L$ is aryl. "Optionally substituted arylthio" denotes arylthio in which R$^L$ is optionally substituted aryl.

"Heteroarylthio" denotes the group —SR$^m$, where R$^m$ is heteroaryl. "Optionally substituted heteroarylthio" denotes heteroarylthio in which R$^m$ is optionally substituted heteroaryl.

"Cycloalkylthio" denotes the group —SR$^n$, where R$^n$ is cycloalkyl. "Optionally substituted cycloalkylthio" denotes cycloalkylthio in which R$^n$ is optionally substituted cycloalkyl.

"Heterocycloalkylthio" denotes the group —SR$^o$, where R$^o$ is heterocycloalkyl. "Optionally substituted heterocycloalkylthio" denotes heterocycloalkylthio in which R$^o$ is optionally substituted heterocycloalkyl.

"Acyl" denotes groups —C(O)R$^p$, where R$^p$ is hydrogen, lower alkyl, cycloalkyl, heterocycloalkyl, aryl, or heteroaryl. "Optionally substituted acyl" denotes acyl in which R$^p$ is hydrogen, optionally substituted lower alkyl, optionally substituted cycloalkyl, optionally substituted heterocycloalkyl, optionally substituted aryl, or optionally substituted heteroaryl.

"Optionally substituted amino" denotes the group —NR$^q$R$^r$, where R$^q$ and R$^r$ may independently be hydrogen, optionally substituted lower alkyl, optionally substituted cycloalkyl, optionally substituted heterocycloalkyl, optionally substituted aryl, optionally substituted heteroaryl, optionally substituted acyl or optionally substituted sulfonyl, or R$^q$ and R$^r$ together with the nitrogen to which they are attached can form a 5-7 membered optionally substituted heterocycloalkyl or 5-7 membered optionally substituted heteroaryl.

"Optionally substituted amido" denotes the group —C(O)NR$^s$R$^t$, where R$^s$ and R$^t$ may independently be hydrogen, optionally substituted lower alkyl, optionally substituted cycloalkyl, optionally substituted heterocycloalkyl, optionally substituted aryl, or optionally substituted heteroaryl, or R$^s$ and R$^t$ together with the nitrogen to which they are attached can form a 5-7 membered optionally substituted heterocycloalkyl or 5-7 membered optionally substituted heteroaryl.

"Optionally substituted amidino" denotes the group —C(=NR$^u$)NR$^v$R$^w$, wherein R$^u$, R$^v$, and R$^w$ are independently hydrogen or optionally substituted lower alkyl.

"Optionally substituted urea" denotes the group —NR$^x$C(O)NR$^y$R$^z$, wherein R$^x$ is hydrogen or optionally substituted lower alkyl, and R$^y$ and R$^z$ are independently selected from hydrogen, optionally substituted lower alkyl, optionally substituted cycloalkyl, optionally substituted heterocycloalkyl, optionally substituted aryl or optionally substituted heteroaryl, or R$^y$ and R$^z$ together with the nitrogen to which they are attached can form a 5-7 membered optionally substituted heterocycloalkyl or 5-7 membered optionally substituted heteroaryl.

"Optionally substituted sulfonyl" denotes the group —S(O)$_2$R$^{aa}$, wherein R$^{aa}$ is optionally substituted lower alkyl, optionally substituted cycloalkyl, optionally substituted heterocycloalkyl, optionally substituted aryl, or optionally substituted heteroaryl.

"Optionally substituted aminosulfonyl" denotes the group —S(O)$_2$NR$^{bb}$R$^{cc}$, where R$^{bb}$ and R$^{cc}$ may independently be hydrogen, optionally substituted lower alkyl, optionally substituted cycloalkyl, optionally substituted heterocycloalkyl, optionally substituted aryl, or optionally substituted heteroaryl, or R$^{bb}$ and R$^{cc}$ together with the nitrogen to which they are attached can form a 5-7 membered optionally substituted heterocycloalkyl or 5-7 membered optionally substituted heteroaryl.

"Carboxyl" denotes the group —C(O)OR$^{dd}$, where R$^{dd}$ is hydrogen, lower alkyl, cycloalkyl, heterocycloalkyl, aryl, or heteroaryl. "Optionally substituted carboxyl" denotes carboxyl wherein R$^{dd}$ is hydrogen, optionally substituted lower alkyl, optionally substituted cycloalkyl, optionally substituted heterocycloalkyl, optionally substituted aryl, or optionally substituted heteroaryl.

"Carboxylic acid isostere" refers to a group selected from thiazolidine dione, hydroxamic acid, acyl-cyanamide, tetrazole, isoxazole, sulphonate, and sulfonamide. In functional terms, carboxylic acid isosteres mimic carboxylic acids by virtue of similar physical properties, including but not limited to molecular size or molecular shape. Isoxazole may be optionally substituted with lower alkyd lower alkyl substituted with 1-3 fluoro, aryl or heteroaryl, and wherein aryl or heteroaryl may be optionally substituted with 1-3 groups or substituents selected from halo, lower alkyl, fluoro substituted lower alkyl, lower alkoxy, fluoro substituted lower alkoxy, lower alkylthio, and fluoro substituted lower alkylthio. Sulfonamide may be optionally substituted with lower alkyl, fluoro substituted lower alkyl, acyl, aryl and heteroaryl, wherein aryl or heteroaryl may be optionally substituted with 1-3 groups or substituents selected from halo, lower alkyl, fluoro substituted lower alkyl, lower alkoxy, fluoro substituted lower alkoxy, lower alkylthio, and fluoro substituted lower alkylthio.

"Aryl" refers to a ring system containing aromatic hydrocarbons such as phenyl or naphthyl, which may be optionally fused with a cycloalkyl of preferably 5-7, more preferably 5-6, ring members. "Optionally substituted aryl" denotes aryl or aryl that is substituted with 1 to 3 groups or substituents as defined in [0057], or optionally substituted lower alkyl, optionally substituted lower alkenyl, or optionally substituted lower alkynyl, attached at any available atom to produce a stable compound.

"Aralkyl" refers to the group —$R^{ee}$—Ar where Ar is an aryl group and $R^{ee}$ is lower alkylene. "Optionally substituted aralkyl" denotes aralkyl or aralkyl in which the alkylene group is optionally substituted with 1 to 3 groups or substituents as defined in [0057], attached at any available atom to produce a stable compound, and in which the aryl group is optionally substituted with 1 to 3 groups or substituents as defined in [0057], or optionally substituted lower alkyl, optionally substituted lower alkenyl, or optionally substituted lower alkynyl, attached at any available atom to produce a stable compound.

"Heteroaryl"—alone or in combination means a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, and indolyl. "Optionally substituted heteroaryl" denotes heteroaryl or heteroaryl that is substituted with with 1 to 3 groups or substituents as defined in [0057], or optionally substituted lower alkyl, optionally substituted lower alkenyl, or optionally substituted lower alkynyl, attached at any available carbon or nitrogen to produce a stable compound.

"Heteroaralkyl" refers to the group —$R^{ff}$-HetAr where HetAr is a heteroaryl group and $R^{ff}$ is lower alkylene. "Optionally substituted heteroaralkyl" denotes heteroaralkyl or heteroaralkyl in which the lower alkylene group is optionally substituted with 1 to 3 groups or substituents as defined in [0057], attached at any available atom to produce a stable compound, and in which the heteroaryl group is optionally substituted with 1 to 3 groups or substituents as defined in [0057], or optionally substituted lower alkyl, optionally substituted lower alkenyl, or optionally substituted lower alkynyl, attached at any available carbon or nitrogen to produce a stable compound.

"Cycloalkyl" refers to saturated or unsaturated, non-aromatic monocyclic, bicyclic or tricyclic carbon ring systems of 3-8, more preferably 3-6, ring members per ring, such as cyclopropyl, cyclopentyl, cyclohexyl, adamantyl, and the like. "Optionally substituted cycloalkyl" denotes cycloalkyl or cycloalkyl that is substituted with with 1 to 3 groups or substituents as defined in [0057], or optionally substituted lower alkyl, optionally substituted lower alkenyl, or optionally substituted lower alkynyl, attached at any available atom to produce a stable compound.

"Cycloalkylalkyl" refers to the group —$R^{gg}$-Cyc where Cyc is a cycloalkyl group and $R^{gg}$ is a lower alkylene group. "Optionally substituted cycloalkylalkyl" denotes cycloalkylalkyl or cycloalkylalkyl in which the alkylene group is optionally substituted with 1 to 3 groups or substituents as defined in [0057], attached at any available atom to produce a stable compound, and in which the cycloalkyl group is optionally substituted with 1 to 3 groups or substituents as defined in [0057], or optionally substituted lower alkyl, optionally substituted lower alkenyl, or optionally substituted lower alkynyl, attached at any available atom to produce a stable compound.

"Heterocycloalkyl" means a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, piperazinyl, dihydrobenzofuryl, and dihydroindolyl. "Optionally substituted heterocycloalkyl" denotes heterocycloalkyl or heterocycloalkyl that is substituted with with 1 to 3 groups or substituents as defined in [0057], or optionally substituted lower alkyl, optionally substituted lower alkenyl, or optionally substituted lower alkynyl, attached at any available carbon or nitrogen to produce a stable compound.

"Heterocycloalkylalkyl" refers to the group —$R^{hh}$-Het where Het is a heterocycloalkyl group and $R^{hh}$ is a lower alkylene group. "Optionally substituted heterocycloalkylalkyl" denotes heterocycloalkylalkyl or heterocycloalkylalkyl in which the alkylene group is optionally substituted with 1 to 3 groups or substituents as defined in [0057], attached at any available atom to produce a stable compound, and in which the heterocycloalkyl group is optionally substituted with 1 to 3 groups or substituents as defined in [0057], or optionally substituted lower alkyl, optionally substituted lower alkenyl, or optionally substituted lower alkynyl, attached at any available carbon or nitrogen to produce a stable compound.

"Optionally substituted alkylsulfinyl" denotes the group —$S(O)R^{ii}$, wherein $R^{ii}$ is optionally substituted lower alkyl.

"Optionally substituted arylsulfinyl" denotes the group —$S(O)R^{jj}$, wherein $R^{jj}$ is optionally substituted aryl.

"Optionally substituted heteroarylsulfinyl" denotes the group —$S(O)R^{kk}$, wherein $R^{kk}$ is optionally substituted heteroaryl.

"Optionally substituted cycloalkylsulfinyl" denotes the group —$S(O)R^{LL}$, wherein $R^{LL}$ is optionally substituted cycloalkyl.

"Optionally substituted heterocycloalkylsulfinyl" denotes the group —$S(O)R^{mm}$, wherein $R^{mm}$ is optionally substituted heterocycloalkyl.

"Optionally substituted alkylsulfonyl" denotes the group —$S(O)_2R^{nn}$, wherein $R^{nn}$ is optionally substituted lower alkyl.

"Optionally substituted arylsulfonyl" denotes the group —$S(O)_2R^{oo}$, wherein $R^{oo}$ is optionally substituted aryl.

"Optionally substituted heteroarylsulfonyl" denotes the group —$S(O)_2R^{pp}$, wherein $R^{pp}$ is optionally substituted heteroaryl.

"Optionally substituted cycloalkylsulfonyl" denotes the group —$S(O)_2R^{qq}$, wherein $R^{qq}$ is optionally substituted cycloalkyl.

"Optionally substituted heterocycloalkylsulfonyl" denotes the group —$S(O)_2R^{rr}$, wherein $R^{rr}$ is optionally substituted heterocycloalkyl.

"Optionally substituted alkylsulfonylamino" denotes the group —$NR^{ss}S(O)_2R^{tt}$, wherein $R^{tt}$ is optionally substituted lower alkyl, and $R^{ss}$ is hydrogen or optionally substituted lower alkyl.

"Optionally substituted arylsulfonylamino" denotes the group —$NR^{uu}S(O)_2R^{vv}$, wherein $R^{vv}$ is optionally substituted aryl, and $R^{uu}$ is hydrogen or optionally substituted lower alkyl.

"Optionally substituted heteroarylsulfonylamino" denotes the group —NR$^{ww}$S(O)$_2$R$^{xx}$, wherein R$^{xx}$ is optionally substituted heteroaryl, and R$^{ww}$ is hydrogen or optionally substituted lower alkyl.

"Optionally substituted cycloalkylsulfonylamino" denotes the group —NR$^{yy}$S(O)$_2$R$^{zz}$, wherein R$^{zz}$ is optionally substituted cycloalkyl, and R$^{yy}$ is hydrogen or optionally substituted lower alkyl.

"Optionally substituted heterocycloalkylsulfonylamino" denotes the group —NR$^{ba}$S(O)$_2$R$^{bc}$, wherein R$^{bc}$ is optionally substituted heterocycloalkyl, and R$^{ba}$ is hydrogen or optionally substituted lower alkyl.

"Optionally substituted alkylcarbonylamino" denotes the group —NR$^{bd}$C(O)R$^{be}$, wherein R$^{be}$ is optionally substituted lower alkyl, and R$^{bd}$ is hydrogen or optionally substituted lower alkyl.

"Optionally substituted arylcarbonylamino" denotes the group —NR$^{bf}$C(O)R$^{bg}$, wherein R$^{bg}$ is optionally substituted aryl, and R$^{bf}$ is hydrogen or optionally substituted lower alkyl.

"Optionally substituted heteroarylcarbonylamino" denotes the group —NR$^{bh}$C(O)R$^{bi}$, wherein R$^{bi}$ is optionally substituted heteroaryl, and R$^{bh}$ is hydrogen or optionally substituted lower alkyl.

"Optionally substituted cycloalkylcarbonylamino" denotes the group —NR$^{bj}$C(O)R$^{bk}$, wherein R$^{bk}$ is optionally substituted cycloalkyl, and R$^{bj}$ is hydrogen or optionally substituted lower alkyl.

"Optionally substituted heterocycloalkylcarbonylamino" denotes the group —NR$^{bl}$C(O)R$^{bm}$, wherein R$^{bm}$ is optionally substituted heterocycloalkyl, and R$^{bl}$ is hydrogen or optionally substituted lower alkyl.

As used herein, the terms "ligand" and "modulator" are used equivalently to refer to a compound that changes the activity of a target biomolecule, e.g., a PPAR. Generally a ligand or modulator will be a small molecule, where "small molecule" refers to a compound with a molecular weight of 1500 daltons or less, or preferably 1000 daltons or less, 800 daltons or less, or 600 daltons or less. The effects of a PPAR may be modulated by a compound, for example, by increasing or decreasing the binding to transcriptional coactivators or transcriptional corepressors, resulting in changes in the expression levels of various target proteins or the activity of other transcription factors. In one instance, a PPAR agonist might function by enhancing the binding to coactivators, in another an antagonist could result in an increase in the binding to corepressors. In other cases, modulation might occur through the interference or enhancement of the binding of an agonist (natural or unnatural) to the PPAR. Upon binding an agonist, the conformation of a PPAR is altered and stabilized such that a binding cleft, made up in part of the AF-2 domain, is created and recruitment of transcriptional coactivators can occur. Coactivators enable nuclear receptors to initiate the transcription process. The result of the agonist-induced PPAR-coactivator interaction at the PPRE is an increase in gene transcription. Further, in connection with ligands and modulators of PPAR, the term "specific for PPAR" and terms of like import mean that a particular compound binds to a PPAR to a statistically greater extent than to other biomolecules that may be present in or originally isolated from a particular organism, e.g., at least 2, 3, 4, 5, 10, 20, 50, 100, or 1000-fold. Also, where biological activity other than binding is indicated, the term "specific for PPAR" indicates that a particular compound has greater biological effect on PPAR than do other biomolecules (e.g., at a level as indicated for binding specificity). Similarly, the specificity can be for a specific PPAR isoform with respect to other PPAR isoforms that may be present in or originally isolated from a particular organism. In the context of ligands interacting with PPARs, the terms "activity on", "activity toward," and like terms mean that such ligands have EC$_{50}$ or IC$_{50}$ less than 10 mM, less than 1 mM, less than 100 nM, less than 50 nM, less than 20 nM, less than 10 nM, less than 5 nM, or less than 1 nM with respect to at least one PPAR as determined in a generally accepted PPAR activity assay.

Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. In some cases, the specificity is with reference to a limited set of other biomolecules, e.g., in the case of PPARs, in some cases the reference may be to other receptors, or for a particular PPAR, it may be other PPARs. In particular embodiments, the greater specificity is at least 2, 3, 4, 5, 8, 10, 50, 100, 200, 400, 500, or 1000-fold greater specificity.

The term "pharmaceutical composition" refers to a preparation that includes a therapeutically significant quantity of an active agent, which is prepared in a form adapted for administration to a subject. Thus, the preparation is "pharmaceutically acceptable", indicating that it does not have properties that would cause a reasonably prudent medical practitioner to avoid administration of the material to a patient, taking into consideration the disease or conditions to be treated and the respective route of administration. In many cases, such a pharmaceutical composition is a sterile preparation, e.g. for injectables.

The term "PPAR-mediated" disease or condition and like terms refer to a disease or condition in which the biological function of a PPAR affects the development and/or course of the disease or condition, and/or in which modulation of PPAR alters the development, course, and/or symptoms of the disease or condition. Similarly, the phrase "PPAR modulation provides a therapeutic benefit" indicates that modulation of the level of activity of PPAR in a subject indicates that such modulation reduces the severity and/or duration of the disease, reduces the likelihood or delays the onset of the disease or condition, and/or causes an improvement in one or more symptoms of the disease or condition. In some cases the disease or condition may be mediated by any one or more of the PPAR isoforms, e.g., PPARγ, PPARα, PPARδ, PPARγ and PPARα, PPARγ and PPARδ, PPARα and PPARδ, or PPARγ, PPARα, and PPARδ.

The term "composition" refers to a formulation suitable for administration to an intended animal subject for therapeutic purposes that contains at least one pharmaceutically active compound.

The term "therapeutically effective" indicates that the materials or amount of material is effective to prevent, alleviate, or ameliorate one or more symptoms of a disease or medical condition, and/or to prolong the survival of the subject being treated.

A "pharmaceutically acceptable salt" is intended to mean a salt that retains the biological effectiveness of the free acid and base forms of the specified compound and that is not biologically or otherwise unacceptable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or base, such as salts including sodium, chloride, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, ftimarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, .gamma.-hydroxybutyrates, glycollates, tartrates, methane-sulfonates, propanesulfonates, naphthalene-1-sulfonates, naphthalene-2-sulfonates, and mandelates.

The term "pharmaceutically acceptable metabolite" refers to a pharmacologically acceptable product, which may be an active product, produced through metabolism of a specified compound (or salt thereof) in the body of a subject or patient. Metabolites of a compound may be identified using routine techniques known in the art, and their activities determined using tests such as those described herein. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

The term "PPAR" refers to a peroxisome proliferator-activated receptor as recognized in the art. As indicated above, the PPAR family includes PPARα (also referred to as PPARa or PPARalpha), PPARδ (also referred to as PPARd or PPAR-delta), and PPARγ (also referred to as PPARg or PPAR-gamma). The individual PPARs can be identified by their sequences, where exemplary reference sequence accession numbers are: NM_005036 (cDNA sequence for hPPARa) SEQ ID NO: 1, NP_005027 (protein sequence for hPPARa) SEQ ID NO: 2, NM_015869 (cDNA sequence for hPPARg isoform 2) SEQ ID NO: 5, NP_056953 (protein sequence for hPPARg isoform 2) SEQ ID NO: 6, NM_006238 (cDNA sequence for hPPARd) SEQ ID NO: 9, and NP_006229 (protein sequence for hPPARd) SEQ ID NO: 10. One of ordinary skill in the art will recognize that sequence differences will exist due to allelic variation, and will also recognize that other animals, particularly other mammals, have corresponding PPARs, which have been identified or can be readily identified using sequence alignment and confirmation of activity, can also be used. One of ordinary skill in the art will also recognize that modifications can be introduced in a PPAR sequence without destroying PPAR activity. Such modified PPARs can also be used in the present invention, e.g., if the modifications do not alter the binding site conformation to the extent that the modified PPAR lacks substantially normal ligand binding.

As used herein in connection with the design or development of ligands, the term "bind" and "binding" and like terms refer to a non-covalent energetically favorable association between the specified molecules (i.e., the bound state has a lower free energy than the separated state, which can be measured calorimetrically). For binding to a target, the binding is at least selective, that is, the compound binds preferentially to a particular target or to members of a target family at a binding site, as compared to non-specific binding to unrelated proteins not having a similar binding site. For example, BSA is often used for evaluating or controlling for non-specific binding. In addition, for an association to be regarded as binding, the decrease in free energy going from a separated state to the bound state must be sufficient so that the association is detectable in a biochemical assay suitable for the molecules involved.

By "assaying" is meant the creation of experimental conditions and the gathering of data regarding a particular result of the experimental conditions. For example, enzymes can be assayed based on their ability to act upon a detectable substrate. Likewise, for example, a compound or ligand can be assayed based on its ability to bind to a particular target molecule or molecules and/or to modulate an activity of a target molecule.

By "background signal" in reference to a binding assay is meant the signal that is recorded under standard conditions for the particular assay in the absence of a test compound, molecular scaffold, or ligand that binds to the target molecule. Persons of ordinary skill in the art will realize that accepted methods exist and are widely available for determining background signal.

By "binding site" is meant an area of a target molecule to which a ligand can bind non-covalently. Binding sites embody particular shapes and often contain multiple binding pockets present within the binding site. The particular shapes are often conserved within a class of molecules, such as a molecular family. Binding sites within a class also can contain conserved structures such as, for example, chemical moieties, the presence of a binding pocket, and/or an electrostatic charge at the binding site or some portion of the binding site, all of which can influence the shape of the binding site.

By "binding pocket" is meant a specific volume within a binding site. A binding pocket is a particular space within a binding site at least partially bounded by target molecule atoms. -Thus-a-binding-pocket-is-a-particular-shape; indentation, or cavity-in the binding site. Binding pockets can contain particular chemical groups or structures that are important in the non-covalent binding of another molecule such as, for example, groups that contribute to ionic, hydrogen bonding, van der Waals, or hydrophobic interactions between the molecules.

By "chemical structure" or "chemical substructure" is meant any definable atom or group of atoms that constitute a part of a molecule. Normally, chemical substructures of a scaffold or ligand can have a role in binding of the scaffold or ligand to a target molecule, or can influence the three-dimensional shape, electrostatic charge, and/or conformational properties of the scaffold or ligand.

By "orientation", in reference to a binding compound bound to a target molecule is meant the spatial relationship of the binding compound and at least some of its consitituent atoms to the binding pocket and/or atoms of the target molecule at least partially defining the binding pocket.

By "clog P" is meant the calculated log P of a compound, "P" referring to the partition coefficient of the compound between a lipophilic and an aqueous phase, usually between octanol and water.

In the context of compounds binding to a target, the term "greater affinity" indicates that the compound binds more tightly than a reference compound, or than the same compound in a reference condition, i.e., with a lower dissociation constant. In particular embodiments, the greater affinity is at least 2, 3, 4, 5, 8, 10, 50, 100, 200, 400, 500, 1000, or 10,000-fold greater affinity.

By binding with "moderate affinity" is meant binding with a $K_D$ of from about 200 nM to about 1 μM under standard conditions. By "moderately high affinity" is meant binding at a $K_D$ of from about 1 nM to about 200 nM. By binding at "high affinity" is meant binding at a $K_D$ of below about 1 nM under standard conditions. The standard conditions for binding are at pH 7.2 at 37° C. for one hour. For example, typical binding conditions in a volume of 100 μl/well would comprise a PPAR, a test compound, HEPES 50 mM buffer at pH 7.2, NaCl 15 mM, ATP 2 μM, and bovine serum albumin (1 ug/well), at 37° C. for one hour.

Binding compounds can also be characterized by their effect on the activity of the target molecule. Thus, a "low activity" compound has an inhibitory concentration ($IC_{50}$) (for inhibitors or antagonists) or effective concentration ($EC_{50}$) (applicable to agonists) of greater than 1 μM under standard conditions. By "moderate activity" is meant an $IC_{50}$ or $EC_{50}$ of 200 nM to 1 μM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ (or $EC_{50}$) is defined as the concentration of compound at which 50% of the activity of the target molecule (e.g., enzyme or other protein) activity being measured is lost (or gained) relative to activity when no compound is present. Activity can be measured using methods known to those of ordinary skill in the art, e.g., by measuring any detectable product or signal produced by occurrence of an enzymatic reaction, or other activity by a protein being measured. For PPAR agonists, activities can be determined as described in the Examples, or using other such assay methods known in the art.

By "protein-ligand complex" or "co-complex" is meant a protein and ligand bound non-covalently together.

By "protein" is meant a polymer of amino acids. The amino acids can be naturally or non-naturally occurring. Proteins can also contain modifications, such as being glycosylated, phosphorylated, or other common modifications.

By "protein family" is meant a classification of proteins based on structural and/or functional similarities. For example, kinases, phosphatases, proteases, and similar groupings of proteins are protein families. Proteins can be grouped into a protein family based on having one or more protein folds in common, a substantial similarity in shape among folds of the proteins, homology, or based on having a common function. In many cases, smaller families will be specified, e.g., the PPAR family.

By "specific biochemical effect" is meant a therapeutically significant biochemical change in a biological system causing a detectable result. This specific biochemical effect can be, for example, the inhibition or activation of an enzyme, the inhibition or activation of a protein that binds to a desired target, or similar types of changes in the body's biochemistry. The specific biochemical effect can cause alleviation of symptoms of a disease or condition or-another desirable effect. The detectable result can also be detected through an intermediate step.

By "standard conditions" is meant conditions under which an assay is performed to obtain scientifically meaningful data. Standard conditions are dependent on the particular assay, and can be generally subjective. Normally the standard conditions of an assay will be those conditions that are optimal for obtaining useful data from the particular assay. The standard conditions will generally minimize background signal and maximize the signal sought to be detected.

By "standard deviation" is meant the square root of the variance. The variance is a measure of how spread out a distribution is. It is computed as the average squared deviation of each number from its mean. For example, for the numbers 1, 2, and 3, the mean is 2 and the variance is:

$$\sigma^2 = \frac{(1-2)^2 + (2-2)^2 + (3-2)^2}{3} = 0.667.$$

In the context of this invention, by "target molecule" is meant a molecule that a compound, molecular scaffold, or ligand is being assayed for binding to. The target molecule has an activity that binding of the molecular scaffold or ligand to the target molecule will alter or change. The binding of the compound, scaffold, or ligand to the target molecule can preferably cause a specific biochemical effect when it occurs in a biological system. A "biological system" includes, but is not limited to, a living system such as a human, animal, plant, or insect. In most but not all cases, the target molecule will be a protein or nucleic acid molecule.

By "pharmacophore" is meant a representation of molecular features that are considered to be responsible for a desired activity, such as interacting or binding with a receptor. A pharmacophore can include 3-dimensional (hydrophobic groups, charged/ionizable groups, hydrogen bond donors/acceptors), 2D (substructures), and 1D (physical or biological) properties.

As used herein in connection with numerical values, the terms "approximately" and "about" mean±10% of the indicated value.

I. Applications of PPAR Agonists

The PPARs have been recognized as suitable targets for a number of different diseases and conditions. Some of those applications are described briefly below. Additional applications are known and the present compounds can also be used for those diseases and conditions.

(a) Insulin resistance and diabetes: In connection with insulin resistance and diabetes, PPARγ is necessary and sufficient for the differentiation of adipocytes in vitro and in vivo. In adipocytes, PPARγ increases the expression of numerous genes involved in lipid metabolism and lipid uptake. In contrast, PPARγ down-regulates leptin, a secreted, adipocyte-selective protein that has been shown to inhibit feeding and augment catabolic lipid metabolism. This receptor activity could explain the increased caloric uptake and storage noted in vivo upon treatment with PPARγ agonists. Clinically, TZDs, including troglitazone, rosiglitazone, and pioglitazone, and non-TZDs, including farglitazar, have insulin-sensitizing and antidiabetic activity. (Bergen & Wagner, supra.)

PPARγ has been associated with several genes that affect insulin action. TNFα, a proinflammatory cytokine that is expressed by adipocytes, has been associated with insulin resistance. PPARγ agonists inhibited expression of TNFα in adipose tissue of obese rodents, and ablated the actions of TNFα in adipocytes in vitro. PPARγ agonists were shown to inhibit expression of 11β-hydroxysteroid dehydrogenase 1 (11β-HSD-1), the enzyme that converts cortisone to the glucocorticoid agonist cortisol, in adipocytes and adipose tissue of type 2 diabetes mouse models. This is noteworthy since hypercortico-steroidism exacerbates insulin resistance. Adipocyte Complement-Related Protein of 30 kDa (Acrp30 or adiponectin) is a secreted adipocyte-specific protein that decreases glucose, triglycerides, and free fatty acids. In comparison to normal human subjects, patients with type 2 diabetes have reduced plasma levels of Acrp30. Treatment of diabetic mice and nondiabetic human subjects with PPARγ agonists increased plasma levels of Acrp30. Induction of Acrp30 by PPARγ agonists might therefore also play a key role in the insulin-sensitizing mechanism of PPARγ agonists in diabetes. (Bergen & Wagner, supra.)

PPARγ is expressed predominantly in adipose tissue. Thus, it is believed that the net in vivo efficacy of PPARγ agonists involves direct actions on adipose cells with secondary effects in key insulin responsive tissues such as skeletal muscle and liver. This is supported by the lack of glucose-lowering efficacy of rosiglitazone in a mouse model of severe insulin resistance where white adipose tissue was essentially absent. Furthermore, in vivo treatment of insulin resistant rats produces acute (<24 h) normalization of adipose tissue insulin action whereas insulin-mediated glucose uptake in muscle was not improved until several days after the initiation of therapy. This is consistent with the fact that PPARγ agonists can produce an increase in adipose tissue insulin action after direct in vitro incubation, whereas no such effect could be demonstrated using isolated in vitro incubated skeletal muscles. The beneficial metabolic effects of PPARγ agonists on muscle and liver may be mediated by their ability to (a) enhance insulin-mediated adipose tissue uptake, storage (and potentially catabolism) of free fatty acids; (b) induce the production of adipose-derived factors with potential insulin sensitizing activity (e.g., Acrp30); and/or (c) suppress the circulating levels and/or actions of insulin resistance-causing adipose-derived factors such as TNFα or resistin. (Bergen & Wagner, supra.)

(b) Dyslipidemia and atherosclerosis: In connection with dyslipidemia and atherosclerosis, PPARα has been shown to play a critical role in the regulation of cellular uptake, activation, and β-oxidation of fatty acids. Activation of PPARα induces expression of fatty acid transport proteins and enzymes in the peroxisomal β-oxidation pathway. Several mitochondrial enzymes involved in the energy-harvesting catabolism of fatty acids are robustly upregulated by PPARα agonists. Peroxisome proliferators also activate expression of the CYP4As, a subclass of cytochrome P450 enzymes that catalyze the ω-hydroxylation of fatty acids, a pathway that is particularly active in the fasted and diabetic states. In sum, it is clear that PPARα is an important lipid sensor and regulator of cellular energy-harvesting metabolism. (Bergen & Wagner, supra.)

Atherosclerosis is a very prevalent disease in Westernized societies. In addition to a strong association with elevated LDL cholesterol, "dyslipidemia" characterized by elevated triglyceride-rich particles and low levels of HDL cholesterol is commonly associated with other aspects of a metabolic syndrome that includes obesity, insulin resistance, type 2 diabetes, and an increased risk of coronary artery disease. Thus, in 8,500 men with known coronary artery disease, 38% were found to have low HDL (<35 mg/dL) and 33% had elevated triglycerides (>200 mg/dL). In such patients, treatment with fibrates resulted in substantial triglyceride lowering and modest HDL-raising efficacy. More-importantly, a recent large prospective trial showed that-treatment with gemfibrozil produced a 22% reduction in cardiovascular events or death. Thus PPARα agonists can effectively improve cardiovascular risk factors and have a net benefit to improve cardiovascular outcomes. In fact, fenofibrate was recently approved in the United States for treatment of type IIA and IIB hyper-lipidemia. Mechanisms by which PPARα activation cause triglyceride lowering are likely to include the effects of agonists to suppress hepatic apo-CIII gene expression while also stimulating lipoprotein lipase gene expression. Dual PPARγ/α agonists, including KRP-297 and DRF 2725, possess potent lipid-altering efficacy in addition to antihyperglycemic activity in animal models of diabetes and lipid disorders.

The presence of PPARα and/or PPARγ expression in vascular cell types, including macrophages, endothelial cells, and vascular smooth muscle cells, suggests that direct vascular effects might contribute to potential antiatherosclerosis efficacy. PPARα and PPARα activation have been shown to inhibit cytokine-induced vascular cell adhesion and to suppress monocyte-macrophage migration. Several additional studies have also shown that PPARγ-selective compounds have the capacity to reduce arterial lesion size and attenuate monocyte-macrophage homing to arterial lesions in animal models of atherosclerosis. PPARγ is present in macrophages in human atherosclerotic lesions, and may play a role in regulation of expression of matrix metalloproteinase-9 (MMP-9), which is implicated in atherosclerotic plaque rupture (Marx et al., *Am J Pathol.* 1998, 153(1):17-23). Downregulation of LPS induced secretion of MMP-9 was also observed for both PPARα and PPARγ agonists, which may account for beneficial effects observed with PPAR agonists in animal models of atherosclerosis (Shu et al., *Biochem Biophys Res Commun.* 2000, 267(1):345-9). PPARγ is also shown to have a role in intercellular adhesion molecule-1 (ICAM-1) protein expression (Chen et al., *Biochem Biophys Res Commun.* 2001, 282(3):717-22) and vascular cell adhesion molecule-1 (VCAM-1) protein expression (Jackson et al., *Arterioscler Thromb Vasc Biol.* 1999, 19(9):2094-104) in endothelial cells, both of which play a role in the adhesion of monocytes to endothelial cells. In addition, two recent studies have suggested that either PPARα or PPARγ activation in macrophages can induce the expression of a cholesterol efflux "pump" protein.

It has been found that relatively selective PPARδ agonists produce minimal, if any, glucose- or triglyceride-lowering activity in murine models of type 2 diabetes in comparison with efficacious PPARγ or PPARα agonists. Subsequently, a modest increase in HDL-cholesterol levels was detected with PPARδ agonists in db/db mice. Recently, Oliver et al. (supra) reported that a potent, selective PPARδ agonist could induce a substantial increase in HDL-cholesterol levels while reducing triglyceride levels and insulin resistance in obese rhesus monkeys.

Thus, via multifactor mechanisms that include improvements in circulating lipids, systemic and local anti-inflammatory effects, and, inhibition of vascular cell proliferation, PPARα, PPARγ, and PPARδ agonists can be used in the treatment or prevention of atherosclerosis. (Bergen & Wagner, supra.)

(c) Inflammation: Monocytes and macrophages are known to play an important part in the inflammatory process through the release of inflammatory cytokines and the production of nitric oxide by inducible nitric oxide synthase. Rosiglitazone has been shown to induce apoptosis of macrophages at concentrations that paralleled its affinity for PPARγ. This ligand has also been shown to block inflammatory cytokine synthesis in colonic cell lines. This latter observation suggests a mechanistic explanation for the observed anti-inflammatory actions of TZDs in rodent models of colitis. Additional studies have examined the relationship between macrophages, cytokines and PPARγ and agonists thereof (Jiang et al., *Nature* 1998, 391(6662):82-6., Ricote et al., *Nature* 1998, 391(6662):79-82, Hortelano et al., *J Immunol.* 2000, 165(11): 6525-31, and Chawla et al., *Nat Med.* 2001, 7(1):48-52) suggesting a role for PPARγ agonists in treating inflammatory responses, for example in autoimmune diseases.

The migration of monocytes and macrophages plays a role in the development of inflammatory responses as well. PPAR ligands have been shown to have an effect on a variety of chemokines. Monocyte chemotactic protein-1 (MCP-1)

directed migration of monocytes is attenuated by PPARγ and PPARα ligands in a monocytic leukemia cell line (Kintscher et al., *Eur J Pharmacol*. 2000, 401(3):259-70). MCP-1 gene expression was shown to be suppressed by PPARγ ligand 15-deoxy-Delta(12,14)PGJ2 (15d-PGJ2) in two monocytic cell lines, which also showed induction of IL-8 gene expression (Zhang et al., *J Immunol*. 2001, 166(12):7104-11).

Anti-inflammatory actions have been described for PPARα ligands that can be important in the maintenance of vascular health. Treatment of cytokine-activated human macrophages with PPARα agonists induced apoptosis of the cells. It was reported that PPARα agonists inhibited activation of aortic smooth muscle cells in response to inflammatory stimuli (Staels et al., *Nature* 1998, 393:790-793.) In hyperlipidemic patients, fenofibrate treatment decreased the plasma concentrations of the inflammatory cytokine interleukin-6.

Anti-inflammatory pathways in airway smooth muscle cells were investigated with respect to PPARα and PPARγ (Patel et al., *The Journal of Immunology*, 2003, 170:2663-2669). This study demonstrated an anti-inflammatory effect of a PPARγ ligand that may be useful in the treatment of COPD and steroid-insensitive asthma.

(d) Hypertension: Hypertension is a complex disorder of the cardiovascular system that has been shown to be associated with insulin resistance. Type 2 diabetes patients demonstrate a 1.5-2-fold increase in hypertension in comparison with the general population. Troglitazone, rosiglitazone, and pioglitazone therapy have been shown to decrease blood pressure in diabetic patients as well as troglitazone therapy in obese, insulin-resistant subjects. Since such reductions in blood pressure were shown to correlate with decreases in insulin levels, they can be mediated by an improvement in insulin sensitivity. However, since TZDs also lowered blood pressure in one-kidney one-clip Sprague Dawley rats, which are not insulin resistant, it was proposed that the hypotensive action of PPARγ agonists is not exerted solely through their ability to improve insulin sensitivity. Other mechanisms that have been invoked to explain the antihypertensive effects of PPARγ agonists include their ability to (a) downregulate expression of peptides that control vascular tone such as PAI-I, endothelin, and type-c natriuretic peptide C or (b) alter calcium concentrations and the calcium sensitivity of vascular cells. (Bergen & Wagner, supra.)

(e) Cancer: PPAR modulation has also been correlated with cancer treatment. (Burstein et al.; *Breast Cancer Res. Treat.* 2003, 79(3):391-7; Alderd et al.; *Oncogene*, 2003, 22(22): 3412-6).

(f) weight Control: Administration of PPARα agonists can induce satiety, and thus are useful in weight loss or maintenance. Such PPARα agonists can act preferentially on PPARα, or can also act on another PPAR, or can be PPAR pan-agonists. Thus, the satiety inducing effect of PPARα agonists can be used for weight control or loss.

(g) Autoimmune diseases: PPAR agonists may provide benefits in the treatment of autoimmune diseases. Agonists of PPAR isoforms may be involved in T cell and B cell trafficking or activity, the altering of oligodendrocyte function or differentiation, the inhibition of macrophage activity, the reduction of inflammatory responses, and neuroprotective effects, some or all of which may be important in a variety of autoimmune diseases.

Multiple sclerosis (MS) is a neurodegenerative autoimmune disease that involves the demyelination of axons and formation of plaques. PPARδ mRNA has been shown to be strongly expressed in immature oligodendrocytes (Granneman et al., *J Neurosci Res*. 1998, 51 (5):563-73). PPARδ selective agonists or pan-agonists were shown to accelerate differentiation of oligodendrocytes, with no effect on differentiation observed with a PPARγ selective agonist. An alteration in the myelination of corpus callosum was observed in PPARδ null mice (Peters et al., *Mol Cell Biol*. 2000, 20(14): 5119-28). It was also shown that PPARδ mRNA and protein is expressed throughout the brain in neurons and oligodendrocytes, but not in astrocytes (Woods et al., *Brain Res*. 2003, 975(1-2):10-21). These observations suggest that PPARδ has a role in myelination, where modulation of such a role could be used to treat multiple sclerosis by altering the differentiation of oligodendrocytes, which may result in slowing of the demyelination, or even promoting the remyelination of axons. It has also been shown that oligodendrocyte-like B12 cells, as well as isolated spinal cord oligodendrocytes from rat, are affected by PPARγ agonists. Alkyl-dihydroxyacetone phosphate synthase, a key peroxisomal enzyme involved in the synthesis of plasmologens, which are a key component of myelin, is increased in PPARγ agonist treated B12 cells, while the number of mature cells in isolated spinal cord oligodendrocytes increases with PPARγ agonist treatment.

The role of PPARs in the regulation of B and T cells may also provide therapeutic benefits in diseases such as MS. For example, it has been shown that PPARγ agonists can inhibit the secretion of IL-2 by T cells (Clark et al., *J Immunol*. 2000, 164(3):1364-71) or may induce apoptosis in T cells (Harris et al., *Eur J Immunol*. 2001, 31(4):1098-105), suggesting an important role in cell-mediated immune responses. An antiproliferative and cytotoxic effect on B cells by PPARγ agonists has also been observed (Padilla et al., *Clin Immunol*. 2002, 103(1):22-33).

The anti-inflammatory effects of PPAR modulators, as discussed herein, may also be useful in treating MS, as well as a variety of other autoimmune diseases such as Type-1 diabetes mellitus, psoriasis, vitiligo, uveitis, Sjogren's disease, pemphigus foliaceus, inclusion body myositis, polymyositis, dermatomyositis, scleroderma, Grave's disease, Hashimoto's disease, chronic graft-versus host disease, rheumatoid arthritis, inflammatory bowel syndrome, and Crohn's disease. Using a mouse model, the PPARα agonists gemfibrozil and fenofibrate were shown to inhibit clinical signs of experimental autoimmune encephalomyelitis, suggesting that PPARα agonists may be useful in treating inflammatory conditions such as multiple sclerosis (Lovett-Racke et al., *J Immunol*. 2004, 172(9):5790-8).

Neuroprotective effects that appear to be associated with PPARs may also aid in the treatment of MS. The effects of PPAR agonists on LPS induced neuronal cell death were studied using cortical neuron-glial co-cultures. PPARγ agonists 15d-PGJ2, ciglitazone and troglitazone were shown to prevent the LPS-induced neuronal cell death, as well as abolish NO and PGE2 release and a reduction in iNOS and COX-2 expression (Kim et al., *Brain Res*. 2002, 941(1-2):1-10).

Rheumatoid arthritis (RA) is an autoimmune inflammatory disease that results in the destruction of joints. In addition to chronic inflammation and joint damage due in part to mediators such as IL-6 and TNF-alpha, osteoclast differentiation is also implicated in damage to the joints. PPAR agonists may regulate these pathways, providing therapeutic benefits in treatment of RA. In studies using PPARγ agonist troglitazone in fibroblast-like synovial cells (FLS) isolated from patients with rheumatoid arthritis, an inhibition of cytokine mediated inflammatory responses was observed (Yamasaki et al., *Clin Exp Immunol.*, 2002, 129(2):379-84). PPARγ agonists have also demonstrated beneficial effects in a rat or mouse model of RA (Kawahito et al., *J Clin Invest*. 2000, 106(2):189-97; Cuzzocrea et al., *Arthritis Rheum*. 2003, 48(12):3544-56).

The effects of the PPARα ligand fenofibrate on rheumatoid synovial fibroblasts from RA patients also showed inhibition of cytokine production, as well as NF-KappaB activation and osteoclast differentiation. Fenofibrate was also shown to inhibit the development of arthritis in a rat model (Okamoto et al., *Clin Exp Rheumatol.* 2005, 23(3):323-30).

Psoriasis is a T cell mediated autoimmune disease, where T cell activation leads to release of cytokines and resulting proliferation of keratinocytes. In addition to anti-inflammatory effects, the differentiation of keratinocytes may also be a therapeutic target for PPAR agonists. Studies in a PPARδ null mouse model suggest using PPARδ ligand to selectively induce keratinocyte differentiation and inhibit cell proliferation (Kim et al., *Cell Death Differ.* 2005). Thiazolidinedione ligands of PPARγ have been shown to inhibit the proliferation of psoriatic keratinocytes in monolayer and organ culture, and when applied topically inhibit epidermal hyperplasia of human psoriatic skin transplanted to SCID mice (Bhagavathula et al., *J Pharmacol Exp Ther.* 2005, 315(3):996-1004).

(h) Neurodegenerative diseases: The modulation of the PPARs may provide benefits in the treatment of neuronal diseases. For example, the anti-inflammatory effects of PPAR modulators discussed herein have also been studied with respect to neuronal diseases such as Alzheimer's disease and Parkinson's disease.

In addition to inflammatory processes, Alzheimer's disease is characterized by deposits of amyloid-beta (Abeta) peptides and neurofibrillary tangles. A decrease in the levels of Abeta peptide in neuronal and non-neuronal cells was observed with induced expression of PPARγ, or by activation of PPARγ using a thiazolidinedione (Camacho et al., *J Neurosci.* 2004, 24(48):10908-17). Treatment of APP717 mice with PPARγ agonist pioglitazone showed several beneficial effects, including reduction in activated microglia and reactive astrocytes in the hippocampus and cortex, reduction in proinflammatory cyclooxygenase 2 and inducible nitric oxide synthase, decreased β-secretase-1 mRNA and protein levels, and a reduction in the levels of soluble Abeta1-42 peptide (Heneka et al., *Brain.* 2005, 128(Pt 6):1442-53).

Regions of degeneration of dopamine neurons in Parkinson's disease have been associated with increased levels of inflammatory cytokines (Nagatsu et al., *J Neural Transm Suppl.* 2000; (60):277-90). The effect of PPARγ agonist pioglitazone on dopaminergic nerve cell death and glial activation was studied in an MPTP mouse model of Parkinson's disease, wherein orally administered pioglitazone resulted in reduced glial activation as well as prevention of dopaminergic cell loss (Breidert et al. *Journal of Neurochemistry,* 2002, 82: 615).

(i) Other indications: PPARγ modulators have shown inhibition of VEGF-induced choroidal angiogenesis as well as repression of choroidal neovascularization effects, suggesting potential for treatment of retinal disorders. PPARδ has been shown to be expressed in implantation sites and in decidual cells in rats, suggesting a role in pregnancy, such as to enhance fertility. These studies were reviewed in Kota et al., *Pharmacological Research,* 2005, 51:85-94. The management of pain, either neuropathic or inflammatory, is also suggested as a possible target for PPAR modulators. Burstein, S., Life Sci. 2005, 77(14):1674-84, suggests that PPARγ provides a receptor function for the activity of some cannabinoids. Lo Verme et al., *Mol Pharmacol.* 2005, 67(1):15-9, identifies PPARα as a target responsible for pain and inflammation reducing effects of palmitoylethanolamide (PEA). PEA selectively activates PPARα in vitro, and induces expression of PPARα mRNA when applied topically to mice. In animal models of carrageenan-induced paw edema and phorbol ester-induced ear edema, inflammation in wild type mice is attenuated by PEA, which has no effect in PPARα deficient mice. PPARα agonists OEA, GW7647 and Wy-14643 demonstrate similar effects. Benani et al., *Neurosci Lett.* 2004, 369(1):59-63, uses a model of inflammation in rats to assess the PPAR response in the rat spinal cord following injection of complete Freund's adjuvant into the hind paw. It was shown that PPARα was activated, suggesting a role in pain pathways.

In accordance with the description above, isoforms of the PPAR family of nuclear receptors are clearly involved in the systemic regulation of lipid metabolism and serve as "sensors" for fatty acids, prostanoid metabolites, eicosanoids and related molecules. These receptors function to regulate a broad array of genes in a coordinate fashion. Important biochemical pathways that regulate insulin action, lipid oxidation, lipid synthesis, adipocyte differentiation, peroxisome function, cell apoptosis, and inflammation can be modulated through the individual PPAR isoforms. Strong therapeutic effects of PPARα and PPARγ agonists to favorably influence systemic lipid levels, glucose homeostasis, and atherosclerosis risk (in the case of PPARα activation in humans) have recently been discovered. PPARα and PPARγ agonists are presently used clinically to favorably alter systemic lipid levels and glucose homeostasis, respectively. Recent observations made using PPARS ligands suggest that this isoform is also an important therapeutic target for dyslipidemia and insulin resistance, as well.

Thus, PPAR modulators, such as those described herein, can be used in the prophylaxis and/or therapeutic treatment of a variety of different disease and conditions, such as obesity, overweight condition, hyperlipidemia, dyslipidemia including associated diabetic dyslipidemia and mixed dyslipidemia, hypoalphalipoproteinemia, Syndrome X, Type II diabetes mellitus, Type I diabetes, hyperinsulinemia, impaired glucose tolerance, insulin resistance, a diabetic complication (e.g., neuropathy, nephropathy, retinopathy or cataracts), hypertension, coronary heart disease, heart failure, hypercholesterolemia, inflammation, thrombosis, congestive heart failure, cardiovascular disease (including atherosclerosis, arteriosclerosis, and hypertriglyceridemia), epithelial hyperproliferative diseases (such as eczema and psoriasis), cancer, neuropathic or inflammatory pain, conditions associated with the lung and gut, regulation of appetite and food intake in subjects suffering from disorders such as obesity, anorexia bulimia and anorexia nervosa, neurodegenerative diseases, such as Alzheimer's disease, Parkinson's disease, and amyotrophic lateral sclerosis, autoimmune diseases such as Type-1 diabetes mellitus, vitiligo, uveitis, Sjogren's disease, pemphigus foliaceus, inclusion body myositis, polymyositis, dermatomyositis, scleroderma, Grave's disease, Hashimoto's disease, chronic graft-versus host disease, rheumatoid arthritis, inflammatory bowel syndrome, Crohn's disease and multiple sclerosis, pregnancy (e.g. fertility), diseases involving airway smooth muscle cells such as asthma and COPD, and angiogenesis related conditions, such as macular degeneration.

II. PPAR Active Compounds

As indicated in the Summary and in connection with applicable diseases and conditions, a number of different PPAR agonist compounds have been identified. In addition, the present invention provides PPAR agonist compounds described by Formula I, Ia, Ib, or Ic as provided in the Summary above. These compounds can be used in the treatment or prophylaxis of a disease or condition selected from obesity, overweight condition, hyperlipidemia,-dyslipidemia including associated diabetic dyslipidemia and mixed dyslipidemia, hypoalphalipoproteinemia, Syndrome X, Type II diabetes mellitus, Type I diabetes, hyperinsulinemia, impaired glucose tolerance, insulin resistance, a diabetic complication (e.g., neuropathy, nephropathy, retinopathy or cataracts), hypertension, coronary heart disease, heart failure, hypercholesterolemia, inflammation, thrombosis, congestive heart failure, cardiovascular disease (including atherosclerosis, arteriosclerosis, and hypertriglyceridemia), epithelial hyperproliferative diseases (such as eczema and psoriasis), cancer, neuropathic or inflammatory pain, conditions associated with the lung and gut, and regulation of appetite and food intake in subjects suffering from disorders such as obesity, anorexia bulimia and anorexia nervosa, neurodegenerative diseases, such as Alzheimer's disease, Parkinson's disease, and amyotrophic lateral sclerosis, autoimmune diseases such as Type-1 diabetes mellitus, vitiligo, uveitis, Sjogren's disease, pemphigus foliaceus, inclusion body myositis, polymyositis, dermatomyositis, scleroderma, Grave's disease, Hashimoto's disease, chronic graft-versus host disease, rheumatoid arthritis, inflammatory bowel syndrome, Crohn's disease and multiple sclerosis, pregnancy (e.g. fertility), diseases involving airway smooth muscle cells such as asthma and COPD, and angiogenesis related conditions, such as macular degeneration.

The activity of the compounds can be assessed using methods known to those of skill in the art, as well as methods described herein. Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity used as a comparator or control. It will be appreciated that modulators can also be combined with the enzyme activators or inhibitors to find modulators which inhibit the enzyme activation or repression that is otherwise caused by the presence of the known enzyme modulator. Similarly, when ligands to a target are sought, known ligands of the target can be present in control/calibration assay wells.

Exemplary compounds described by Formula I are provided in Table 1 as well as in the synthetic examples. Additional compounds within Formula I, Ia, Ib, or Ic can be prepared and tested to confirm activity using conventional methods and the guidance provided herein.

TABLE 1

Exemplary compounds of the invention.

| Compound Number | Structure | Name | Molecular weight | |
| --- | --- | --- | --- | --- |
| | | | Calc. | Measured |
| 27 | 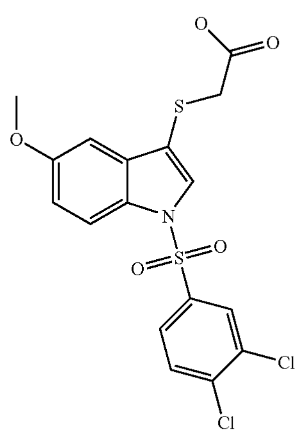 | [5-Methoxy-1-(3,4-dichloro-benzenesulfonyl)-1H-indol-3-ylsulfonyl]-acetic acid | 444.96 | MS(ESI)[M − H$^+$]$^-$ = 443.95 |
| 28 | 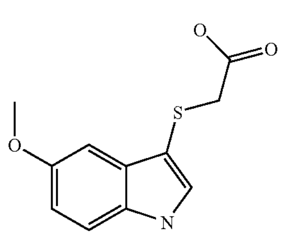 | (5-Methoxy-1H-indol-3-ylsulfanyl)-acetic acid | 237.05 | MS(ESI)[M − H$^+$]$^-$ = 238.15 |

TABLE 1-continued

Exemplary compounds of the invention.

| Compound Number | Structure | Name | Molecular weight Calc. | Measured |
|---|---|---|---|---|
| 23 | | [5-Bromo-1-(4-methoxy-benzenesulfonyl)-1H-indol-3-yloxy]-acetic acid | 440.27 | MS(ESI)[M − H⁺]⁻ = 438.0; 440.0 |
| 24 | | 3-[5-Bromo-1-(4-methoxy-benzenesulfonyl)-1H-indol-3-yloxy]-propionic acid | 454.29 | MS(ESI)[M − H⁺]⁻ = 452.0; 454.0 |
| 29 | | 3-[5-Bromo-1-(4-methoxy-benzenesulfonyl)-1H-indol-3-yloxy]-propionic acid methyl ester | 468.29 | MS(ESI)[M − H⁺]⁻ = 466.0; 468.0 |

(a) Measuring Enzymatic and Binding Reactions During Screening Assays

Techniques for measuring the progression of enzymatic and binding reactions, e.g., in multicontainer carriers, are known in the art and include, but are not limited to, the following.

Spectrophotometric and spectrofluorometric assays are well known in the art. Examples of such assays include the use of colorimetric assays for the detection of peroxides, as described in Gordon, A. J. and Ford, R. A., *The Chemist's Companion: A Handbook Of Practical Data, Techniques And References,* John Wiley and Sons, N.Y., 1972, Page 437.

Fluorescence spectrometry may be used to monitor the generation of reaction products. Fluorescence methodology is generally more sensitive than absorption methodology. The use of fluorescent probes is well known to those skilled in the art. For reviews, see Bashford et al., *Spectrophotometry and Spectrofluorometry: A Practical Approach,* pp. 91-114, IRL Press Ltd. (1987); and Bell, *Spectroscopy In Biochemistry,* Vol. I, pp. 155-194, CRC Press (1981).

In spectrofluorometric methods, enzymes are exposed to substrates that change their intrinsic fluorescence when processed by the target enzyme. Typically, the substrate is non-fluorescent and is converted to a fluorophore through one or more reactions. As a non-limiting example, SMase activity can be detected using the Amplex® Red reagent (Molecular Probes, Eugene, Oreg.). In order to measure sphingomyelinase activity using Amplex® Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex® Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owicki et al., *Genetic Engineering News,* 1997, 17:27.

FP is particularly desirable since its readout is independent of the emission intensity (Checovich, et al., *Nature* 1995, 375:254-256; Dandliker, et al., *Methods in Enzymology* 1981, 74:3-28) and is thus insensitive to the presence of colored compounds that quench fluorescence emission. FP and FRET (see below) are well-suited for identifying compounds that block interactions between sphingolipid receptors and their ligands. See, for example, Parker et al., *J. Biomol. Screen.,* 2000, 5:77-88.

Fluorophores derived from sphingolipids that may be used in FP assays are commercially available. For example, Molecular Probes (Eugene, Oreg.) currently sells sphingomyelin and ceramide fluorophores. These are, respectively, N-(4,4-difluoro-5,7-dimethyl-4-bora-3a,4a-diaza-s-indacene-3-pentanoyl)sphingosyl phosphocholine (BODIPY® FL C5-sphingomyelin); N-(4,4-difluoro-5,7-dimethyl-4-bora-3a,4a-diaza-s-indacene-3-dodecanoyl)sphingosyl phosphocholine (BODIPY® FL C12-sphingomyelin); and N-(4,4-difluoro-5,7-dimethyl-4-bora-3a,4a-diaza-s-indacene-3-pentanoyl)sphingosine (BODIPY® FL C5-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan.

Exemplary normal-and-polarized fluorescence readers include the POLARION® fluorescence polarization system (Tecan AG, Hombrechtikon, Switzerland). General multiwell plate readers for other assays are available, such as the VERSAMAX® reader and the SPECTRAMAX® multiwell plate spectrophotometer (both from Molecular Devices).

Fluorescence resonance energy transfer (FRET) is another useful assay for detecting interaction and has been described. See, e.g., Heim et al., *Curr. Biol.* 1996, 6:178-182; Mitra et al., *Gene* 1996, 173:13-17; and Selvin et al., *Meth. Enzymol.* 1995, 246:300-345. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., *J. Lipid Res.* 38:2365-2373 (1997); Kahl et al., *Anal. Biochem.* 243:282-283 (1996); Undenfriend et al., *Anal. Biochem.* 161:494-500 (1987)). See also U.S. Pat. Nos. 4,626,513 and 4,568,649, and European Patent No. 0,154,734. One commercially available system uses FLASHPLATE® scintillant-coated plates (NEN Life Science Products, Boston, Mass.).

The target molecule can be bound to the scintillator plates by a variety of well known means. Scintillant plates are available that are derivatized to bind to fusion proteins such as GST, His6 or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT® microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., *Anal. Biochem.* 257:112-119, 1998).

Additionally, the assay can utilize AlphaScreen (amplified luminescentproximity homogeneous assay) format, e.g., AlphaScreening system (Packard BioScience). AlphaScreen is generally described in Seethala and Prabhavathi, *Homogenous Assays: AlphaScreen, Handbook of Drug Screening*, Marcel Dekkar Pub. 2001, pp. 106-110. Applications of the technique to PPAR receptor ligand binding assays are described, for example, in Xu et al., 2002, *Nature* 415:813-817.

(b) Assessment of Efficacy of Compounds in Disease Model Systems

The utility of compounds of Formula I, Ia, Ib, or Ic for the treatment of diseases such as autoimmune disease and neurological disease can be readily assessed using model systems known to those of skill in the art. For example, efficacy of PPAR modulators in models of Alzheimer's disease can be tested by mimicking inflammatory injury to neuronal tissues and measuring recovery using molecular and pharmacological markers (Heneka, M. T. et al. (2000) *J. Neurosci.* 20, 6862-6867). Efficacy of PPAR modulators in multiple sclerosis has been monitored using the accepted model of experimental autoimmune encephalomyelitis (EAE, Storer et al (2004) *J. Neuroimmunol.* 161, 113-122. See also: Niino, M. et al. (2001) *J. Neuroimmunol.* 116, 40-48; Diab, A. et al. (2002) *J. Immunol.* 168, 2508-2515; Natarajan, C. and Bright, J. J. (2002) *Genes Immun.* 3, 59-70; Feinstein, D. L. et al. (2002) *Ann. Neurol.* 51, 694-702.)

(c) Isomers, Prodrugs, and Active Metabolites

Compounds contemplated herein are described with reference to both generic formulae and specific compounds. In addition, the invention compounds may exist in a number of different forms or derivatives, all within the scope of the present invention. These include, for example, tautomers, stereoisomers, racemic mixtures, regioisomers, salts, prodrugs (e.g., carboxylic acid esters), solvated forms, different crystal forms or polymorphs, and active metabolites (d) Tautomers, Stereoisomers, Regioisomers, and Solvated Forms It is understood that certain compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present invention may exist as stereoisomers, i.e. they have the same sequence of covalently bonded atoms and differ in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present invention. Unless specified to the contrary, all such steroisomeric forms are included within the formulae provided herein.

In certain embodiments, a chiral compound of the present invention is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In certain embodiments, the compound is present in optically pure form.

For compounds in which synthesis involves addition of a single group at a double bond, particularly a carbon-carbon double bond, the addition may occur at either of the double bond-linked atoms. For such compounds, the present invention includes both such regioisomers.

Additionally, the formulae are intended to cover solvated as well as unsolvated forms of the identified structures. For example, the indicated structures include both hydrated and non-hydrated forms. Other examples of solvates include the structures in combination with isopropanol, ethanol, methanol, DMSO, ethyl acetate, acetic acid, or ethanolamine.

(e) Prodrugs and Metabolites

In addition to the present formulae and compounds described herein, the invention also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Typically, the prodrug is inactive, or less active than the active compound, but may provide advantageous handling, administration, or metabolic properties. For example, some prodrugs are esters of the active compound; during metabolysis, the ester group is cleaved to yield the active drug. Also, some prodrugs are activated enzymatically to yield the active compound, or a compound which, upon further chemical reaction, yields the active compound. A common example is an alkyl ester of a carboxylic acid.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the follow types:

Oxidative reactions: Oxidative reactions are exemplified without limitation to reactions such as oxidation of alcohol, carbonyl, and acid functions, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation to reactions such as reduction of carbonyl groups, reduction of hydroxyl groups and carbon-carbon double bonds, reduction of nitrogen-containing functions groups, and other reduction reactions.

Reactions without change in the oxidation state: Reactions without change in the state of oxidation are exemplified without limitation to reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 2004/0077595, Ser. No. 10/656,838, incorporated herein by reference.) Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, *The Practice of Medicinal Chemistry*, Ch. 31 -32, Ed. Wermuth, Academic Press, San Diego, Calif., 2001.

Prodrugs may proceed from prodrug form to active form in a single step or may have one or more intermediate forms which may themselves have activity or may be inactive.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic process in the body of a subject or patient. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug.

Prodrugs and active metabolites may be identified using routine techniques known in the art. See, e.g., Bertolini et al., 1997, *J. Med. Chem.*, 40:2011-2016; Shan et al., 1997, *J. Pharm. Sci.* 86(7):756-757; Bagshawe, 1995, *Drug. Dev. Res.*, 34:220-230; Wermuth, *The Practice of Medicinal Chemistry*, Ch. 31-32, Academic Press, San Diego, Calif., 2001.

(f) Pharmaceutically Acceptable Salts

Compounds can be formulated as or be in the form of pharmaceutically acceptable salts. Pharmaceutically acceptable salts are non-toxic salts in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see *Remington's Pharmaceutical Sciences*, 19$^{th}$ ed., Mack Publishing Co., Easton, Pa., Vol. 2, p. 1457, 1995. Such salts can be prepared using the appropriate corresponding bases.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent.

Thus, for example, if the particular compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Similarly, if the particular compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

Unless specified to the contrary, specification of a compound herein includes pharmaceutically acceptable salts of such compound.

(g) Polymorphic Forms

In the case of agents that are solids, it is understood by those skilled in the art that the compounds and salts may exist in different crystal or polymorphic forms, all of which are intended to be within the scope of the present invention and specified formulae.

III. Administration

The methods and compounds will typically be used in therapy for human patients. However, they may also be used to treat similar or identical diseases in other vertebrates, e.g., mammals such as other primates, animals of commercial significance, e.g., sports animals, farm animals, e.g., bovines, equines, porcines, and ovines, and pets such as dogs and cats.

Suitable dosage forms, in part, depend upon the use or the route of administration, for example, oral, transdermal, transmucosal, inhalant, or by injection (parenteral). Such dosage forms should allow the compound to reach target cells. Other factors are well known in the art, and include considerations such as toxicity and dosage forms that retard the compound or composition from exerting its effects. Techniques and formulations generally may be found in Remington: *The Science and Practice of Pharmacy*, $21^{st}$ edition, Lippincott, Williams and Wilkins, Philadelphia, Pa., 2005 (hereby incorporated by reference herein).

Compounds of the present invention (i.e. Formula I, including Formulae Ia-Ic, and all sub-embodiments disclosed herein) can be formulated as pharmaceutically acceptable salts.

Carriers or excipients can be used to produce compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

The compounds can be administered by different routes including intravenous, intraperitoneal, subcutaneous, intramuscular, oral, transmucosal, rectal, transdermal, or inhalant. In some embodiments, oral administration is preferred. For oral administration, for example, the compounds can be formulated into conventional oral dosage forms such as capsules, tablets, and liquid preparations such as syrups, elixirs, and concentrated drops.

Pharmaceutical preparations for oral use can be obtained, for example, by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, the compounds of the invention are formulated in sterile liquid solutions, preferably in physiologically compatible buffers or solutions, such as saline solution, Hank's solution, or Ringer's solution. In addition, the compounds may be formulated in solid form and redissolved or suspended immediately prior to use. Lyophilized forms can also be produced.

Administration can also be by transmucosal, topical, transdermal, or inhalant means. For transmucosal, topical or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

The topical compositions of this invention are formulated preferably as oils, creams, lotions, ointments and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will, of course, be continuous rather than intermittent throughout the dosage regimen.

For inhalants, compounds of the invention may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds of the invention may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium-bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of various compounds to be administered can be determined by standard procedures taking into account factors such as the compound $EC_{50}$, the biological half-life of the compound, the age, size, and weight of the patient, and the disorder associated with the patient. The importance of these and other factors are well known to those of ordinary skill in the art. Generally, a dose will be between about 0.01 and 50 mg/kg, preferably 0.1 and 20 mg/kg of the patient being treated. Multiple doses may be used.

The compounds of the invention may also be used in combination with other therapies for treating the same disease. Such combination use includes administration of the compounds and one or more other therapeutics at different times, or co-administration of the compound and one or more other therapies. In certain embodiments, dosage may be modified for one or more of the compounds of the invention or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound of the present invention, or at the same time as a compound of the invention. Use in combination also includes use with a therapy or medical procedure that is administered once or infrequently, such as surgery, along with a compound of the invention administered within a short time or longer time before or after the other therapy or procedure. In certain embodiments, the present invention provides for delivery of compounds of the invention and one or more other drug therapeutics delivered by a different route of administration or by the same route of administration. The use in combination for any route of administration includes delivery of compounds of the invention and one or more other drug-therapeutics-delivered by the same route of administration together in any formulation, including formulations where the two compounds are chemically linked in such a way that they maintain their therapeutic activity when administered. In one aspect, the other drug therapy may be co-administered with one or more compounds of the invention. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of compounds of the invention and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

IV. Synthesis of Compounds of Formula I

Compounds with the chemical structure of Formula I can be prepared in a number of different synthetic routes, including, for example, the synthetic schemes described herein for groups of compounds within Formula I. Additional synthetic routes can be utilized by one skilled in chemical synthesis.

Certain of the syntheses can utilize key intermediate II in the synthesis, when Q is O, to afford compounds of Formula Id. Key intermediate II can be prepared as follows:

Synthesis of Compound II

One synthetic route for Intermediate II compounds is shown below in Scheme 1a. In these compounds, U, V, W, and Y can be C as in indole, or can be other heteroatoms as specified for Formula I. In synthetic Scheme 1a and other synthetic schemes described herein for groups of compounds, it should be understood that generic formulae in the schemes (e.g., Formula III in Scheme 1a) describe a set of compounds, but are referenced in the text description of the synthesis in the singular. Notably, some compounds such as Intermediate II may be represented in two tautomeric forms, such as the enol form shown in Formula II and the keto form shown in Formula Ia in Scheme 1a, and they may be used interchangeably to represent the same compound:

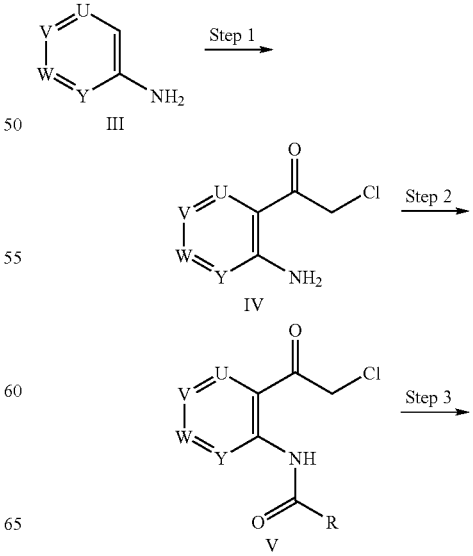

-continued

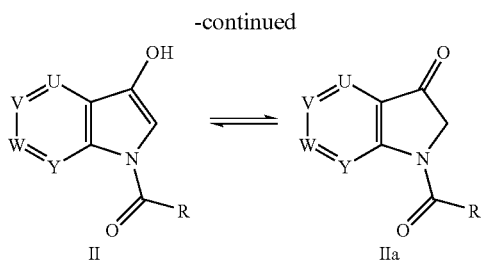

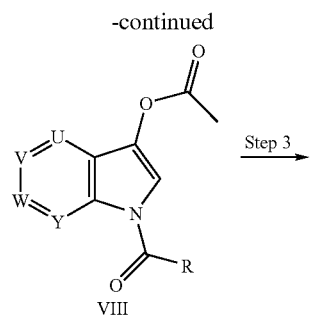

Step 1—Preparation of Formula IV

Compound IV may be prepared by reacting a commercially available aromatic amine of Formula III with chloroacetonitrile in the presence of boron trichloride and a Lewis base (e.g. aluminum trichloride) with heating to reflux for several hours in an inert solvent (e.g. benzene) and purification by conventional methods (e.g. silica gel chromatography) (Sugasawa et. al.; *J. Org. Chem.*, 44, 1979, 578).

Step 2—Preparation of Formula V

Compound V may be prepared where R is methyl or trifluoromethyl by reacting a compound of Formula IV with acetic anhydride or trifluoroacetic anhydride, respectively, and heating (e.g. 80° C.) for 30 minutes, followed by purification (e.g. silica gel chromatography) (Sugasawa et. al.; *J. Org. Chem.*, 44, 1979, 578).

Step 3—Preparation of Compound II

Key compound II may be prepared by reacting a compound of Formula V with a base (e.g. sodium hydride or potassium carbonate) in an inert solvent (e.g. 1,2-dimethoxyethane or acetonitrile) and stirring with ice-cooling or at room temperature for several minutes to several hours, followed by purification and isolation by conventional means (e.g. aqueous work-up and silica gel chromatography). (Sugasawa et. al.; *J. Org. Chem.*, 44, 1979, 578).

Compounds of the type of key compound II may also be prepared in accordance with Scheme 1b as shown below.

Scheme 1b

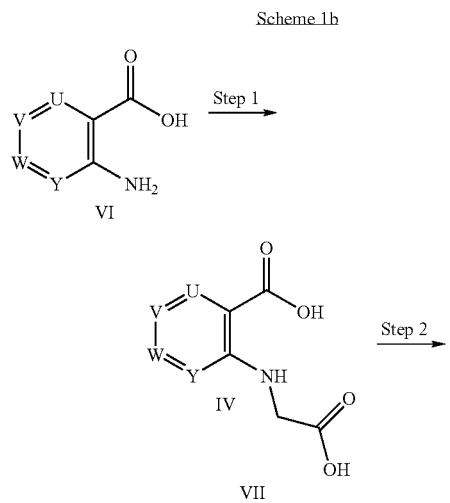

Step 1—Preparation of Formula VII

Compound VII may be prepared by reacting a commercially available anthranilic acid or analog of Formula III with 2-chloroacetic acid in the presence of base (e.g. sodium carbonate) typically at room temperature for 1-4 hours followed by purification and isolation by conventional means (e.g. aqueous work-up and recrystallization).

Step 2—Preparation of Formula VIII

Compound VIII, where R is methyl, may be prepared by reacting a compound of Formula VII with sodium acetate in refluxing acetic anhydride for several hours, followed by purification and isolation by conventional means (e.g. recrystallization) (Su & Tsou; *J. Am. Chem. Soc.*, 1960, 82:1187).

Step 3—Preparation of Key Compound II

Compound II, where R is methyl, may be prepared from a compound of Formula VIII by selective deprotection with sodium in methanol at room temperature typically for 30-60 minutes, followed by isolation and purification by conventional means (e.g. aqueous work-up and recrystallization) (Su & Tsou; *J. Am. Chem. Soc.*, 1960, 8:1187).

Compounds of Formula Id may be prepared from compound II by substitution of the 3-hydroxy, followed by removal of the acetyl on N-1 and substitution of the N-1 as shown in Scheme 2.

Scheme 2

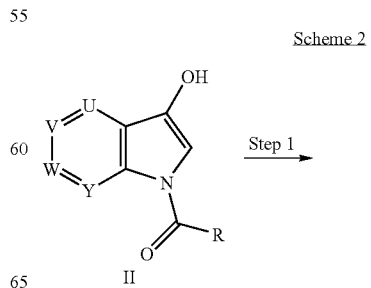

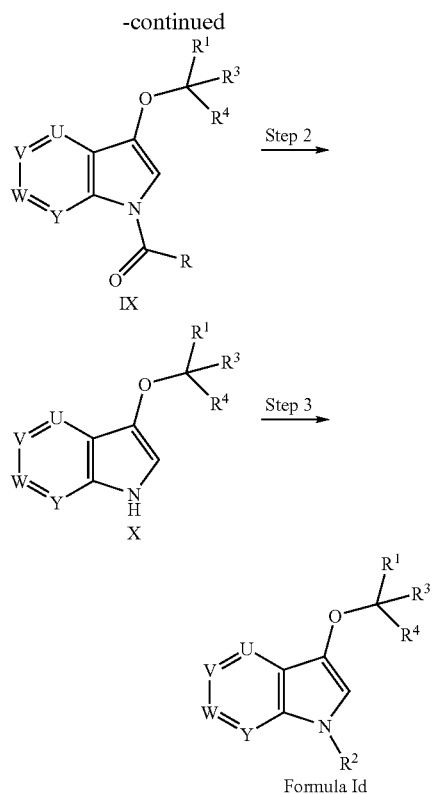

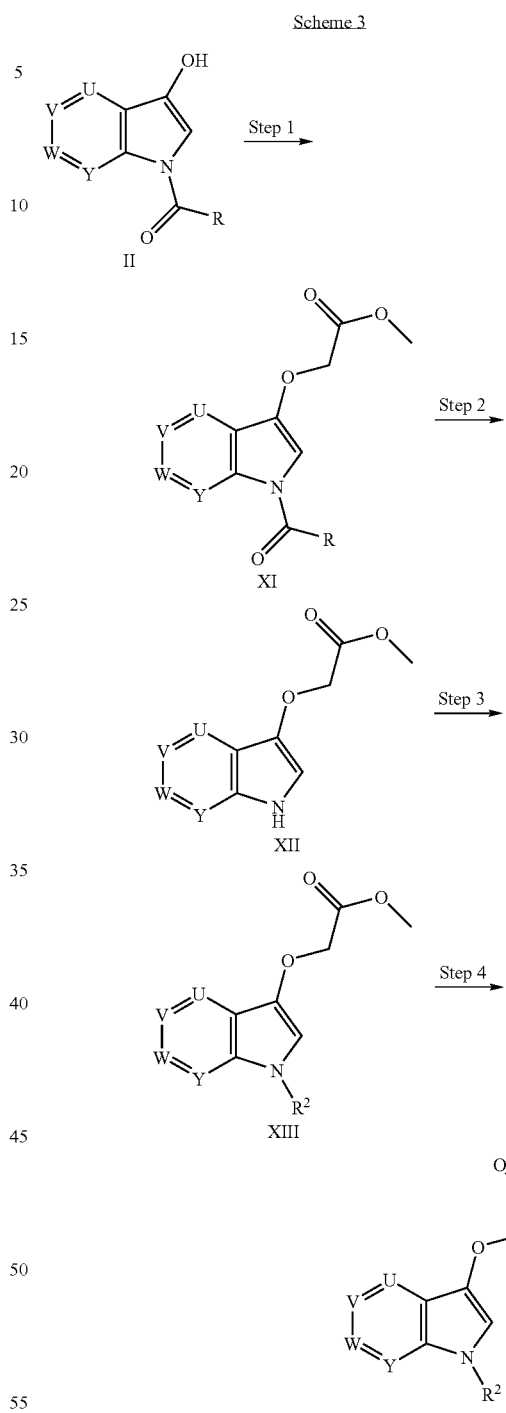

Scheme 3

Step 1—Preparation of Formula IX

Compound IX may be prepared by substituting compound II, where R is methyl or trifluoromethyl, with an appropriate reagent (e.g. methyl 2-bromoacetate) containing the $R^1$, $R^3$ and $R^4$ substituents and appropriate leaving group (e.g. chloro, bromo, tosyl) in the presence of base (e.g. potassium carbonate) in an inert solvent (e.g. acetone) typically for 12-18 hours with heating to reflux, followed by isolation and purification by conventional means (e.g. aqueous work-up and silica gel chromatography). (Andersen et. al., *J. Med. Chem.*, 1996, 39:3723.)

Step 2—Preparation of Formula X

Compound X may be prepared by removal of the N-substituent of a compound of Formula IX using a base (e.g. potassium hydroxide) in a solvent (e.g. methanol) typically at room temperature for 2 to 24 hours, followed by isolation and purification by conventional means (e.g. aqueous work-up and silica gel chromatography). (Naylor et. al., *J. Med. Chem.*, 1997, 40:2335.)

Step 3—Preparation of Formula Id

Compound of Formula Id may be prepared by treating compound of Formula X with a base (e.g. sodium hydride) in an inert solvent (e.g. DMF), followed by the addition of $R^2L_c$, where $L_c$ is a leaving group (e.g. chloro, bromo), and stirring at room temperature, typically for 16 to 24 hours, followed by isolation and purification by conventional means (e.g. aqueous work-up and silica gel chromatography). (Andersen et. al., *J. Med. Chem.*, 1996, 39:3723.)

In one particular embodiment of Formula Id, $R^1$ is carboxylic acid and $R^3$ and $R^4$ are hydrogen, which may be prepared from compound II according to Scheme 3.

Step 1—Preparation of Formula XI

Compound XI may be prepared by substituting compound II, where R is methyl or trifluoromethyl, with methyl 2-bromoacetate in the presence of base (e.g. potassium carbonate) in an inert solvent (e.g. acetone) typically for 12-18 hours with heating to reflux, followed by isolation and purification by conventional means (e.g. aqueous work-up and silica gel chromatography). (Andersen et. al., *J. Med. Chem.*, 39, 1996, 3723.)

Step 2—Preparation of Formula XII

Compound XII may be prepared by removal of the N-substituent of a compound of Formula XI using a base (e.g. potassium hydroxide) in a solvent (e.g. methanol) typically at room temperature for 2 to 24 hours, followed by isolation and purification by conventional means (e.g. aqueous work-up and silica gel chromatography). (Naylor et. al., *J. Med. Chem.*, 40, 1997, 2335.)

Step 3—Preparation of Formula XIII

Compound of Formula XIII may be prepared by treating compound of Formula XII with a base (e.g. sodium hydride) in an inert solvent (e.g. DMF), followed by the addition of $R^2L_c$, where $L_c$ is a leaving group (e.g. chloro, bromo), and stirring at room temperature, typically for 16 to 24 hours, followed by isolation and purification by conventional means (e.g. aqueous work-up and silica gel chromatography). (Andersen et. al., *J. Med. Chem.*, 1996, 39:723)

Step 4—Preparation of Formula Id

Compound of Formula Id wherein $R^1$ is carboxylic acid and $R^3$ and $R^4$ are hydrogen may be prepared by hydrolysis of compound of Formula XIII with aqueous base (e.g. sodium hydroxide), typically for 6-18 hours, in an inert solvent (e.g. tetrahydrofuran), followed by isolation and purification by conventional means (e.g. aqueous work-up and silica gel chromatography).

Compounds of Formula Ie, where Q is S, may be prepared as shown in Scheme 4:

Step 1—Preparation of Formula XV

Compound of Formula XV may be prepared by bromination of compound of Formula XIV with bromine, in an inert solvent (e.g. DMF), followed by isolation and purification by conventional means (e.g. aqueous work-up and silica gel chromatography).

Step 2—Preparation of Formula XVI

Intermediate XIV may be prepared by treating compound of Formula XV with an appropriate thiol (e.g. ethyl 2-mercaptoacetate) and a base (e.g. potassium carbonate), in an inert solvent (e.g. acetone) at reflux for 18-24 hours, followed by isolation and purification by conventional means (e.g. aqueous work-up and silica gel chromatography). (Salituro et; al., *J. Med. Chem.*, 35, 1992, 1791.)

Step 3—Preparation of Formula Ie

Compound of Formula Ie may be prepared by treating compound of Formula XVII with a base (e.g. sodium hydride) in an inert solvent (e.g. DMF), followed by the addition of $R^2L_c$, where $L_c$ is a leaving group (e.g. chloro, bromo), and stirring at room temperature, typically for 16 to 24 hours, followed by isolation and purification by conventional means (e.g. aqueous work-up and silica gel chromatography).

In one particular embodiment of Formula Ib, $R^1$ is carboxylic acid and $R^3$ and $R^4$ are hydrogen, which may be prepared according to Scheme 6.

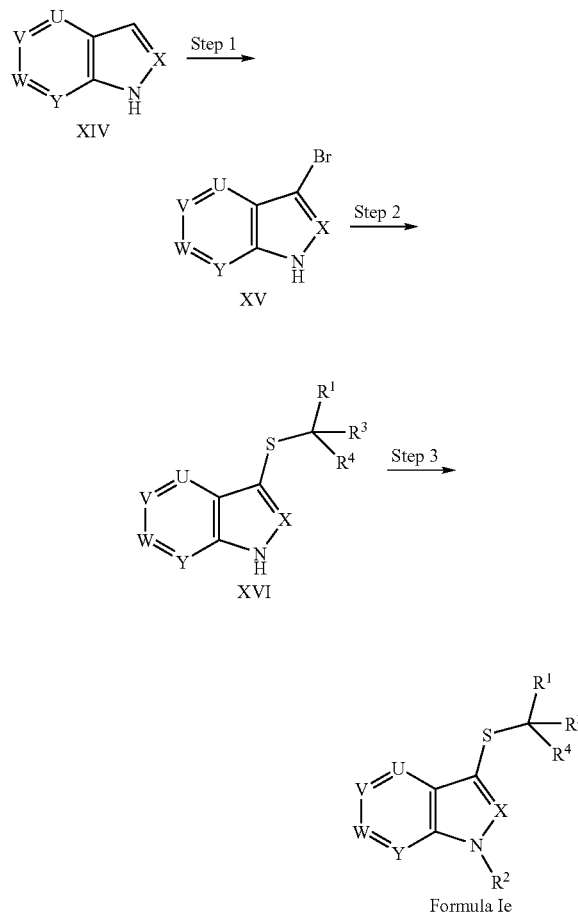

Scheme 4

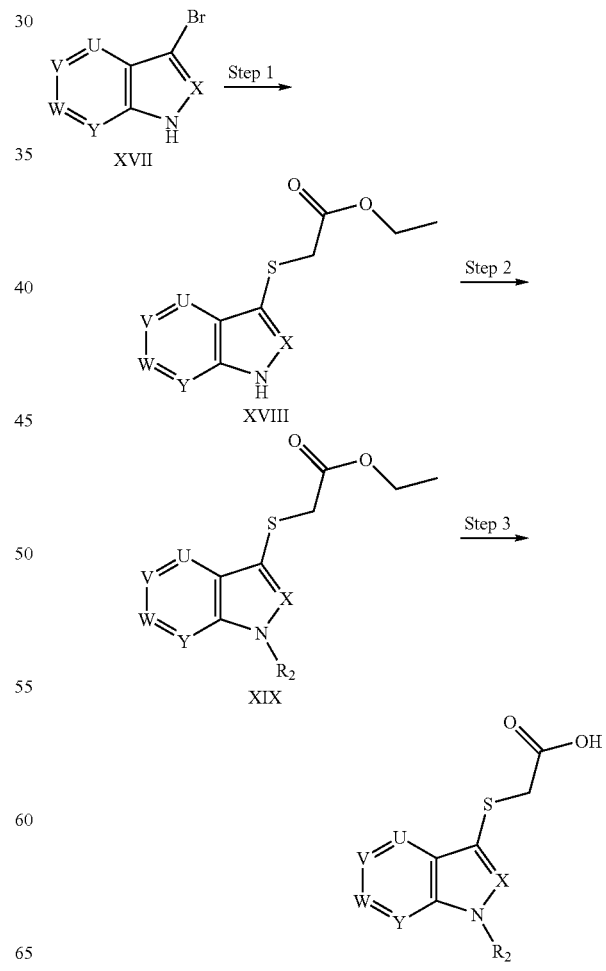

Scheme 6

Step 1—Preparation of Formula XVIII

Compound XVIII may be prepared by substituting compound of Formula XVII with ethyl 2-mercaptoacetate in the presence of base (e.g. potassium carbonate) in an inert solvent (e.g. acetone) typically for 12-18 hours with heating to reflux, followed by isolation and purification by conventional means (e.g. aqueous work-up and silica gel chromatography). (Salituro et. al., *J. Med. Chem.*, 35, 1992, 1791.)

Step 3—Preparation of Formula XIX

Compound of Formula XIII may be prepared by treating compound of Formula XII with a base (e.g. sodium hydride) in an inert solvent (e.g. DMF), followed by the addition of $R^2L_c$, where $L_c$ is a leaving group (e.g. chloro, bromo), and stirring at room temperature, typically for 16 to 24 hours, followed by isolation and purification by conventional means (e.g. aqueous work-up and silica gel chromatography).

Step 4—Preparation of Formula Ie

Compound of Formula Ie where $R^1$ is carboxylic acid and $R^3$ and $R^4$ are hydrogen may be prepared by hydrolysis of compound of Formula XIX with aqueous base (e.g. sodium hydroxide), typically for 6-18 hours, in an inert solvent (e.g. tetrahydrofuran), followed by isolation and purification by conventional means (e.g. aqueous work-up and silica gel chromatography).

Compounds of Formula If, where Q is N, may be prepared as shown in Scheme 7:

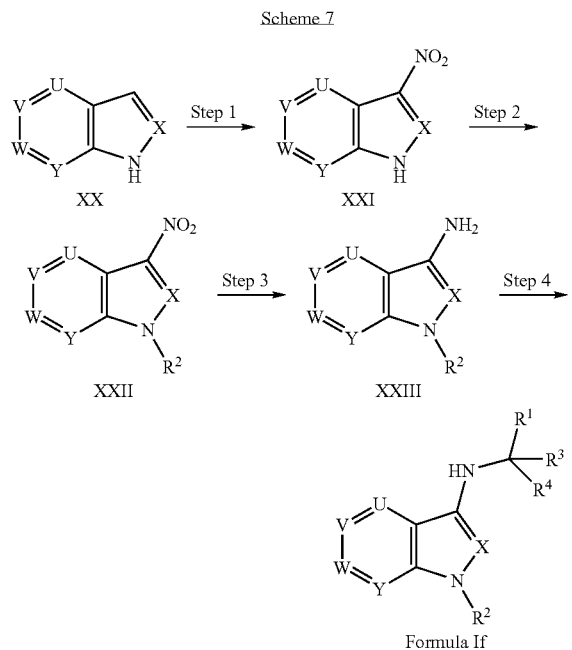

Scheme 7

Formula If

Step 1—Preparation of Formula XXI

Compound of Formula XXI may be prepared by nitration of commercially available compound of formula XX with nitric acid, in a solvent (e.g. acetic anhydride), typically at 0° C. or colder for 1 to 12 hours, followed by isolation and purification by conventional means (e.g. aqueous work-up and silica gel chromatography). (Pelkey et. al., *Synthesis*, 1999, 7:1117.)

Step 2—Preparation of Formula XXII

Compound of Formula XXII may be prepared by treating compound of Formula XXI with a base (e.g. sodium hydride) in an inert solvent (e.g. DMF), followed by the addition of $R^2L_c$, where $L_c$ is a leaving group (e.g. chloro, bromo), and stirring at room temperature, typically for 16 to 24 hours, followed by isolation and purification by conventional means (e.g. aqueous work-up and silica gel chromatography).

Step 3—Preparation of Formula XXIII

Compound of Formula XXIII may be prepared by treating compound of Formula XXII with a reducing agent (e.g. hydrogen) in the presence of a catalyst (e.g. 10% palladium on carbon) in a solvent (e.g. methanol), at room temperature, typically for 1 to 24 hours, followed by isolation and purification by conventional means (e.g. aqueous work-up and silica gel chromatography).

Step 4—Preparation of Formula If

Compound of Formula If may be prepared by treating compound of Formula XXIII, with an appropriate reagent (e.g. methyl 2-bromoacetate), containing the $R^1$, $R^3$ and $R^4$ substituents and appropriate leaving group (e.g. chloro, bromo), in the presence of base (e.g. sodium hydride) in an inert solvent (e.g. DMF) typically for 12-18 hours with heating, followed by isolation and purification by conventional means (e.g. aqueous work-up and silica gel chromatography).

In one particular embodiment of Formula If, $R^1$ is carboxylic acid and $R^3$ and $R^4$ are hydrogen, which may be prepared from intermediate XXIII according to Scheme 8.

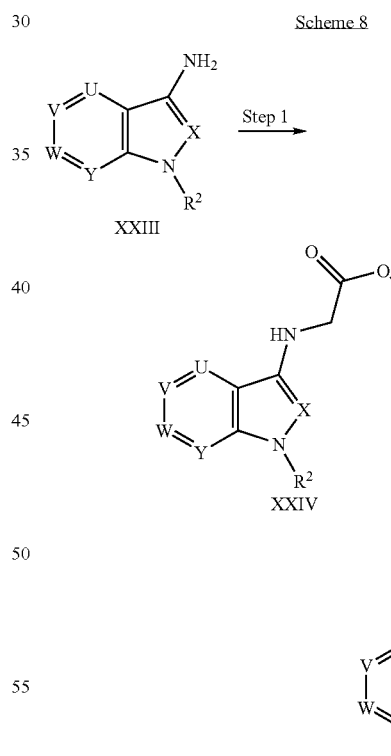

Scheme 8

Step 1—Preparation of Formula XXIV

Compound of Formula XXIV may be prepared by treating compound of Formula XXIII with methyl 2-bromoacetate in the presence of base (e.g. sodium hydride) in an inert solvent (e.g. DMF) typically for 12-18 hours with heating, followed by isolation and purification by conventional means (e.g. aqueous work-up and silica gel chromatography).

Step 2—Preparation of Formula If

Compound of Formula If wherein $R^1$ is carboxylic acid and $R^3$ and $R^4$ are hydrogen may be prepared by hydrolysis of compound of Formula XXIV with aqueous base (e.g. sodium hydroxide), typically for 6-18 hours, in an inert solvent (e.g. tetrahydrofuran), followed by isolation and purification by conventional means (e.g. aqueous work-up and silica gel chromatography).

EXAMPLES

Example 1

Synthesis of [5-Methoxy-1-(4-methoxy-benzene-sulfonyl)-1H-indol-3-yloxy]-acetic acid (1)

Indole acid 1 may be synthesized in seven steps from commercially available p-anisidine as shown in Scheme 9.

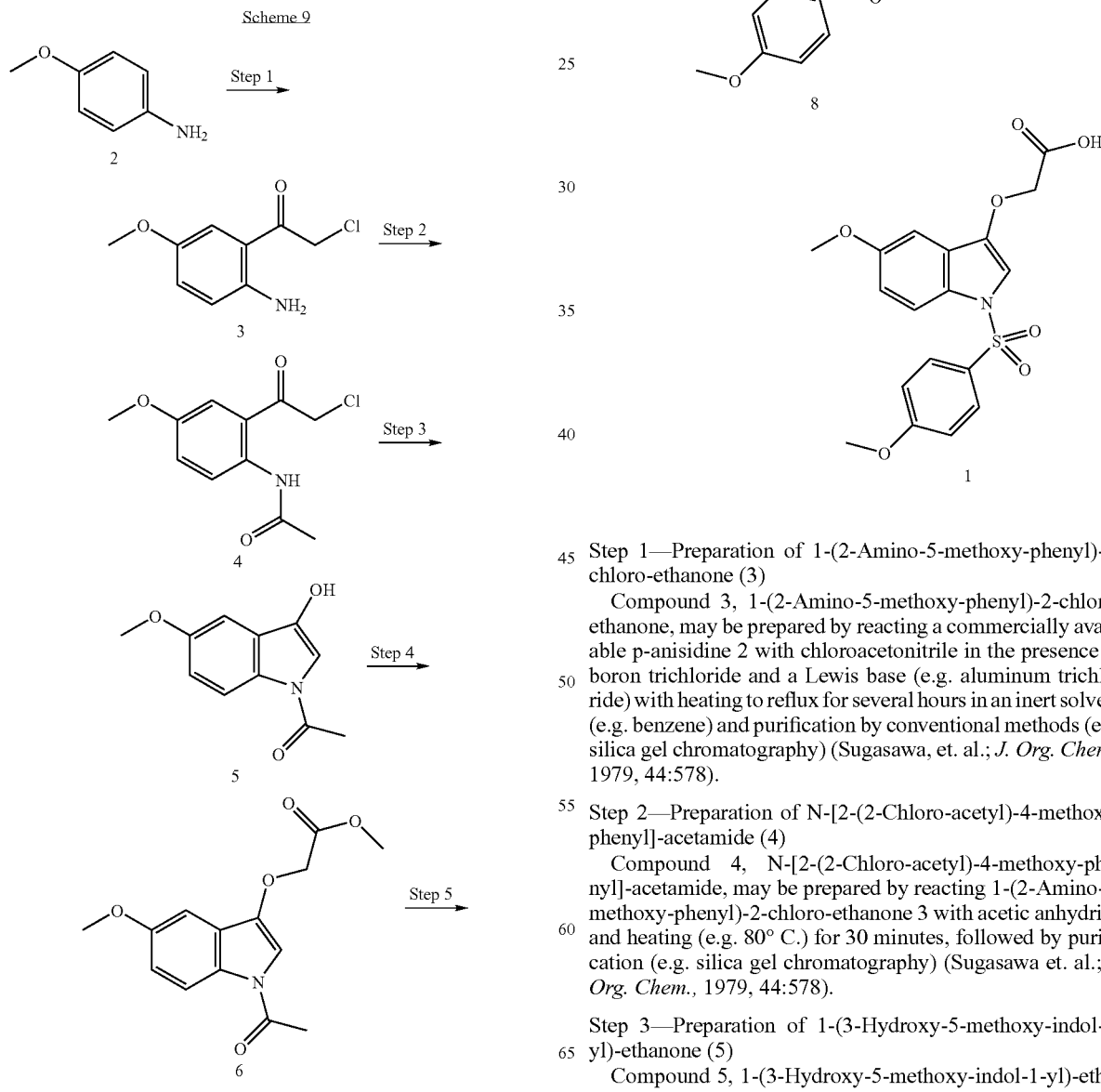

Step 1—Preparation of 1-(2-Amino-5-methoxy-phenyl)-2-chloro-ethanone (3)

Compound 3, 1-(2-Amino-5-methoxy-phenyl)-2-chloro-ethanone, may be prepared by reacting a commercially available p-anisidine 2 with chloroacetonitrile in the presence of boron trichloride and a Lewis base (e.g. aluminum trichloride) with heating to reflux for several hours in an inert solvent (e.g. benzene) and purification by conventional methods (e.g. silica gel chromatography) (Sugasawa, et. al.; *J. Org. Chem.,* 1979, 44:578).

Step 2—Preparation of N-[2-(2-Chloro-acetyl)-4-methoxy-phenyl]-acetamide (4)

Compound 4, N-[2-(2-Chloro-acetyl)-4-methoxy-phenyl]-acetamide, may be prepared by reacting 1-(2-Amino-5-methoxy-phenyl)-2-chloro-ethanone 3 with acetic anhydride and heating (e.g. 80° C.) for 30 minutes, followed by purification (e.g. silica gel chromatography) (Sugasawa et. al.; *J. Org. Chem.,* 1979, 44:578).

Step 3—Preparation of 1-(3-Hydroxy-5-methoxy-indol-1-yl)-ethanone (5)

Compound 5, 1-(3-Hydroxy-5-methoxy-indol-1-yl)-ethanone, may be prepared by reacting N-[2-(2-Chloro-acetyl)-

4-methoxy-phenyl]-acetamide 4 with a base (e.g. sodium hydride) in an inert solvent (e.g. 1,2-dimethoxyethane) and stirring with ice-cooling or at room temperature for several minutes to several hours, followed by purification and isolation by conventional means (e.g. aqueous work-up and silica gel chromatography). (Sugasawa et. al.; *J. Org. Chem.*, 1979, 44:578).

Step 4—Preparation of (1-Acetyl-5-methoxy-1H-indol-3-yloxy)-acetic acid methyl ester (6)

Compound 6, (1-Acetyl-5-methoxy-1H-indol-3-yloxy)-acetic acid methyl ester, may be prepared by alkylating 1-(3-Hydroxy-5-methoxy-indol-1-yl)-ethanone 5 with methyl 2-bromoacetate in the presence of base (e.g. potassium carbonate) in an inert solvent (e.g. acetone) typically for 12-18 hours with heating to reflux, followed by isolation and purification by conventional means (e.g. aqueous work-up and silica gel chromatography). (Andersen et. al., *J. Med. Chem.*, 1996, 39:3723.)

Step 5—Preparation of (5-Methoxy-1H-indol-3-yloxy)-acetic acid methyl ester (7)

Compound 7, (5-Methoxy-1H-indol-3-yloxy)-acetic acid methyl ester, may be prepared by removal of the N-acetyl of (1-Acetyl-5-methoxy-1H-indol-3-yloxy)-acetic acid methyl ester 6 using a base (e.g. potassium hydroxide) in methanol typically at room temperature for 2 to 24 hours, followed by isolation and purification by conventional means (e.g. aqueous work-up and silica gel chromatography). (Naylor et. al., *J. Med. Chem.*, 1997, 40:2335.)

Step 6—Preparation of [5-Methoxy-1-(4-methoxy-benzenesulfonyl)-1H-indol-3-yloxy]-acetic acid methyl ester (8)

Compound 8, [5-Methoxy-1-(4-methoxy-benzenesulfonyl)-1H-indol-3-yloxy]-acetic acid methyl ester, may be prepared by treating (5-Methoxy-1H-indol-3-yloxy)-acetic acid methyl ester 7 with 4-methoxyphenylsulfonyl chloride in a bi-phasic solvent condition (e.g. toluene and water), in presence of a base (e.g. An aqueous potassium hydroxide solution), with a phase transfer catalyst (e.g. tetrabutylammonium hydrogen sulfate), similar to conditions as described Gribble, et al., *J. Org. Chem.*, 2002, 63: 1001-03.

Step 7—Preparation of [5-Methoxy-1-(4-methoxy-benzenesulfonyl)-1H-indol-3-yloxy]-acetic acid (1)

Compound 1, [5-Methoxy-1-(4-methoxy-benzenesulfonyl)-1H-indol-3-yloxy]-acetic acid, may be prepared by hydrolysis of [5-Methoxy-1-(4-methoxy-benzenesulfonyl)-1H-indol-3-yloxy]-acetic acid methyl ester 8 with aqueous base (e.g. sodium hydroxide), typically for 6-18 hours, in an inert solvent (e.g. tetrahydrofuran), followed by isolation and purification by conventional means (e.g. aqueous work-up and silica gel chromatography).

Example 2

Synthesis of [5-Methoxy-1-(4-methoxy-benzenesulfonyl)-1H-indol-3-ylsulfanyl]-acetic acid (9)

Indole acid 9 may be synthesized from commercially available 5-methoxyindole in four steps as shown in Scheme 10.

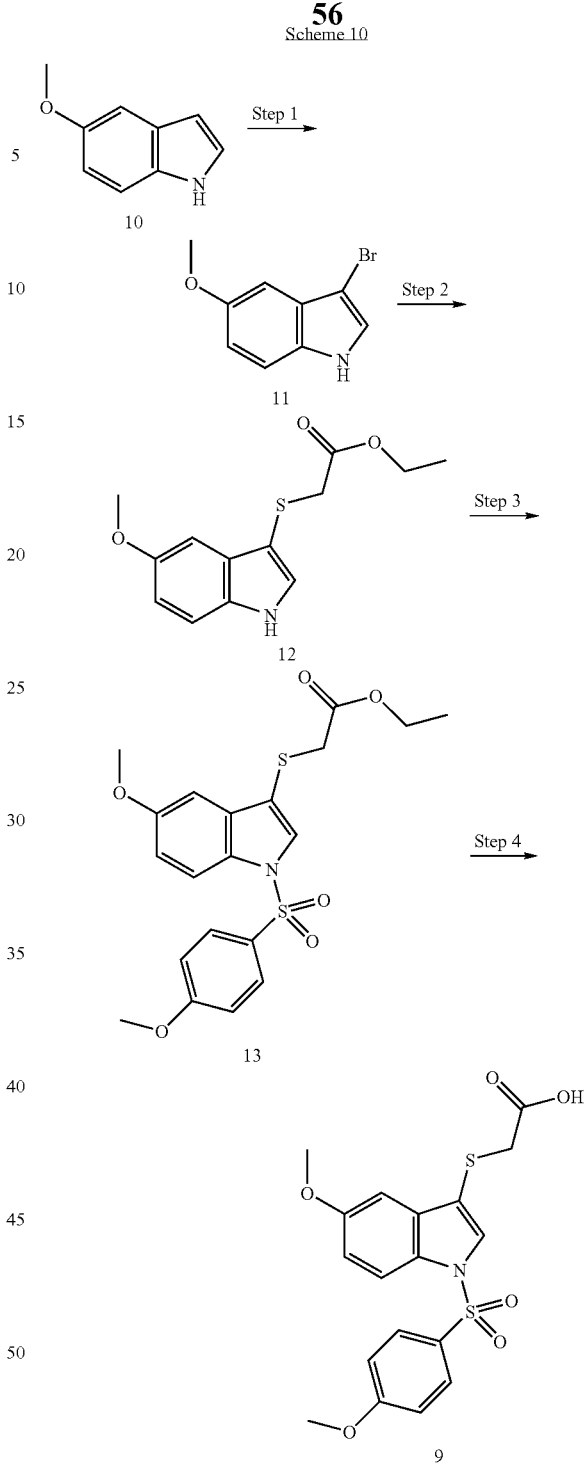

Scheme 10

Step 1—Preparation of 3-bromo-5-methoxyindole (11)

Compound 11, 3-bromo-5-methoxyindole, may be prepared by bromination of commercially available 5-methoxyindole 10 with bromine, in an inert solvent (e.g. DMF), followed by isolation and purification by conventional means (e.g. aqueous work-up and silica gel chromatography).

Step 2—Preparation of (5-Methoxy-1H-indol-3-ylsulfanyl)-acetic acid ethyl ester (12)

Compound 12, (5-Methoxy-1H-indol-3-ylsulfanyl)-acetic acid ethyl ester, may be prepared by reacting 3-bromo-5- methoxyindole 11 with ethyl 2-mercaptoacetate in the presence of base (e.g. potassium carbonate) in an inert solvent (e.g. acetone) typically for 12-18 hours with heating to reflux, followed by isolation and purification by conventional means (e.g. aqueous work-up and silica gel chromatography). (Salituro et. al., *J. Med. Chem.*, 1992, 35:1791.)

Step 3—Preparation of [5-Methoxy-1-(4-methoxy-benzenesulfonyl)-1H-indol-3-ylsulfanyl]-acetic acid ethyl ester (13)

Compound 13, [5-Methoxy-1-(4-methoxy-benzenesulfonyl)-1H-indol-3-ylsulfanyl]-acetic acid ethyl ester, may be prepared by treating (5-Methoxy-1H-indol-3-ylsulfanyl)-acetic acid ethyl ester 12 with 4-methoxyphenylsulfonyl chloride in a bi-phasic solvent condition (e.g. toluene and water), in presence of a base (e.g. An aqueous potassium hydroxide solution), with a phase transfer catalyst (e.g. tetrabutylammonium hydrogen sulfate), similar to conditions as described Gribble et al, in *J. Org. Chem.*, 2002, 63:1001-03.

Step 4—Preparation of [5-Methoxy-1-(4-methoxy-benzenesuifonyl)-1H-indol-3-ylsulfanyl]-acetic acid (9)

Compound 9, [5-Methoxy-1-(4-methoxy-benzenesulfonyl)-1H-indol-3-ylsulfanyl]-acetic acid, may be prepared by hydrolysis of [5-Methoxy-1-(4-methoxy-benzenesulfonyl)-1H-indol-3-ylsulfanyl]-acetic acid ethyl ester 13 with aqueous base (e.g. sodium hydroxide), typically for 6-18 hours, in an inert solvent (e.g. tetrahydrofuran), followed by isolation and purification by conventional means (e.g. aqueous work-up and silica gel chromatography).

Example 3

Synthesis of [5-Methoxy-1-(4-methoxy-benzenesulfonyl)-1H-indol-3-ylamino]-acetic acid (14)

Indole acid 14 may be synthesized in five steps from commercially available 5-methoxyindole as shown in Scheme 11.

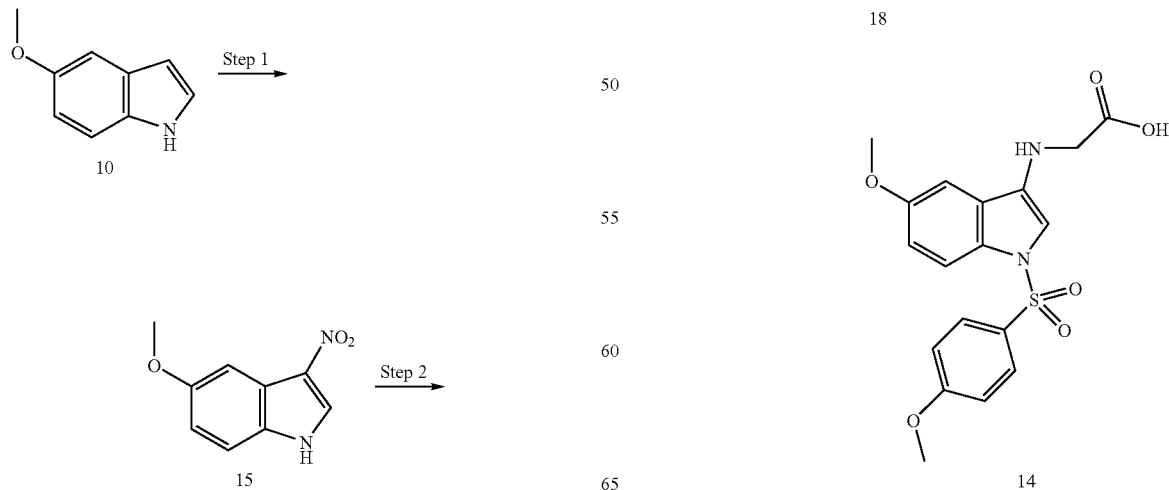

Step 1—Preparation of 5-methoxy-3-nitroindole (15)

Compound 15, 5-methoxy-3-nitroindole, may be prepared by nitration of commercially available 5-methoxyindole 10 with nitric acid, in a solvent (e.g. acetic anhydride), typically at 0° C. or colder for 1 to 12 hours, followed by isolation and purification by conventional means (e.g. aqueous work-up and silica gel chromatography). (Pelkey et. al., *Synthesis*, 1999, 7:1117.)

Step 2—Preparation of 5-Methoxy-1-(4-methoxy-benzenesulfonyl)-3-nitro-1H-indole (16)

Compound 16, 5-Methoxy-1-(4-methoxy-benzenesulfonyl)-3-nitro-1H-indole, may be prepared by treating 5-methoxy-3-nitroindole 15 with 4-methoxyphenylsulfonyl chloride in a bi-phasic solvent condition (e.g. toluene and water), in presence of a base (e.g. an aqueous potassium hydroxide solution), with a phase transfer catalyst (e.g. tetrabutylammonium hydrogen sulfate), similar to conditions as described Gribble, et al, in *J. Org. Chem.*, 2002, 63:1001-03.

Step 3—Preparation of 5-Methoxy-1-(4-methoxy-benzenesulfonyl)-1H-indol-3-ylamine (17)

Compound 17, 5-Methoxy-1-(4-methoxy-benzenesulfonyl)-1H-indol-3-ylamine, may be prepared by treating 5-Methoxy-1-(4-methoxy-benzenesulfonyl)-3-nitro-1H-indole 16 with a reducing agent (e.g. hydrogen) in the presence of a catalyst (e.g. 10% palladium on carbon) in a solvent (e.g. methanol), at room temperature, typically for 1 to 24 hours, followed by isolation and purification by conventional means (e.g. aqueous work-up and silica gel chromatography).

Step 4—Preparation of [5-Methoxy-1-(4-methoxy-benzenesulfonyl)-1H-indol-3-ylamino]-acetic acid methyl ester (18)

Compound 18, [5-Methoxy-1-(4-methoxy-benzenesulfonyl)-1H-indol-3-ylamino]-acetic acid methyl ester, may be prepared by treating 5-Methoxy-1-(4-methoxy-benzenesulfonyl)-1H-indol-3-ylamine 17, with an appropriate reagent (e.g. methyl 2-bromoacetate), containing the $R^1$, $R^3$ and $R^4$ substituents and appropriate leaving group (e.g. chloro, bromo), in the presence of base (e.g. sodium hydride) in an inert solvent (e.g. DMF) typically for 12-18 hours with heating, followed by isolation and purification by conventional means (e.g. aqueous work-up and silica gel chromatography).

Step 5—Preparation of [5-Methoxy-1-(4-methoxy-benzenesulfonyl)-1H-indol-3-ylamino]-acetic acid (14)

Compound 14, [5-Methoxy-1-(4-methoxy-benzenesulfonyl)-1H-indol-3-ylamino]-acetic acid, may be prepared by hydrolysis of [5-Methoxy-1-(4-methoxy-benzenesulfonyl)-1H-indol-3-ylamino]-acetic acid methyl ester 18 with aqueous base (e.g. sodium hydroxide), typically for 6-18 hours, in an inert solvent (e.g. tetrahydrofuran), followed by isolation and purification by conventional means (e.g. aqueous work-up and silica gel chromatography).

Example 4

Synthesis of [5-Bromo-1-(4-methoxy-benzenesulfonyl)-1H-indol-3-yloxy]-acetic acid (23)

Indole acid 23 was synthesized in four steps from commercially available 5-methoxyindole as shown in Scheme 12.

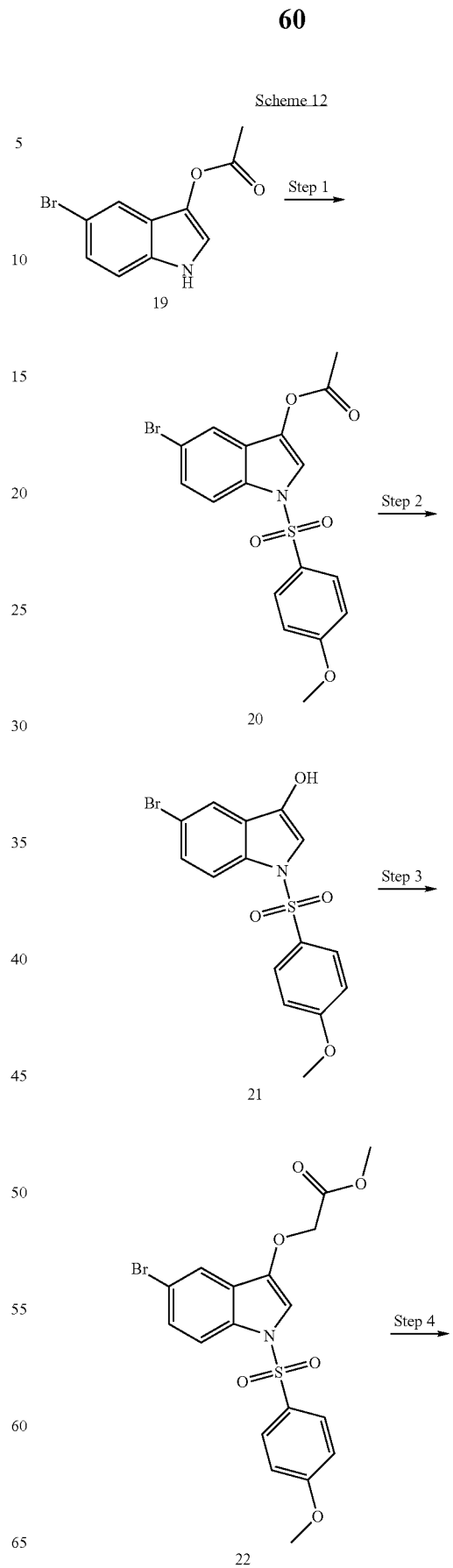

Scheme 12

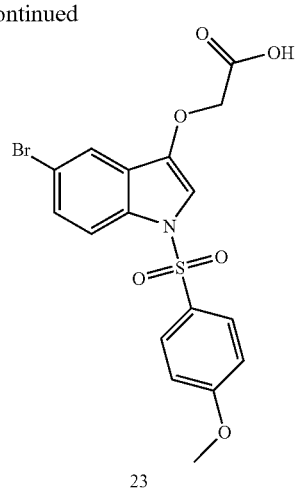

23

Step-1—Preparation of Acetic acid 5-bromo-1-(4-methoxy-benzenesulfonyl)-1H-indol-3-yl ester (20)

To a stirring solution of 5-Bromo-1H-indol-3yl ester (19, 685.0 mg, 2.70 mmol) in DMF (10.5 mL) was added sodium hydride (77.6 mg, 2.35 mmol) and the reaction mixture was stirred at 25° C. for 1 h. 4-Methoxybenzenesulfonyl chloride (612.8 mg, 2.97 mmol) was introduced and the reaction was stirred overnight under nitrogen at 25° C. Ethyl acetate was added to the reaction mixture and was washed with saturated sodium carbonate (X 5), dried over magnesium sulfate and filtered. Concentration under reduced pressure afforded the crude material, which was purified by column chromatography (20% ethyl acetate in hexanes) to yield the desired product as a white solid (20, 425 mg, 37% yield). MS(ESI) $[M+H^+]^+=424.2; 426.2$.

Step-2—Preparation of 5-Bromo-1-(4-methoxy-benzenesulfonyl)-1H-indol-3-ol (21)

Acetic acid 5-bromo-1-(4-methoxybenzenesulfonyl)-1H-indol-3-yl ester (20, 150 mg, 0.353 mmol) was added to a stirring solution of 50% potassium hydroxide (2.0 mL) in methanol (6.0 mL). After stirring at 25° C. for 30 min, the reaction mixture was acidified with 1M hydrochloric acid. The organic material was extracted with ethyl acetate, dried over magnesium sulfate, filtered and concentrated at reduced pressure to afford 5-bromo-1-(4-methoxy-benzenesulfonyl)-1H-indol-3-ol (21, 110.0 mg, 81% yield). MS(ESI) $[M-H^+]^-=380.0; 382.0$ Step-3—Preparation of [5-Bromo-1-(4-methoxy-benzenesuifonyl)-1H-indol-3-yloxy]-acetic acid methyl ester (22)

To a stirring solution of 5-bromo-1-(4-methoxy-benzenesulfonyl)-1H-indol-3-ol (21, 130 mg, 0.340 mmol) in acetonitrile (3.5 mL) in a high pressure reaction vessel was added potassium carbonate (235 mg, 1.70 mmol) and bromoacetic acid methyl ester (38.6 µL, 0.408 mmol). The vessel was flushed with a nitrogen atmosphere, sealed with a Teflon stopcock and heated to 80° C. for overnight. After the reaction mixture was cooled to 25° C., ethyl acetate was added and washed with saturated sodium bicarbonate. The organic layer was dried over magnesium sulfate, filtered and concentrated at reduced pressure to obtain a light brown solid. Purification of the crude material was carried out using biotage chromatography (30% ethyl acetate in hexanes) which afforded the product as an off-white solid (22, 72.0 mg, 47% yield). MS(ESI) $[M+H^+]^+=454.2; 456.2$.

Step-4—Preparation of [5-Bromo-1-(4-methoxy-benzenesuifonyl)-1H-indol-3-yloxy]-acetic acid (23)

[5-Bromo-1-(4-methoxy-benzenesulfonyl)-1H-indol-3-yloxy]-acetic acid methyl ester (22, 32.0 mg, 0.007 mmol) was dissolved in THF (1.50 mL) and 1M lithium hydroxide (0.4 mL) was added to this solution. After stirring for 30 min at 25° C., ethyl acetate was added and the mixture was acidified with 1M hydrochloric acid. The organic layer was dried over magnesium sulfate, filtered and concentrated at reduced pressure to obtain a white solid (23, 28 mg, 90% yield). MS(ESI) $[M-H^+]^-=438.0; 440.0$.

Example 5

Synthesis of 3-[5-Bromo-1-(4-methoxy-benzenesulfonyl)-1H-indol-3-yloxy]-propionic acid 24

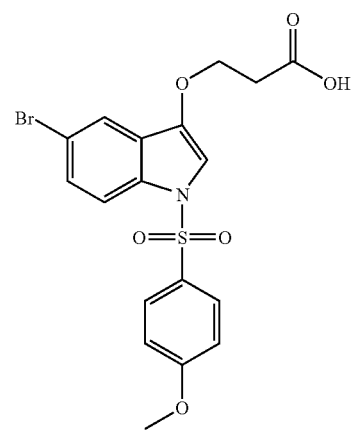

24

3-[5-Bromo-1-(4-methoxy-benzenesulfonyl)-1H-indol-3-yloxy]-propionic acid 24 was prepared using the same protocol as described in Example 4, substituting bromoacetic acid methyl ester with bromopropionic acid methyl ester in step 3. MS(ESI) $[M+H^+]^+=452.0; 454.0$.

Example 6

Synthesis of [1-(3,4-dichloro-benzenesulfonyl)-5-methoxy-1H-indol-3-ylsulfanyl]-acetic acid 27

Indole acid 27 was synthesized from commercially available 5-methoxyindole 10 in three steps as shown in Scheme 13.

Scheme 13.

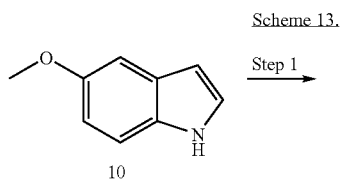

10

-continued

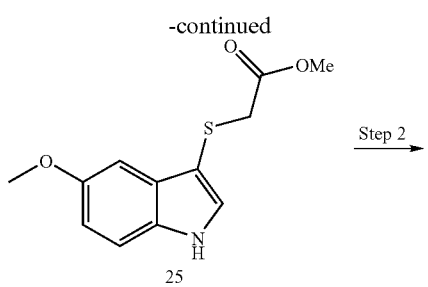

25

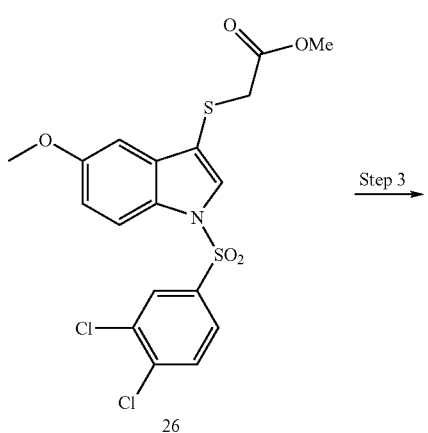

26

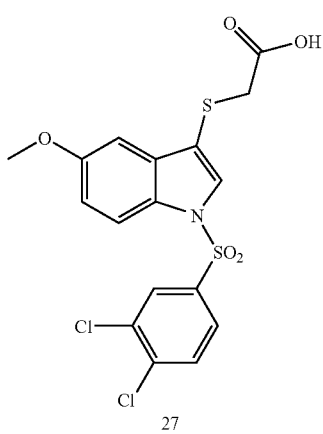

27

Step 1: Preparation of (5-Methoxy-1H-indol-3-ylsulfanyl)-acetic acid methyl ester (25)

Triiodide synthesis: Into a round bottom flask, KI (5.00 g, 30.1 mmol) was mixed with $I_2$ (5.1 g, 20.0 mmol) in 20 mL water. The mixture was stirred at room temperature for 24 hours. To a solution of 5-methoxyindole (10, 200 mg, 1.36 mmol) and thiourea (110 mg, 1.44 mmol) in methanol (10 mL), triiodide, freshly prepared from the previous day (440 mg, 1.5 mmol) was added over a 20 minute period, and the combined mixture stirred at room temperature for 40 min. The solvent was reduced to half of its volume and 10 N NaOH (5 mL) was added to the flask and heated at 95° C. for one hour under an inert atmosphere. The resulting suspension was filtered hot and the solid rinsed with water. Filtrate was cooled to room temperature and bromoacetic acid methyl ester (241 mg, 1.6 mmol) was added. This mixture was stirred vigorously for an hour and the organic layer was extracted with diethyl ether. The aqueous layer was acidified with 1 N HCl and extracted with ether. The desired product was isolated after flash silica column chromatography using gradient solvent 5-10% EtOAc/hexane. (15 mg, 4.4%)

Step 2. Preparation of [1-(3,4-dichloro-benzenesulfonyl)-5-methoxy-1H-indol-3-ylsulfanyl]-acetic acid methyl ester (26)

To a dry round bottom flask, (5-Methoxy-1H-indol-3-ylsulfanyl)-acetic acid methyl ester (25, 7.0 mg, 0.027 mmol) was dissolved with $CH_2Cl_2$ (3.0 mL). Tetrabutylammonium hydrogen sulfate (2.0 mg) and 50% KOH solution (3.0 mL) were added next. After about 5 minutes of stirring, 3,4-dichloro-benzenesulfonyl chloride (20 mg, 0.081 mmol) was added. This reaction was allowed to stir at ambient temperature overnight. The reaction was extracted with dichloromethane (2×14 mL), washed with water (5 mL), brine (5 mL) and dried over anhydrous magnesium sulfate. The reactant was filtered and rotoevaporated to give the desired product 26 as off white solid.

Step 3: Preparation of [1-(3,4-dichloro-benzenesulfonyl)-5-methoxy-1H-indol-3-ylsulfanyl]-acetic acid (27)

To a solution of (5-Methoxy-1H-indol-3-ylsulfanyl)-acetic acid methyl ester 26, in THF (4.0 mL) was added an aqueous solution of potassium hydroxide (1.0 mL of 1M) which was stirred at room temperature for 4 h. The acid was neutralized with aqueous HCl, extracted the product with ethyl acetate, dried over anhydrous magnesium sulfate, evaporated under reduced pressure, and purified via trituration with tetrabutyl ethyl ether to afford 27 as a white solid (4.5 mg, 5%). MS(ESI) $[M+H^-]^+=443.95$ Example 7

Synthesis of (5-methoxy-1H-indol-3-ylsulfanyl)-acetic acid 28

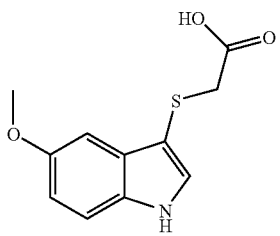

(5-methoxy-1H-indol-3-ylsulfanyl)-acetic acid 28 was prepared by reacting (5-Methoxy-1H-indol-3-ylsulfanyl)-acetic acid methyl ester 25 using the same protocol as described in Example 6 step 3 to give 28 as an acid. MS(ESI) $[M-H^+]^-=238.15$

Example 8

Synthesis of 3-[5-Bromo-1-(4-methoxy-benzene-sulfonyl)-1H-indol-3-yloxy]-propionic acid methyl ester (29)

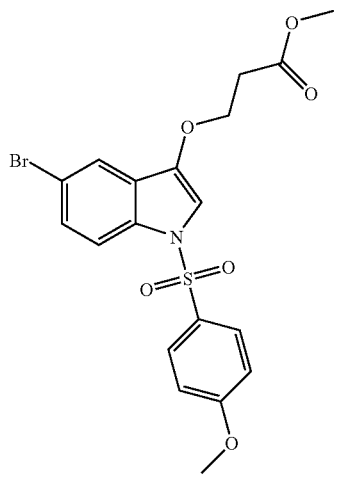

3-[5-Bromo-1-(4-methoxy-benzenesulfonyl)-1H-indol-3-yloxy]-propionic acid methyl ester was prepared using the same protocol as described in Example 4, substituting bromoacetic acid methyl ester with bromopropionic acid methyl ester in step 3. MS(ESI) [M−H$^+$]$^-$=466.0; 468.0

Example 9

Expression and Purification of PPARs For Use in Biochemical and Cell Assays

Genetic Engineering

Plasmids encoding the Ligand-binding domains (LBDs) of PPARα, PPARγ, and PPARδ were engineered using common polymerase chain reaction (PCR) methods (pGal4-PPARα-LBD, pGal4-PPARγ-LBD, pGal4-PPARδ-LBD). The relevant DNA sequences and encoded protein sequences used in the assay are shown for each (see below). Complementary DNA cloned from various human tissues was purchased from Invitrogen, and these were used as substrates in the PCR reactions. Specific custom synthetic oligonucleotide primers (Invitrogen, see below) were designed to initiate the PCR product, and also to provide the appropriate restriction enzyme cleavage sites for ligation with the plasmids.

The plasmids used for ligation with the receptor-encoding inserts were either pET28 (Novagen) or a derivative of pET28, pET-BAM6, for expression using *E. coli*. In each of these cases the receptor LBD was engineered to include a Histidine tag for purification using metal affinity chromatography.

Protein Expression and Purification of PPAR's.

For protein expression, plasmids containing genes of interest were transformed into *E. coli* strain BL21(DE3)RIL (Invitrogen) and transformants selected for growth on LB agar plates containing appropriate antibiotics. Single colonies were grown for 4 hrs at 37° C. in 200 ml LB media. For PPARα and PPARγ all protein expression was performed by large scale fermentation using a 30 L bioreactor. 400 ml of starter culture was added to 30 L TB culture and allowed to grow at 37° C. until an OD 600 nm of 2-5 was obtained. The culture was cooled to 20° C. and 0.5 mM IPTG (isopropyl-beta-D-thiogalactopyranoside) added, and the culture was allowed to grow for a further 18 hrs.

For PPARδ protein expression, single colonies were grown for 4 hrs at 37° C. in 200 mL LB media. 16×1 L of fresh TB media in 2.8 L flasks were inoculated with 10 mL of starter culture and grown with constant shaking at 37° C. Once cultures reached an absorbance of 1.0 at 600 nm, an additive to improve the solubility of the PPARδ was added to the culture and 30 min later, 0.5 mM IPTG was added and cultures allowed to grow for a further 12 to 18 hrs at 20° C. Cells were harvested by centrifugation and pellets frozen at −80° C. until ready for lysis/purification.

For protein purification; all operations were carried out at 4° C. Frozen *E. coli* cell pellets were resuspended in lysis buffer and lysed using standard mechanical methods. Soluble proteins were purified via poly-Histidine tags using immobilized metal affinity purification (IMAC). For each of the PPAR's described all have been purified using a 3 step purification process utilizing; IMAC, size exclusion chromatography and ion exchange chromatography. For PPARα the poly-Histidine tag was optionally removed using Thrombin (Calbiochem). In the case of PPARδ, during protein purification the solubility improving additive was present in order to maintain protein stability. During the final step of purification solubility improving additives were desalted away before concentration.

Plasmid Sequence and PCR Primer Information

```
PPARα(SEQ ID NOS: 1 and 2 respectively in order
of appearance):
  P332. pET28 PPARA E199-Y468-X
                                     taatacgactcactatagggggaattgt
    gagcggataacaattcccctctagaaataattttgtttaactttaagaaggagatatacc
    atgggcagcagccatcatcatcatcatcacagcagcggcctggtgccgcgcggcagccat
     M   G   S   S   H   H   H   H   H   H   S   S   G   L   V   P   R   G   S   H
    atggaaactgcagatctcaaatctctggccaagagaatctacgaggcctacttgaagaac
     M   E   T   A   D   L   K   S   L   A   K   R   I   Y   E   A   Y   L   K   N
    ttcaacatgaacaaggtcaaagcccgggtcatcctctcaggaaaggccagtaacaatcca
     F   N   M   N   K   V   K   A   R   V   I   L   S   G   K   A   S   N   N   P
    ccttttgtcatacatgatatggagacactgtgtatggctgagaagacgctggtggccaag
     P   F   V   I   H   D   M   E   T   L   C   M   A   E   K   T   L   V   A   K
    ctggtggccaatggcatccagaacaaggaggcggaggtccgcatctttcactgctgccag
     L   V   A   N   G   I   Q   N   K   E   A   E   V   R   I   F   H   C   C   Q
    tgcacgtcagtggagaccgtcacggagctcacggaattcgccaaggccatcccaggcttc
     C   T   S   V   E   T   V   T   E   L   T   E   F   A   K   A   I   P   G   F
    gcaaacttggacctgaacgatcaagtgacattgctaaaatacggagtttatgaggccata
```

```
                      A  N  L  D  L  N  D  Q  V  T  L  L  K  Y  G  V  Y  E  A  I
ttcgccatgctgtcttctgtgatgaacaaagacgggatgctggtagcgtatggaaatggg
                      F  A  M  L  S  S  V  M  N  K  D  G  M  L  V  A  Y  G  N  G
tttataactcgtgaattcctaaaaagcctaaggaaaccgttctgtgatatcatggaaccc
                      F  I  T  R  E  F  L  K  S  L  R  K  P  F  C  D  I  M  E  P
aagtttgattttgccatgaagttcaatgcactggaactggatgacagtgatatctccctt
                      K  F  D  F  A  M  K  F  N  A  L  E  L  D  D  S  D  I  S  L
tttgtggctgctatcatttgctgtggagatcgtcctggccttctaaacgtaggacacatt
                      F  V  A  A  I  I  C  C  G  D  R  P  G  L  L  L  N  V  G  H  I
gaaaaaatgcaggagggtattgtacatgtgctcagactccacctgcagagcaaccacccg
                      E  K  M  Q  E  G  I  V  H  V  L  R  L  H  L  Q  S  N  H  P
gacgatatctttctcttcccaaaacttcttcaaaaaatggcagacctccggcagctggtg
                      D  D  I  F  L  F  P  K  L  L  Q  K  M  A  D  L  R  Q  L  V
acggagcatgcgcagctggtgcagatcatcaagaagacggagtcggatgctgcgctgcac
                      T  E  H  A  Q  L  V  Q  I  I  K  K  T  E  S  D  A  A  L  H
ccgctactgcaggagatctacagggacatgtactgagtcgacaagcttgcggccgcactc
                      P  L  L  Q  E  I  Y  R  D  M  Y  -
Gagcaccaccaccaccactgagat PCR primers: (SEQ ID NOS: 3 and 4, respectively in order
of appearance):
    PPARA  PPARA-S  GCTGACACATATGGAAACTGCAGATCTCAAATC  343
           PPARA-A  GTGACTGTCGACTCAGTACATGTCCCTGTAGA    344

PPARγ(SEQ ID NOS: 5 and 6, respectively in order
of appearance):
P333. pET28 PPARG E205-Y475-X
                                       taatacgactcactatagggggaattgt
gagcggataacaattcccctctagaaataattttgtttaactttaagaaggagatatacc
atgggcagcagccatcatcatcatcatcacagcagcggcctggtgccgcgcggcagccat
M  G  S  S  H  H  H  H  H  H  S  S  G  L  V  P  R  G  S  H
atggagtccgctgacctccgggccctggcaaaacatttgtatgactcatacataaagtcc
M  E  S  A  D  L  R  A  L  A  K  H  L  Y  D  S  Y  I  K  S
ttcccgctgaccaaagcaaaggcgagggcgatcttgacaggaaagacaacagacaaatca
F  P  L  T  K  A  K  A  R  A  I  L  T  G  K  T  T  D  K  S
ccattcgttatctatgacatgaattccttaatgatgggagaagataaaatcaagttcaaa
P  F  V  I  Y  D  M  N  S  L  M  M  G  E  D  K  I  K  F  K
cacatcaccccctgcaggagcagagcaaagaggtggccatccgcatctttcagggctgc
H  I  T  P  L  Q  E  Q  S  K  E  V  A  I  R  I  F  Q  G  C
cagtttcgctccgtggaggctgtgcaggagatcacagagtatgccaaaagcattcctggt
Q  F  R  S  V  E  A  V  Q  E  I  T  E  Y  A  K  S  I  P  G
tttgtaaatcttgacttgaacgaccaagtaactctcctcaaatatggagtccacgagatc
F  V  N  L  D  L  N  D  Q  V  T  L  L  K  Y  G  V  H  E  I
atttacacaatgctggcctccttgatgaataaagatggggttctcatatccgagggccaa
I  Y  T  M  L  A  S  L  M  N  K  D  G  V  L  I  S  E  G  Q
ggcttcatgacaagggagtttctaaagagcctgcgaaagcctttggtgactttatggag
G  F  M  T  R  E  F  L  K  S  L  R  K  P  F  G  D  F  M  E
cccaagtttgagtttgctgtgaagttcaatgcactggaattagatgacagcgacttggca
P  K  F  E  F  A  V  K  F  N  A  L  E  L  D  D  S  D  L  A
atatttattgctgtcattattctcagtggagaccgcccaggtttgctgaatgtgaagccc
I  F  I  A  V  I  I  L  S  G  D  R  P  G  L  L  N  V  K  P
attgaagacattcaagacaacctgctacaagccctggagctccagctgaagctgaaccac
I  E  D  I  Q  D  N  L  L  Q  A  L  E  L  Q  L  K  L  N  H
cctgagtcctcacagctgtttgccaagctgctccagaaaatgacagacctcagacagatt
P  E  S  S  Q  L  F  A  K  L  L  Q  K  M  T  D  L  R  Q  I
gtcacggaacatgtgcagctactgcaggtgatcaagaagacggagacagacatgagtctt
V  T  E  H  V  Q  L  L  Q  V  I  K  K  T  E  D  M  S  L
cacccgctcctgcaggagatctacaaggacttgtactaggtcgacaagcttgcggccgca
H  P  L  L  Q  E  I  Y  K  D  L  Y  -
ctcgagcaccaccaccaccactgagat PCR Primers: (SEQ ID NOS: 7 and 8, respectively in order
of appearance):
    PPARG  PPARG-S  GCTCAGACATATGGAGTCCGCTGACCTCCGGGC  347
           PPARG-A  GTGACTGTCGACCTAGTACAAGTCCTTGTAGA    348

PPARδ(SEQ ID NOS: 9 and 10, respectively in order
of appearance:
P1057. pET BAM6 PPARD G165-Y441-X
                                       taatacgactcactatagggggaattgt
gagcggataacaattcccctctagaaataattttgtttaactttaagaaggagatatacc
atgaaaaaaggtcaccaccatcaccatcacggatcccagtacaacccacaggtggccgac
M  K  K  G  H  H  H  H  H  H  G  S  Q  Y  N  P  Q  V  A  D
ctgaaggccttctccaagcacatctacaatgcctacctgaaaaacttcaacatgaccaaa
L  K  A  F  S  K  H  I  Y  N  A  Y  L  K  N  F  N  M  T  K
aagaaggcccgcagcatcctcaccggcaaagccagccacacggcgcccttgtgatccac
K  K  A  R  S  I  L  T  G  K  A  S  H  T  A  P  F  V  I  H
gacatcgagacattgtggcaggcagagaagggctggtgtggaagcagttggtgaatggc
D  I  E  T  L  W  Q  A  E  K  G  L  V  W  K  Q  L  V  N  G
ctgcctccctacaaggagatcagcgtgcacgtcttctaccgctgccagtgcaccacagtg
```

```
                               -continued
  L   P   P   Y   K   E   I   S   V   H   V   F   Y   R   C   Q   C   T   T   V
gagaccgtgcgggagctcactgagttcgccaagagcatcccagcttcagcagcctcttc
  E   T   V   R   E   L   T   E   F   A   K   S   I   P   S   F   S   S   L   F
ctcaacgaccaggttacccttctcaagtatggcgtgcacgaggccatcttcgccatgctg
  L   N   D   Q   V   T   L   L   K   Y   G   V   H   E   A   I   F   A   M   L
gcctctatcgtcaacaaggacgggctgctggtagccaacggcagtggctttgtcacccgt
  A   S   I   V   N   K   D   G   L   L   V   A   N   G   S   G   F   V   T   R
gagttcctgcgcagcctccgcaaaccttcagtgatatcattgagcctaagtttgaattt
  E   F   L   R   S   L   R   K   P   F   S   D   I   I   E   P   K   F   E   F
gctgtcaagttcaacgccctggaacttgatgacagtgacctggccctattcattgcggcc
  A   V   K   F   N   A   L   E   L   D   D   S   D   L   A   L   F   I   A   A
atcattctgtgtggagaccggccaggcctcatgaacgttccacgggtggaggctatccag
  I   I   L   C   G   D   R   P   G   L   M   N   V   P   R   V   E   A   I   Q
gacaccatcctgcgtgccctcgaattccacctgcaggccaaccacccctgatgcccagtac
  D   T   I   L   R   A   L   E   F   H   L   Q   A   N   H   P   D   A   Q   Y
ctcttccccaagctgctgcagaagatggctgacctgcggcaactggtcaccgagcacgcc
  L   F   P   K   L   L   Q   K   M   A   D   L   R   Q   L   V   T   E   H   A
cagatgatgcagcggatcaagaagaccgaaaccgagacctcgctgcaccctctgctccag
  Q   M   M   Q   R   I   K   K   T   E   T   E   T   S   L   H   P   L   L   Q
gagatctacaaggacatgtactaagtcgaccaccaccaccaccaccactgagatccggct
  E   I   Y   K   D   M   Y   -
ggccctactggccgaaaggaattcgaggccagcagggccaccgctgagcaataactagca
taaccccttggggcctctaaacgggtcttgaggggtttttttg PCR Primers (SEQ ID NOS: 11 and 12, respectively in order
of appearance):
  PPARD   PPARD-    GTTGGATCCCAGTACAACCCACAGGTGGC       2313
          G165
          PPARB-A   GTGACTGTCGACTTAGTACATGTCCTTGTAGA    346
```

Example 10

Biochemical Screening

The homogenous Alpha screen assay was used in the agonist mode to determine the ligand dependent interaction of the PPARs (α,δ,γ) with the coactivator Biotin-PGC-1 peptide (biotin-AHX-DGTPPPQEAEEPSLLKKLLLAPANT-CONH$_2$ (SEQ ID NO: 13), supplied by Wyeth). Compounds 23, 24, 27 and 29 from Table 1 were serially diluted 1:3 into DMSO for a total of 8 concentration points. Samples were prepared with His-tagged PPAR-LBD prepared per Example 9. Ni-chelate acceptor beads were added that bind to the his-tagged PPAR-LBD and streptavidin donor beads were added that bind to the biotin of the coactivator (Perkin-Elmer #6760619M) such that agonist activity correlates to signal from the donor and acceptor beads in close proximity. Each sample was prepared by mixing 1 μl of compound and 15 μl of 1.33×receptor/peptide mix, incubating for 15 minutes at room temperature, then adding 4 μl of 4×beads in assay buffer. The assay buffer was 50 mM HEPES, pH 7.5, 50 mM KCl, 1 mM DTT and 0.8% BSA. Final concentrations for each sample were 25 nM biotin-PGC-1 peptide, 20 nM PPARγ or 10 nM PPARα or δ, and each bead at 5 μg/ml, with compound added to the desired concentration resulting in final DMSO of 5%. WY-14643(PPARα), farglitazar (PPARγ) and bezafibrate (PPARδ) were assayed as control samples. The samples were incubated for 1 hour in the dark at room temperature before taking the reading in the Fusion alpha or Alpha Quest reader. The signal vs. compound concentration was used to determine the EC$_{50}$. The data was expressed in μMol/L. The data points from the Fusion alpha instrument were transferred to Assay Explorer® (MDL) to generate a curve and calculate the inflection point of the curve as EC$_{50}$. Compound 27 demonstrated EC$_{50}$ of <1 μM with respect to PPARδ and PPARγ.

Example 11

Co-Transfection Assay

This assay serves to confirm the observed biochemical activity (Example 10) on the modulation of intended target molecule(s) at the cellular level. 293T cells (ATCC) are seeded at 1-2×10$^6$ cells per well of a 6 well plate (Corning 3516) in 3 ml of growth medium (Dulbecco's eagle medium, Mediatech, with 10% FBS). These are incubated to 80-90% confluent and the medium is removed by aspirating. These cells are transfected with PPAR LBD and luciferase such that agonist will result in activation of the luciferase. Measurement of luciferase activity of transfected cells treated with test compounds directly correlates with agonist activity. To 100 μl of serum free growth medium is added 1 μg of pFR-Luc (Stratagene catalog number 219050), 6 μl Metafectene (Biontex, Inc.) and 1 mg of the pGal4-PPAR-LBD(α, γ or δ from Example 9). This is mixed by inverting, then incubated for 15-20 minutes at room temperature, then diluted with 900 μl of serum free growth medium. This is overlayed onto the 293T cells and incubated for 4-5 hours at 37° C. in CO$_2$ incubator. The transfection medium is removed by aspirating and growth medium is added and the cells incubated for 24 hours. The cells are then suspended in 5 ml of growth medium and diluted with an additional 15 ml of growth medium. For each test sample, 95 μl of the transfected cells are transferred per well of a 96 well culture plate. Compounds for testing are made up in DMSO at 200× the desired final concentration. This is diluted 10× with growth medium and 5 μl is added to the 95 μl of transfected cells. The plate is incubated for 24 hours 37° C. in CO$_2$ incubator. Luciferase reaction mixture is prepared by mixing 1 ml of lysis buffer, 1 ml of substrate in lysis buffer, and 3 ml of reaction buffer (Roche Diagnostics Luciferase assay kit #1814036). For each sample well, the growth medium is replaced with 50 ml of reaction mixture and the plate shaken for 15-20 minutes, and the luminescence was measured on a Victor2 V plate reader (Perkin Elmer). The signal vs. compound concentration is used to determine the EC$_{50}$.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to exemplary compounds of Formula I, Ia, Ib, or Ic to provide additional active compounds. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

```
SEQ ID NO:__: NM_005036
   1 gcgccgcctc cttcggcgtt cgccccacgg accggcaggc ggcggaccgc ggcccaggct
  61 gaagctcagg gccctgtctg ctctgtggac tcaacagttt gtggcaagac aagctcagaa
 121 ctgagaagct gtcaccacag ttctggaggc tgggaagttc aagatcaaag tgccagcaga
 181 ttcagtgtca tgtgaggacg tgcttcctgc ttcatagata agagtagctt ggagctcggc
 241 ggcacaacca gcaccatctg gtcgcgatgg tggacacgga aagcccactc tgccccctct
 301 ccccactcga ggccggcgat ctagagagcc cgttatctga agagttcctg caagaaatgg
 361 gaaacatcca agagatttcg caatccatcg gcgaggatag ttctggaagc tttggcttta
 421 cggaatacca gtatttagga agctgtcctg gctcagatgg ctcggtcatc acggacacgc
 481 tttcaccagc ttcgagcccc tcctcggtga cttatcctgt ggtccccggc agcgtggacg
 541 agtctcccag tggagcattg aacatcgaat gtagaatctg cggggacaag gcctcaggct
 601 atcattacgg agtccacgcg tgtgaaggct gcaagggctt ctttcggcga acgattcgac
 661 tcaagctggt gtatgacaag tgcgaccgca gctgcaagat ccagaaaaag aacagaaaca
 721 aatgccagta ttgtcgattt cacaagtgcc tttctgtcgg gatgtcacac aacgcgattc
 781 gttttggacg aatgccaaga tctgagaaag caaaactgaa agcagaaatt cttacctgtg
 841 aacatgacat agaagattct gaaactgcag atctcaaatc tctggccaag agaatctacg
 901 aggcctactt gaagaacttc aacatgaaca aggtcaaagc ccgggtcatc ctctcaggaa
 961 aggccagtaa caatccacct tttgtcatac atgatatgga gacactgtgt atggctgaga
1021 agacgctggt ggccaagctg gtggccaatg gcatccagaa caaggaggcg gaggtccgca
1081 tctttcactg ctgccagtgc acgtcagtgg agaccgtcac ggagctcacg gaattcgcca
1141 aggccatccc aggcttcgca aacttggacc tgaacgatca agtgacattg ctaaaatacg
1201 gagtttatga ggccatattc gccatgctgt cttctgtgat gaacaaagac gggatgctgg
1261 tagcgtatgg aaatgggttt ataactcgtg aattcctaaa aagcctaagg aaaccgttct
1321 gtgatatcat ggaacccaag tttgattttg ccatgaagtt caatgcactg gaactggatg
1381 acagtgatat ctccctttt gtggctgcta tcatttgctg tggagatcgt cctggccttc
1441 taaacgtagg acacattgaa aaaatgcagg agggtattgt acatgtgctc agactccacc
1501 tgcagagcaa ccaccggac gatatctttc tcttcccaaa acttcttcaa aaaatggcag
1561 acctccggca gctggtgacg gagcatgcgc agctggtgca gatcatcaag aagacggagt
1621 cggatgctgc gctgcacccg ctactgcagg agatctacag ggacatgtac tgagttcctt
1681 cagatcagcc acacctttc caggagttct gaagctgaca gcactacaaa ggagacgggg
1741 gagcagcacg attttgcaca aatatccacc actttaacct tagagcttgg acagtctgag
1801 ctgtaggtaa ccggcatatt attccatatc tttgttttaa ccagtacttc taagagcata
1861 gaactcaaat gctgggggta ggtggctaat ctcaggactg ggaagattac ggcgaattat
1921 gctcaatggt ctgattttaa ctcacccgat gttaatcaat gcacattgct ttagatcaca
1981 ttcgtgattt accatttaat taactggtaa cctcaaaatt cgtggcctgt cttcccattc
2041 accccgcttt tgactattgt gctcctttat aattctgaaa actaatcagc acttttaac
2101 aatgtttata atcctataag tctagatgta tccaaaggtg aagtatgtaa aaagcagcaa
2161 aatatttatt tcaaagactt cacttctgtt tcctgaatct aaagaaagac aacatgctgc
2221 tttttaatca taggatggga aattttaaag aactgtttgg gccaggcaca gtcgctcata
2281 cttgtaatcc cagcactttg ggaggccgag gcgggtggat cacaaggtca gcagatcgag
2341 accatcctgg ccaacatggt gaaaccctgt ctctactaaa aatacaaaaa ttagccgggt
2401 gtggtggcac atgcctgtaa tcccagctac tcgggaagct gaggcaggag aattgcttga
2461 accagggagt tggaggttgc agtgagctaa gactgcacca ctgcactcca gcctggtgac
2521 agaacgagac tctgtcttaa aaacaaacaa acaaaaaaaa aatctgttag ataagctatc
```

```
-continued
2581 aaaatgcagc tgttgttttg tttttggctc actgtttteg tggttgtaac taatatgtgg
2641 aaaggcccat ttccaggttt gcgtagaaga gcccagaaaa cagagtctca agaccccgc
2701 tctggactgt cataagctag cacccgtggt aagcgggacg agacaagctc ccgaagcccg
2761 ccagcttcct gctccactca gctccgtcca gtcaacctga acccacccag tccagctgtc
2821 tgtgggaatg gtggtgttct tagggacaga ctgacacctt acttgtcagt gttcctccgg
2881 gccccatttg gcagctcccg tatctttttgt tatgttgctt ttaaagatat gatgttttat
2941 tgttttaact cttggtgaca gtagatgctc tctggagcgc agactgaggca catgtgtctt
3001 catagcctgg gctgggtggg agccagtcac cctgcggatc gagagagggg gtagagtctt
3061 cttcaaatgg cagtttact tcaaatgca gatttcacaa gagttggtta ttttttacaa
3121 tggtttaggt tgttaagtct cctttgtatg taaggtagtt ttttcaacat ctaaaatttt
3181 tgttttagcc ttcaaaacca acttaccaac ctcagtccag ctgggaaggc agcgttgatt
3241 atggtagttt gtcaagaata tatggacctg gaaacacttt ctctctctgt ccacctggta
3301 gataaattgt cctgttgaga attttttagat ctggactgga actgccagga ccaccgcctc
3361 cagggagtcg ctgggcacct ggaggtatcg tcgatgcctc tcccccatct ttagaaaatt
3421 tggctcttct gaggtcatta ttattttaag aatgattagg attgataagg gtcccatgac
3481 cagcattatg aaaatgcgag agtgggaagg acacagtgtg agacttccac tagaaaaaag
3541 tgaaagttag ggttaggaca tccttttta aaaattacaa attttagtcg ttttggtttt
3601 tgtaatcagg ctaggcacag tggctcacac atggaatccc agcactttgg gaggccgagg
3661 tgggaggatc acttgagccc aggagttcga gaccagccta ggcaacatag caagaccctg
3721 tctgtacaca aaatttaaaa attagttcat cggggtggca cacatcagta gtcccagcta
3781 ctctgcaggc tgaggtggga ggattgcttg aacccaggag gtcgaggctg cagtgagctg
3841 tgatctcacc actgcattcc agcctgggtg acagagttag attccaccct ctcccaccce
3901 ggcaaaaaaa aaaaaaaag atgcaatcaa aggggctgtt ggccagcaat ggcagcagca
3961 gcggcgggca gtctgcccaa gtgtcttagg aaccaaaagc aaataaaagt gtttccatat
4021 atgccaccag ccaagtggcc atcctaattc agaaagaagc tagcctttga gtgtctgtca
4081 tggtgcatcc gtttcagtat tatttcctaa aatgagaagc cctgtgtca acaagatcca
4141 ggggctggag cccaatgcca agcctgtgtt gtccccagcg accctgcagc tgctcgctct
4201 gatgtaccct gtgccattca aggagatgtg gtccaggaaa gtgagcctca tggttttcag
4261 agaagtcatt gttctgttta catttttcata aaacctgttt aaaatagctc cccgtctcag
4321 gctttcagca gtaacagtga gctgactggc aagttcgatg ttagctcccg ggacactcag
4381 cagcgatggt gagcattttg gtttccttaa ggcccagcaa gacttccagg acatctctg
4441 gtgaagccag aatggagaca cccgtgacct caggctgaaa gtcactcgac attggtctct
4501 tgtgttgata gggaaggaaa tcaggcattc ctatttcttt aaataacaaa accactaatt
4561 gccactcaat gctgaaatat tttgggtcac ctaatcatag atttctcagg gcatcaatac
4621 tcaaatatag gctgattatg ccccagttca aatgggaact attaacagag tgcatttctt
4681 gcttgctggg tttcaacaga catcagccaa agaacaaaaa gagatgtcag gacagattcc
4741 aggagtgtcg gagcacatgt gtggcacccg ctccctctgg cagcgaatgt aggaagtcgc
4801 caaatttacc cactcttcaa caagtcattg tttaaacacg gtttttcatt ttctcaactt
4861 ttaatagcaa aaagtgccaa agtcctcaga gacctaacag ccttggtcta ccgtgctgac
4921 cagggtgaag gcacggcgag ggactcctcc cagacgtgcc tctttgtgtgc cagctggctg
4981 tggctcggga gcagacgcag gcctctccat tgtccagggg agcctggcgg cgcatccctc
5041 ctctcccacc tcctggcact tccagctggg tgtcccacat gttggattcc gtccccacca
5101 cacttccaga gaccggagaa ctgtgcaggg cctaaggccg tttggatgaa ttgtcaaaac
5161 aagatgcttc cagttacagc ggcaggagcg ggactgggag cacgggctga cggctgctgg
5221 tgcctttctt cccacctcgc ttgcctgttt ccgcttgacc cttcctccag ctccgatgag
5281 aagagtataa agcatcttcc taacgggtgt gtttgctata cgaacataat ggacgtgaag
5341 tggggcagaa acccagaact cagcattcaa ggatgcccag gagagctgtc cctgttttaa
5401 agagctgtgt tttgttttgt ttcgcattta gagagcagac aaggcaccct tctgctgcgc
5461 tgatacgttt cttacactgg gccatttag accccccaggg aaacagcctt cctggagcgt
5521 tgtctggagg ttccagggac agggcagcct cccagagccg agcaagagct caaggtacaa
5581 atgagagatt tgctataccg tgagaagtca acaacttagc caccacttcc cgcaatgga
5641 ccatgtaaca aatacctcag caggccctgc aaaaggccat gctagagctg aggcgcacag
5701 cctgtggcct ctgtagttag ggcaggtggg atggagactc cttgagtgca cacacctgag
5761 cctgcccaca cacagggag cagcatctcg tatgacgtct ggaaggaact tcggttgtgt
5821 aaagggagcc ttgaagatac gtgcaaaagg tgctacccca atttggtgaa actgacattg
5881 ggcacgtctt gggcttagga gaagcggccg atggtcccgg cctgcagtga caaaccccc
5941 tccccgcacc gcccccagca ccccctctcc tcttcacctc ttcctgctgg ccacgaggaa
6001 gccacttcct cagagagacc ctaccagatg cggatggaaa cagatgcacc aaagcaagcc
6061 ctgatgaaac cgcgacttcc taaggtctgt tcctctgaca cttgcacctg ggcctctctg
6121 tgtttggttc caagcacttc ccacctcaaa ctcccatttt caaaccactg tatctctgcg
6181 cacatctgct acttaccagc cgcatacatg atgcagggtt ttttggtcct gatccagtgg
6241 ccacacctgt ctttgaaatg tctcactgaa ctccagtttt aaaatagatt cattgcttca
6301 acacagcaag cccaatgcac ccagctaaga ctggcttgac cgacagcctg gcctttggtg
6361 gggggcttcc tggggcctgg ggaaagctgg ccaccttcaa cagctggtac ctcttcaaca
6421 gtgtggcctt tcaaaatgca gatgccacca ggagaacatg cccacagctc accacctatg
6481 gatgccatgg ctctgggcag ctttcaaagc aggttcctgt ggtctcctca gctgtttgag
6541 ggggtaacag caaatcagcc tccattttaa aatgaaaaca ccagcctcca gatgtagggc
6601 ctgctgggtg ttgctagccg ctggtcccca ggcacggtgc acttcctcca cctcctgcag
6661 cctccctgtt gtttctagac tcttgcacct ggtgagtgca aggataggtg acccagggc
6721 ctgcagcctt gtcctcagct cccatctcct ggactgccag cctcacccctc tgcagttagc
6781 atggttggcc tgatgcaggg atcccgaggg attacttttt agaccttctt tcacattcag
6841 aaaagtagta tagattcagg agaggcaaga aaattatgct gtccataga gtcacccatg
6901 aagactgatg ccaccacctg aaggctcatg attgttaaaa atgtccacgg gaacctctcg
6961 tccacaggag gtttgtctca acacttccca tttttacggc attggcattg ccaagcatgg
7021 ggaagtatct gctcttctca tgttaaaagt ggcccagctt ttcttaactc agtccaagct
7081 gacttgttta gctgcactgg aatttcttac caaccaaata tttgcatcga caaaggggg
7141 ctgtgtgcac ctcccctaatg gcagcgatga tggctgctgt cattcaagcc catcttcaga
7201 cgtcacagtc tggaagtgaa atgtccacaa acatctgtgg cagaaaaggc tatacggacc
7261 acccagttgt gctgcagctt tacagagcaa ggaagggttg tggcaaataa atgattaacc
7321 tgcctcgact gtgctgaggg caacaaaggc catctcacca aaggattatt cgatgccatt
```

-continued

```
 7381 aaatcatccc gtgaccttcc tgcttccgag tccatggcct ttgcccaggg catgtactcc
 7441 cctgagaggc cttctgccta gaaagatcta tgactggtt ccaaagttga ggcctaggtt
 7501 tttgctggga tttagatatt ttcaggcacc attttgacag cattcaggaa aacggttatt
 7561 gaccccatag actagggtaa gaataaaggc aataaatttg gtctgactca gaatatagga
 7621 gatccatata tttctctgga aaccacagtg tacactaaaa tgtgaaattg aaggtttttgt
 7681 taaaaagaaa aagataatga gcttcatgct ttgtttaatt acataatgat ttccattacg
 7741 ctatttctgt gaaatgcagc aggttcttaa acgttatttc agtggcatgg gctggaagct
 7801 tatcacaaaa agccatgtgt gtggccttat cagaacagaa agagacaggc tggtgcccaa
 7861 ggctgctgcc tgctccacct tttgccagct ctgacctct gaggacgtcc cggcagatct
 7921 ggaatggggc cctcaactga ccatttgctt ctcagaattt cagtttgaga catgagaggt
 7981 ataatcagtt acttttctcc ccccagagaa acccttttgt gaggggagag gagctatggt
 8041 atgtggttca gctgaaacac atacaactgc atcctttggg agtcctttgc caacaaaaac
 8101 agaccaacag accagatgt gtccatgttc aatatcatgt cttgatggac gcagctgatg
 8161 acctcaaata cttgagtggt ctcatggctg ttagatggat tatttgaaaa aaaaaaaaaa
 8221 aaaagagaga aaaaataatt gatttttaca tcagagatag caaactaaga cctggggagg
 8281 ggggtcagct tttatttttat tttattttt ttaagtttgc tagtttgggtc aaatgtgagg
 8341 aggagggagt ctacctgcca cctcttctct tgccctcctt ctgcccacac atccagcatc
 8401 caaaatccat tcatttaatg aattgataaa gtgccgtgca aactggtgca caaacaggcc
 8461 cccagtccac gcagcctggc tcctaggaaa agtggtgacc gggcgtgggg gggcatgccg
 8521 cagccctggg acacagtcgg gcaccttccc cggaccccca ggccttggct gtgcctcaag
 8581 tcagagaggg tcagccttca ggccccggag acgagtgact ggccgatcat ttcacaataa
 8641 aatcactcac ttttggcaac ttcacttttt ttaaggcaca gtcagttcct tttctcatgt
 8701 acctcacaaa agatgaaagac catgtagtac tcttttttggt aaagttacag tgttcatgtt
 8761 aaatatcact ttttttctaca ttgtgtggta aaagaacta cgttaatagc tatatcttaa
 8821 atactgtgat ttgactttt gaaaaatatc ctaatacaaa tattttacta acttacaatc
 8881 actcatttaa taagaaacat ttggattctt ttgaaatcag tgttaattga ctcatattct
 8941 taaaagcctg gctcttgacc ctattggaaa cacaaaggaa gctgaaatca aacatctaaa
 9001 atacactgcg tacacgtgtg cgtgcacaca cacacacaca cacacacaca cacagctctt
 9061 catttctcct gagccatgca gaatttactt tcaatgtgga aatctgttcc cttaccaca
 9121 ctgtatatgc acagagcaca agagaggcta tctctagtca cttccaccag cgaggcctta
 9181 gactccgtat tagaggccac cgatttcata caacagtgtt tcgctaaaga cccttcacta
 9241 ttcttgttta gtaaatagct gtctgctctt cagggaactg ttacctatgg gttattacca
 9301 aagaacgctg gcaattggaa atgtcctgat ggaaattctt tgcacgtgcc ggttctctgg
 9361 catcctccag gtggcccaac ccaaagcaga aagcagaacc cacagacccc gtgagtctcc
 9421 ccataccttg tttccaataa cttggcaaaa cttcttggtg catattggtt acaccctctg
 9481 ggattcataa tgccattagg ctaaaaccct aagagagagg gttgacagaa acacacgcga
 9541 gaatgaggca gatcccagag caaggactgg gcccagactc tccacatgtg ctctactagt
 9601 gagtgcctta tactctcagt attttggggc ttacagcttc ttatttgtgc taaaaaggtg
 9661 cagttccaaa gtaggaactg ccacacaggc cccagcatcc tctctccaac ttcatacctc
 9721 tctcctggtg gggggagcgg gcatccagga cctccggaat caaggatgtg cagagaagag
 9781 cgaaagtaat ttttctagtc acatgaactg attggttcca ggcaattaga aaatggctat
 9841 aaaataacct taattttaaa aaaaaatctt gggtcttcgt tttcctatta ggagactgaa
 9901 ctgaccacat gtattgattt atatcctgaa tatatgggaa ctttctgtgtt tgggatgtcc
 9961 tactgtaaga ctgatgaatg tacagagtta atttcagggt acagttttgc cttaatggtt
10021 ttaaaaaata aactattttt taaaatttt
```

SEQ ID NO: __: NP_005027

```
   1 mvdtesplcp lspleagdle splseeflqe mgniqeisqs igedssgsfg fteyqylgsc
  61 pgsdgsvitd tlspasspss vtypvvpgsv despsgalni ecricgdkas gyhygvhace
 121 gckgffrrti rlklvydkcd rsckiqkknr nkcqycrfhk clsvgmshna irfgrmprse
 181 kaklkaeilt cehdiedset adlkslakri yeaylknfnm nkvkarvils gkasnnppfv
 241 ihdmetlcma ektlvaklva ngiqnkeaev rifhccqcts vetvteltef akaipgfanl
 301 dlndqvtllk ygvyeaifam lssvmnkdgm lvaygngfit reflkslrkp fcdimepkfd
 361 famkfnalel ddsdislfva aiiccgdrpg llnvghiekm qegivhvlrl hlqsnhpddi
 421 flfpkllqkm adlrqlvteh aqlvqiikkt esdaalhpll qeiyrdmy
```

SEQ ID NO:__: NM_015869

```
   1 actgatgtct tgactcatgg gtgtattcac aaattctgtt acttcaagtc ttttctttt
  61 aacggattga tcttttgcta gatagagaca aaatatcagt gtgaattaca gcaaaccct
 121 attccatgct gttatgggtg aaactctggg agattctcct attgacccag aaagcgattc
 181 cttcactgat acactgtctg caaacatatc acaagaaatg accatggttg acacagagat
 241 gccattctgg cccaccaact ttgggatcag ctccgtggat ctctccgtaa tggaagacca
 301 ctcccactcc tttgatatca agcccttcac tactgttgac ttctccagca tttctactcc
 361 acattacgaa gacattccat tcacaagaac agatccagtg gttgcagatt acaagtatga
 421 cctgaaactt caagagtacc aaagtgcaat caagtggga cctgcatctc accttatta
 481 ttctgagaag actcagctct acaataagcc tcatgaagag ccttccaact ccctcatggc
 541 aattgaatgt cgtgtctgtg gagataaagc ttctggattt cactatggga ttcatgcttg
 601 tgaaggatgc aagggtttct tccggagaac aatccagattg aagcttatct atgacagatg
 661 tgatcttaac tgtcggatcc acaaaaaaag tagaaataaa tgtcagtact gtcggtttca
 721 gaaatgcctt gcagtgggga tgtctcataa tgccatcagg tttgggcgga tgccacaggc
 781 cgagaaggag aagctgttgg cggagatctc cagtgatatc gaccagctga atccagagtc
 841 cgctgaccte cgggccctgg caaaacattt gtatgactca tacataaagt ccttcccgct
 901 gaccaaagca aaggcgaggg cgatcttgac aggaaagaca acagacaaat taccattcgt
 961 tatctatgac atgaattcct taatgatggg agaagataaa atcaagttca acacatcac
1021 cccccctgcag gagcagagca aagaggtggc catccgcatc tttcagggct gccagtttcg
1081 ctccgtggga gctgtgtcag agatcacaga gtatgccaaa agcattccgg gttttgtaaa
1141 tcttgacttg aacgaccaag taactctcct caaatatgga gtccacagga tcatttcacac
1201 aatgctggcc tccttgatga taaagatgg ggttctcata tccgagggcc aaggcttcat
1261 gacaagggag tttctaaaga gcctgcgaaa gccttttggt gactttatgg agcccaagtt
1321 tgagtttgct gtgaagttca atgcactgga attagatgac agcgacttgg caatatttat
```

-continued

```
1381 tgctgtcatt attctcagtg gagaccgccc aggtttgctg aatgtgaagc ccattgaaga
1441 cattcaagac aacctgctac aagccctgga gctccagctg aagctgaacc accctgagtc
1501 ctcacagctg tttgccaagc tgctccagaa aatgacagac ctcagacaga ttgtcacgga
1561 acacgtgcag ctactgcagg tgatcaagaa gacggagaca gacatgagtc ttcacccgct
1621 cctgcaggag atctacaagg acttgtacta gcagagagtc ctgagccact gccaacattt
1681 cccttcttcc agttgcacta ttctgaggga aaatctgaca cctaagaaat ttactgtgaa
1741 aaagcatttt aaaaagaaaa ggttttagaa tatgatctat tttatgcata ttgtttataa
1801 agacacattt acaatttact tttaatatta aaaattacca tattatgaaa aaaaaaaaaa
1861 aaa
```

SEQ ID NO:__: NP_056953

```
  1 mgetlgdspi dpesdsftdt lsanisqemt mvdtempfwp tnfgissvdl svmedhshsf
 61 dikpfttvdf ssistphyed ipftrtdpvv adykydlklq eyqsaikvep aspppyysekt
121 qlynkpheep snslmaiecr vcgdkasgfh ygvhacegck gffrrtirlk liydrcdlnc
181 rihkksrnkc qycrfqkcla vgmshnairf grmpqaekek llaeissdid qlnpesadlr
241 alakhlydsy iksfpltkak arailtgktt dkspfviydm nslmmgedki kfkhitplqe
301 qskevairif qgcqfrsvea vqeiteyaks ipgfvnldln dqvtllkygv heiiytmlas
361 lmnkdgvlis egqgfmtref lkslrkpfgd fmepkfefav kfnaleldds dlaifiavii
421 lsgdrpglln vkpiediqdn llqaleiqlk lnhpessqlf akllqkmtdl rqivtehvql
481 lqvikktetd mslhpllqei ykdly
```

SEQ ID NO:__: NM_006238

```
   1 gttttggcag gagcgggaga attctgcgga gcctgcggga cggcggcggt ggcgccgtag
  61 gcagccggga cagtgttgta cagtgttttg ggcatgcacg tgatactcac acagtggctt
 121 ctgctcacca acagatgaag acagatgcac caacgagggt ctggaatggc tggagtggt
 181 ctggaaagca gggtcagata cccctggaaa actgaaggcc gtggagcagt gatctctaca
 241 ggactgcttc aaggctgatg ggaaccaccc tgtagaggtc catctgcgtt cagacccaga
 301 cgatgccaga gctatgactg ggcctgcagg tgtggcgccg aggggagatc agccatggag
 361 cagccacagg aggaagcccc tgaggtccgg gaagaggagg agaaagagga agtggcagag
 421 gcagaaggag ccccagagct caatggggga ccagcagcat cacttccttc cagcagctac
 481 acagacctct ccccggagct ctcgccaccc tcactgctgg accaactgca gatgggctgt
 541 gacggggcct catgcggcag cctcaacatg gagtgccggg tgtgcgggga caaggcatcg
 601 ggcttccact acggtgttca tgcatgtgag gggtgcaagg gcttcttccg tcgtacgatc
 661 cgcatgaagc tggagtacga gaagtgtgac cgcagctgca agattcagaa gaagaaccgc
 721 aacaagtgcc agtactgccg cttccagaag tgcctggcac tgggcatgtc acacaacgct
 781 atccgttttg gtcggatgcc ggaggctgag aagaggaagc tggtggcagg gctgactgca
 841 aacgagggga gccagtacaa cccacaggtg gccgacctga aggccttctc caagcacatc
 901 tacaatgcct acctgaaaaa cttcaacatg accaaaaaga aggcccgcag catcctcacc
 961 ggcaaagcca gccacacggc gcccttcgtg atccacgaca tcgagacatt gtggcaggcn
1021 gagaagggc tggtgtggaa gcagttggtg aatgcctgc ctccctacaa ggagatcagc
1081 gtgcacgtct tctaccgctg ccagtgcacc acagtggaga ccgtgcggga gctcactgag
1141 ttcgccaaga gcatcccgag cttcagcagc ctcttcctca acgaccaggt taccccttcte
1201 aagtatgcg tgcacgagc catcccgcc atgctgcct atcgtcaa caaggacggg
1261 ctgctggtag ccaacgcag tggcttttc acccgtgagt tcctgcgcag cctccgcaaa
1321 cccttcagtg atatcattga gcctaagttt gaatttgctg tcaagttcaa cgccctggaa
1381 cttgatgaca gtgacctggc cctattcatt gcggccatca ttctgtgtgg agaccggcca
1441 ggcctcatga acgttccacg ggtggaggct atccaggaca ccatcctgcc tgccctgcaa
1501 ttccacctgc aggccaacca ccctgatgcc cagtacctct tccccaagct gctgcagaag
1561 atggctgacc tgcggcaact ggtcaccgag cacgcccaga tgatgcagcg gatcaagaag
1621 accgaaaccg agacctcgct gcaccctctg ctccaggaga tctacaagga catgtactaa
1681 cggcggcacc caggcctccc tgcagactcc aatggggcca gcactggagg gcccaccca
1741 catgactttt ccattgacca gctctcttcc tgtctttgtt gtctccctct ttctcagttc
1801 ctctttcttt tctaattcct gttgctctgt ttcttccttt ctgtaggttt ctctcttccc
1861 ttctcccttg ccctcccttt ctctctccac cccccacgtc tgtcctcctt tcttattctg
1921 tgagatgttt tgtattattt caccagcagc atagaacagg acctctgctt ttgcacacct
1981 tttccccagg agcagaagag agtggggcct gccctctgcc ccatcattgc acctgcaggc
2041 ttaggtcctc acttctgtct cctgtcttca gagcaaaaga cttgagccat ccaaagaaac
2101 actaagctct ctgggcctgg gttccaggga aggctaagca tggcctggac tgactgcagc
2161 cccctatagt catggggtcc ctgctgcaaa ggacagtggg caggaggccc caggctgaga
2221 gccagatgcc tccccaagac tgtcattgcc cctccgatgc tgaggccacc cactgaccca
2281 actgatcctg ctccagcagc acacctcagc ccactgaca cccagtgtcc ttccatcttc
2341 acactggttt gccaggccaa tgttgctgat ggccctcca gcacacacac ataagcactg
2401 aaatcacttt acctgcaggc tccatgcacc tccctcctt cctgaggca ggtgagaacc
2461 cagagagagg ggcctgcagg tgagcaggca gggctgggc aggtctccgg ggaggcaggg
2521 gtcctgcagg tcctggtggg tcagcccagc acctgctccc agtgggagct tcccgggata
2581 aactgagcct gttcattctg atgtccattt gtcccaatag ctctactgcc ctcccttcc
2641 cctttactca gcccagctgg ccacctagaa gtctccctgc acagcctcta gtgtccgggg
2701 accttgtggg accagtccca caccgtcggt ccctgccctc ccctgctccc aggttgaggt
2761 gcgctcacct cagagcaggg ccaaagcaca gctgggcatg ccatgtctga gcggcgcaga
2821 gccctccagg cctgcagggg caaggggctg gctggagtct cagagcacag aggtaggaga
2881 actggggttc aagcccaggc ttcctgggtc ctgcctggtc tccctccca aggagccatt
2941 ctgtgtgtga ctctgggtgg aagtgcccag ccctgcccc tacgggcgct gcagcctccc
3001 ttccatgccc caggatcact ctctgctggc aggattcttc ccgctcccca cctacccagc
3061 tgatgggggt tggggtgctt cctttcaggc caaggctatg aagggacagc tgctgggacc
3121 cacctccccc tccccggcca catgccgcgt ccctgccccg acccgggtct ggtgctgagg
3181 atacagctct tctcagtgtc tgaacaatct ccaaaattga aatgtatatt tttgctagga
3241 gccccagctt cctgtgtttt aatataaat agtgtacaca gactgacgaa actttaaata
3301 aatgggaatt aaatatttaa aaaaaaaaaa
```

```
SEQ ID NO:__: NP_006229
  1  meqpqeeape vreeeekeev aeaegapeln ggpqhalpss sytdlsrsss ppslldqlqm
 61  gcdgascgsl nmecrvcgdk asgfhygvha cegckgffrr tirmkleyek cersckiqkk
121  nrnkcqycrf qkclalgmsh nairfgrmpe aekrklvagl tanegsqynp qvadlkafsk
181  hiynaylknf nmtkkkarsi ltgkashtap fvihdietlw qaekglvwkq lvnglppyke
241  isvhvfyrcq cttvetvrel tefaksipsf sslflndqvt llkygvheai famlasivnk
301  dgllvangsg fvtreflrsl rkpfsdiiep kfefavktna lelddsdlal fiaaiilcgd
361  rpglmnvprv eaiqdtilra lefhlqanhp daqylfpkll qkmadlrqlv tehaqmmqri
421  kktetetslh pllqeiykdm y
```

---

What is claimed is:

1. A compound having the chemical structure

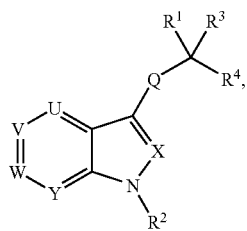

pharmaceutically acceptable salts, tautomers and stereoisomers thereof, wherein:

U, V, W, X, and Y are $CR^5$;

Q is —O—, —S—, or —$NR^{51}$—;

$R^1$ is selected from the group consisting of optionally substituted carboxyl and a carboxylic acid isostere;

$R^2$ is —$S(O)_2NR^6R^7$ or —$S(O)_2R^9$;

$R^3$ and $R^4$ are independently selected from the group consisting of hydrogen, optionally substituted lower alkyl, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl, or $R^3$ and $R^4$ may combine to form a 3-7-membered optionally substituted mono-cycloalkyl or 3-7-membered optionally substituted mono-heterocycloalkyl;

$R^5$ at each occurrence is independently selected from the group consisting of hydrogen, halo, optionally substituted lower alkyl, optionally substituted lower alkenyl, optionally substituted lower alkynyl, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, —$OR^{10}$, —$SR^{11}$, —$NR^{12}R^{13}$, —$C(Z)NR^6R^7$, —$C(Z)R^8$, —$S(O)_2NR^6R^7$, and —$S(O)_nR^9$;

$R^6$ and $R^7$ at each occurrence are independently selected from the group consisting of hydrogen, optionally substituted lower alkyl, optionally substituted lower alkenyl, provided, however, that when $R^6$ and/or $R^7$ are optionally substituted lower alkenyl, no alkene carbon thereof is bound to nitrogen, optionally substituted lower alkynyl, provided, however, that when $R^6$ and/or $R^7$ are optionally substituted lower alkynyl, no alkyne carbon thereof is bound to nitrogen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl, or $R^6$ and $R^7$ together with the nitrogen to which they are attached form a 5-7 membered optionally substituted heterocycloalkyl or 5-7 membered optionally substituted heteroaryl;

$R^8$ at each occurrence is independently selected from the group consisting of optionally substituted lower alkyl, optionally substituted lower alkenyl, provided, however, that when $R^8$ is optionally substituted lower alkenyl, no alkene carbon thereof is bound to —C(Z)-, optionally substituted lower alkynyl, provided, however, that when $R^8$ is optionally substituted lower alkynyl, no alkyne carbon thereof is bound to —C(Z)-, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, and —OR$^{11}$;

$R^9$ at each occurrence is independently selected from the group consisting of optionally substituted lower alkyl, optionally substituted lower alkenyl, provided, however, that when $R^9$ is optionally substituted lower alkenyl, no alkene carbon thereof is bound to —S(O)$_n$—, optionally substituted lower alkynyl, provided, however, that when $R^9$ is optionally substituted lower alkynyl, no alkyne carbon thereof is bound to —S(O)$_n$—, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl;

$R^{10}$ at each occurrence is independently selected from the group consisting of hydrogen, optionally substituted lower alkyl, optionally substituted lower alkenyl, provided, however, that when $R^{10}$ is optionally substituted lower alkenyl, no alkene carbon thereof is bound to oxygen, optionally substituted lower alkynyl, provided, however, that when $R^{10}$ is optionally substituted lower alkynyl, no alkyne carbon thereof is bound to oxygen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, —C(Z)R$^8$, and —C(Z)NR$^6$R$^7$;

$R^{11}$ at each occurrence is independently selected from the group consisting of hydrogen, optionally substituted lower alkyl, optionally substituted lower alkenyl, provided, however, that when $R^{11}$ is optionally substituted lower alkenyl, no alkene carbon thereof is bound to S or O, optionally substituted lower alkynyl, provided, however, that when $R^{11}$ is optionally substituted lower alkynyl, no alkyne carbon thereof is bound to S or O, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl;

$R^{12}$ and $R^{13}$ at each occurrence are independently selected from the group consisting of hydrogen, optionally substituted lower alkyl, optionally substituted lower alkenyl, provided, however, that when $R^{12}$ and/or $R^{13}$ are optionally substituted lower alkenyl, no alkene carbon thereof is bound to nitrogen, optionally substituted lower alkynyl, provided, however, that when $R^{12}$ and/or $R^{13}$ are optionally substituted lower alkynyl, no alkyne carbon thereof is bound to nitrogen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, —C(Z)R$^8$, —C(Z)NR$^6$R$^7$, —S(O)$_2$R$^9$, and —S(O)$_2$NR$^6$R$^7$, or $R^{12}$ and $R^{13}$ together with the nitrogen to which they are attached form a 5-7 membered optionally substituted heterocycloalkyl or 5-7 membered optionally substituted heteroaryl;

$R^{51}$ is selected from the group consisting of hydrogen, optionally substituted lower alkyl, optionally substituted lower alkenyl, provided, however, that when $R^{51}$ is optionally substituted lower alkenyl, no alkene carbon thereof is bound to nitrogen, optionally substituted lower alkynyl, provided, however, that when $R^{51}$ is optionally substituted lower alkynyl, no alkyne carbon thereof is bound to nitrogen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl —C(Z)NR$^6$R$^7$, —C(Z)R$^8$, —S(O)$_2$NR$^6$R$^7$, and —S(O)$_2$R$^9$;

n is 1 or 2; and

Z is O or S.

2. The compound of claim 1, wherein U, W, X, and Y are CH, and V is CR$^5$.

3. The compound of claim 2, wherein R$^5$ is selected from the group consisting of hydrogen, halo, lower alkyl optionally substituted with 1-3 fluoro, lower alkylthio optionally substituted with 1-3 fluoro, and lower alkoxy optionally substituted with 1-3 fluoro.

4. A compound having the chemical structure

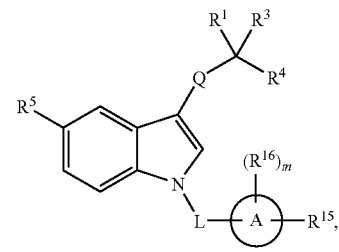

pharmaceutically acceptable salts, tautomers and steroisomers thereof, wherein:

Q is —O—, —S—, or —NR$^{51}$—;

R$^1$ is selected from the group consisting of optionally substituted carboxyl and a carboxylic acid isostere;

R$^3$ and R$^4$ are independently selected from the group consisting of hydrogen, optionally substituted lower alkyl, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl,or $R^3$ and $R^4$ may combine to form a 3-7 membered optionally substituted mono-cycloalkyl or 3-7 membered optionally substituted mono-heterocycloalkyl;

$R^5$ is independently selected from the group consisting of hydrogen, halo, optionally substituted lower alkyl, optionally substituted lower alkenyl, optionally substituted lower alkynyl, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, —$OR^{10}$, —$SR^{11}$, —$NR^{12}R^{13}$, —$C(Z)NR^6R^7$, —$C(Z)R^8$, —$S(O)_2NR^6R^7$, and —$S(O)_nR^9$;

$R^6$ and $R^7$ at each occurrence are independently selected from the group consisting of hydrogen, optionally substituted lower alkyl, optionally substituted lower alkenyl, provided, however, that when $R^6$ and/or $R^7$ are optionally substituted lower alkenyl, no alkene carbon thereof is bound to nitrogen, optionally substituted lower alkynyl provided, however, that when $R^6$ and/or $R^7$ are optionally substituted lower alkynyl, no alkyne carbon thereof is bound to nitrogen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl, or $R^6$ and $R^7$ together with the nitrogen to which they are attached form a 5-7 membered optionally substituted heterocycloalkyl or 5-7 membered optionally substituted heteroaryl;

$R^8$ at each occurrence is independently selected from the group consisting of optionally substituted lower alkyl, optionally substituted lower alkenyl, provided, however, that when $R^8$ is optionally substituted lower alkenyl, no alkene carbon thereof is bound to —C(Z)-, optionally substituted lower alkynyl, provided, however, that when $R^8$ is optionally substituted lower alkynyl, no alkyne carbon thereof is bound to —C(Z)-, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, and —$OR^{11}$;

$R^9$ at each occurrence is independently selected from the group consisting of optionally substituted lower alkyl, optionally substituted lower alkenyl, provided, however, that when $R^9$ is optionally substituted lower alkenyl, no alkene carbon thereof is bound to —$S(O)_n$—, optionally substituted lower alkynyl, provided, however, that when $R^9$ is optionally substituted lower alkynyl, no alkyne carbon thereof is bound to —$S(O)_n$—, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl;

$R^{10}$ at each occurrence is independently selected from the group consisting of hydrogen, optionally substituted lower alkyl, optionally substituted lower alkenyl, provided, however, that when $R^{10}$ is optionally substituted lower alkenyl, no alkene carbon thereof is bound to oxygen, optionally substituted lower alkynyl, provided, however, that when $R^{10}$ is optionally substituted lower alkynyl, no alkyne carbon thereof is bound to oxygen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, —$C(Z)R^8$, and —$C(Z)NR^6R^7$;

$R^{11}$ at each occurrence is independently selected from the group consisting of hydrogen, optionally substituted lower alkyl, optionally substituted lower alkenyl, provided, however, that when $R^{11}$ is optionally substituted lower alkenyl, no alkene carbon thereof is bound to S or O, optionally substituted lower alkynyl, provided, however, that when $R^{11}$ is optionally substituted lower alkynyl, no alkyne carbon thereof is bound to S or O, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl;

$R^{12}$ and $R^{13}$ at each occurrence are independently selected from the group consisting of hydrogen, optionally substituted lower alkyl, optionally substituted lower alkenyl, provided, however, that when $R^{12}$ and/or $R^{13}$ are optionally substituted lower alkenyl, no alkene carbon thereof is bound to nitrogen, optionally substituted lower alkynyl, provided, however, that when $R^{12}$ and/or $R^{13}$ are optionally substituted lower alkynyl, no alkyne carbon thereof is bound to nitrogen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, —$C(Z)R^8$, —$C(Z)NR^6R^7$, —$S(O)_2R^9$, and —$S(O)_2NR^6R^7$, or $R^{12}$ and $R^{13}$ together with the nitrogen to which they are attached form a 5-7 membered optionally substituted heterocycloalkyl or 5-7 membered optionally substituted heteroaryl;

$R^{15}$ is selected from the group consisting of hydrogen, halo, cyano, nitro, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —$OR^{10}$, —$SR^{11}$, —$NR^{12}R^{13}$, —$C(Z)NR^6R^7$, —$C(Z)R^8$, —$S(O)_2NR^6R^7$, and —$S(O)_nR^9$, attached to A at any available atom to produce a stable compound;

$R^{16}$ at each occurrence is independently selected from the group consisting of halo, lower alkyl, hydroxyl, lower alkoxy, thiol, and lower alkylthio, wherein lower alkyl and the lower alkyl chains of lower alkoxy and lower alkylthio are optionally substituted with fluoro, hydroxyl, lower alkoxy, thiol, or lower alkylthio, provided, however, that any substitution on lower alkoxy or lower alkylthio does not result in O or S bound to the carbon that is bound to the alkoxy oxygen of substituted lower alkoxy or the alkylthio sulfur of substituted lower alkylthio;

A is a monocyclic or bicyclic ring selected from the group consisting of cycloalkyl, heterocycloalkyl, aryl or heteroaryl;

L is —S(O)$_2$NR$^{56}$— or —S(O)$_2$—, attached to A at any available atom to produce a stable compound;

R$^{51}$ is selected from the group consisting of hydrogen, optionally substituted lower alkyl, optionally substituted lower alkenyl, provided, however, that when R$^{51}$ is optionally substituted lower alkenyl, no alkene carbon thereof is bound to nitrogen, optionally substituted lower alkynyl, provided, however, that when R$^{51}$ is optionally substituted lower alkynyl, no alkyne carbon thereof is bound to nitrogen, optionally substituted cycloalkyl, optionally substituted cycloalkylalkyl, optionally substituted heterocycloalkyl optionally substituted heterocycloalkylalkyl, optionally substituted aryl, optionally substituted aralkyl, optionally substituted heteroaryl, optionally substituted heteroaralkyl, —C(Z)NR$^6$R$^7$, —C(Z)R$^8$, —S(O)$_2$NR$^6$R$^7$, and —S(O)$_2$R$^9$;

R$^{54}$ and R$^{55}$ are independently lower alkyl or combine with the nitrogen to which they are attached to form a 5-7 membered heterocycloalkyl or 5-7 membered heterocycloalkyl substituted with halo, hydroxyl, lower alkoxy, or lower alkyl;

R$^{56}$ is selected from the group consisting of hydrogen, optionally substituted lower alkyl, optionally substituted lower alkenyl, provided, however, that when R$^{56}$ is optionally substituted lower alkenyl, no alkene carbon thereof is bound to nitrogen, optionally substituted lower alkynyl, provided, however, that when R$^{56}$ is optionally substituted lower alkynyl, no alkyne carbon thereof is bound to nitrogen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl;

m is 0, 1, or 2;

n is 1 or 2; and

Z is O or S.

5. The compound of claim 4, wherein A is monocyclic aryl or monocyclic heteroaryl.

6. The compound of claim 5, wherein:

R$^{15}$ is selected from the group consisting of optionally substituted cycloalkyl, optionally substituted heterocycloalkyl, optionally substituted aryl, optionally substituted heteroaryl, —OR$^{10}$, —SR$^{11}$, —NR$^{12}$R$^{13}$, —C(Z)NR$^6$R$^7$, —C(Z)R$^8$, —S(O)$_2$NR$^6$R$^7$, and —S(O)$_n$R$^9$.

7. The compound of claim 6, wherein:

one of R$^6$ and R$^7$, one of R$^{12}$ and R$^{13}$, R$^8$, R$^9$, R$^{10}$, and R$^{11}$ are selected from the group consisting of optionally substituted cycloalkyl, optionally substituted heterocycloalkyl, optionally substituted aryl, and optionally substituted heteroaryl, 8. The compound of claim 7, wherein R$^3$ and R$^4$ are H, and Q is O.

9. A composition comprising:
a pharmaceutically acceptable carrier; and
a compound according to claim 1.

10. A kit comprising a composition according to claim 9.

11. A composition comprising:
a pharmaceutically acceptable carrier; and
a compound according to claim 4.

12. A kit comprising a composition according to claim 11.

* * * * *

UNITED STATES PATENT AND TRADEMARK OFFICE
CERTIFICATE OF CORRECTION

PATENT NO. : 7,531,568 B2
APPLICATION NO. : 11/289656
DATED : November 29, 2005
INVENTOR(S) : Jack Lin et al.

It is certified that error appears in the above-identified patent and that said Letters Patent is hereby corrected as shown below:

Title Page, Item (73) Assignee:

"(73)   Assignee:   Plexxikon, Inc., Berkeley, CA (US)", should read,

-- (73)   Assignee:   Plexxikon Inc., Berkeley, CA (US) --

Signed and Sealed this
Fifth Day of June, 2012

David J. Kappos
*Director of the United States Patent and Trademark Office*